US009121036B2

(12) United States Patent
Alphey

(10) Patent No.: US 9,121,036 B2

(45) Date of Patent: Sep. 1, 2015

(54) EXPRESSION SYSTEM FOR INSECT PEST CONTROL

(75) Inventor: Luke Alphey, Abingdon (GB)

(73) Assignee: Oxitec Limited, Abingdon (GB)

( * ) Notice: Subject to any disclaimer, the term of this patent is extended or adjusted under 35 U.S.C. 154(b) by 602 days.

(21) Appl. No.: 10/566,448

(22) PCT Filed: Jul. 28, 2004

(86) PCT No.: PCT/GB2004/003263

§ 371 (c)(1), (2), (4) Date: Apr. 18, 2006

(87) PCT Pub. No.: WO2005/012534

PCT Pub. Date: Feb. 10, 2005

(65) Prior Publication Data

US 2007/0056051 A1 Mar. 8, 2007

(30) Foreign Application Priority Data

Jul. 28, 2003 (GB) .................................. 0317656.7

(51) Int. Cl.

| | |
|---|---|
| ***C12N 15/00*** | (2006.01) |
| ***A01K 67/00*** | (2006.01) |
| ***C12N 15/85*** | (2006.01) |
| ***A01K 67/033*** | (2006.01) |

(52) U.S. Cl.

CPC ........ *C12N 15/8509* (2013.01); *A01K 67/0333* (2013.01); *C12N 15/85* (2013.01); *A01K 2217/05* (2013.01); *A01K 2217/20* (2013.01); *A01K 2227/70* (2013.01); *A01K 2227/706* (2013.01); *A01K 2267/02* (2013.01); *C12N 2830/007* (2013.01); *C12N 2830/008* (2013.01)

(58) Field of Classification Search

CPC ....................... A01K 2217/05; A01K 67/0271

See application file for complete search history.

(56) References Cited

U.S. PATENT DOCUMENTS

| | | | | |
|---|---|---|---|---|
| 5,254,801 | A | 10/1993 | Dotson et al. | |
| 5,278,057 | A | 1/1994 | Jorgensen | |
| 5,670,353 | A | 9/1997 | Ahlquist et al. | |
| 5,674,747 | A | 10/1997 | Hammock et al. | |
| 5,773,697 | A | 6/1998 | Tomes et al. | |
| 5,851,796 | A | 12/1998 | Schatz | |
| 5,977,441 | A | 11/1999 | Oliver et al. | |
| 6,200,800 | B1 | 3/2001 | Choulika et al. | |
| 6,338,040 | B1 | 1/2002 | Buman et al. | |
| 6,962,810 | B2 | 11/2005 | Fraser et al. | |
| 7,998,475 | B2 | 8/2011 | Alphey | |
| 8,124,404 | B2 | 2/2012 | Alphey | |
| 2003/0150007 | A1 * | 8/2003 | Savakis et al. | 800/21 |
| 2003/0213005 | A1 | 11/2003 | Alphey et al. | |
| 2004/0082032 | A1 | 4/2004 | Bovi et al. | |
| 2005/0221430 | A1 | 10/2005 | Prentice | |
| 2006/0212949 | A1 | 9/2006 | Alphey | |
| 2006/0242717 | A1 | 10/2006 | Alphey | |
| 2006/0275276 | A1 | 12/2006 | Alphey | |
| 2007/0056051 | A1 | 3/2007 | Alphey | |
| 2008/0115233 | A1 | 5/2008 | Alphey et al. | |
| 2009/0170793 | A1 | 7/2009 | Gaur | |
| 2009/0183269 | A1 | 7/2009 | Alphey | |

FOREIGN PATENT DOCUMENTS

| | | | |
|---|---|---|---|
| EP | 0 636 310 | | 2/1995 |
| EP | 0955364 | A2 * | 11/1999 |
| GB | 2355459 | | 4/2001 |
| WO | WO-90/08830 | | 8/1990 |
| WO | WO-94/03619 | | 2/1994 |
| WO | WO-96/04393 | | 2/1996 |
| WO | WO-96/24605 | | 8/1996 |
| WO | WO-97/30162 | | 8/1997 |
| WO | 98/08960 | | 3/1998 |
| WO | WO-99/10488 | | 3/1999 |
| WO | WO 00/73510 | A1 * | 12/2000 |
| WO | WO 01/39599 | | 6/2001 |
| WO | WO 01/59088 | | 8/2001 |
| WO | 01/91802 | | 12/2001 |
| WO | 02/46444 | | 6/2002 |
| WO | 02/101061 | | 12/2002 |
| WO | 2004/044150 | | 5/2004 |
| WO | 2004/098278 | | 11/2004 |
| WO | 2004/108933 | | 12/2004 |
| WO | 2005/003364 | | 1/2005 |
| WO | WO 2005/012534 | | 2/2005 |
| WO | 2007/091099 | | 8/2007 |

OTHER PUBLICATIONS

Loukeris et al (PNAS, 92: 9485-9489, 1995.*

Horn et al (Dev Genes Evol, 210:623-629, 2000.*

Gossen et al (Tetracycline in Biology, Chemistry and Medicine, pp. 139-157, 2001).*

Fussenegger et al (Biotechnol Prog, 13: 733-740, 1997).*

Pane et al (Development 129: 3715-3725 (2002).*

Alphey et al. (May 2002) "Dominant Lethality and Insect Population Control," *Mol. Biochem. Parasitol.* 121(2):173-178.

Bieschke et al. (Jun. 1998) "Doxycycline-Induced Transgene Expression During *Drosophila* Development and Aging," *Mol. Gen Genet.* 258(6):571-579.

Chen et al. (Oct. 2000) "The Use of Modified Tetracycline Regulatory Expression System with Reduced Basal Level to Develop and in Vivo Biopesticide Expression System," *Food Sci Agricult. Chem.* 2(4):220-225.

Ernst, U. (1991) "Regulation of Sexual Differentiation in *Drosophila*: Alternative Splicing of the Transformer Primary Transcript Requires Masking of the Non-Specific Acceptor Site in Females," Inaugural Dissertation, Aus Frankfurt / Main, BRD (Abstract Only).

(Continued)

*Primary Examiner* — Anoop Singh

*Assistant Examiner* — David A Montanari

(74) *Attorney, Agent, or Firm* — Morrison & Foerster LLP

(57) ABSTRACT

Promoters active in insects can be enhanced by positive feedback mechanisms and associated with repressible lethal effects.

17 Claims, 16 Drawing Sheets

(56) References Cited

OTHER PUBLICATIONS

Heinrich et al. (Jul. 18, 2000) "A Repressible Female-Specific Lethal Genetic System for Making Transgenic Insect Strains Suitable for a Sterile-Release Program," *Proc. Nat. Acad. Sci. USA* 97:8229-8232.
Hofmann et al.(1996) "Rapid Retroviral Delivery of Tetracycline-Inducible Genes in a Single Autoregulatory Cassette," *Proc. Nat. Acad. Sci. USA* 93:5185-5190.
Horn et al. (Jan. 2003) "A Transgene-Based Embryo-Specific Lethality System for Insect Pest Management," *Nat. Biotechnol.* 21(1):64-70.
Louis et al. (Nov. 2003) "A Theoretical Model for the Regulation of Sex-Lethal, a Gene That Controls Sex Determination and Dosage Compensation in *Drosophila melanogaster," Genetics* 165:1355-1384.
Saccone et al. (2000) "Sex Determination in Medfly: A Molecular Approach," In; *Area-Wide Control of Fruit Flies and Other Pest Insects*, Tan, K.H. ed., Penerbit USM, Penag, pp. 491-496.
Shockett et al. (Jul. 1995) "A Modified Tetracycline-Regulated System Provides Autoregulatory, Inducible Gene Expression in Cultured Cells and Transgenic Mice," *Proc. Nat. Acad. Sci. USA* 92:6522-6526.
Stebbins et al. (2001) "Tetracycline-Inducible Systems for *Drosophila," Proc. Nat. Acad. Sci. USA*. 98:10775-10780.
Stebbins et al. (2001) "Adaptable Doxycycline-Regulated Gene Expression Systems for *Drosophila," Gene* 270:103-111.
Thomas et al. (Mar. 2000) "Insect Population Control Using Dominant, Repressible, Lethal Genetic System," *Science* 287:2474-2476.
Wu et al. (Jun. 2000) "Expression of Highly Controllable Genes in Insect Cells Using a Modified Tetracycline-Regulated Gene Expression System," *J. Biotechnol.* 80(1):75-83.
Search Report Corresponding to Great Britain Patent Application No. GB 0317656.7, Date of Search Nov. 25, 2003.
Search Report Corresponding to Great Britain Patent Application No. GB 0621234.4, Date of Search Feb. 21, 2007.
Search Report Corresponding to International Application No. PCT/GB2004/003263, Mailed May 11, 2004.
Examination Report for European patent application serial No. 04 743 590.4-121 dated Nov. 14, 2008.
EP First Office Action, dated Feb. 16, 2012, in European Patent Application No. 04743590.4, a corresponding application, 8 pp.
Fussenegger et al. (1998) "Regulated Multicistronic Expression Technology for Mammalian Metabolic Engineering," Cytotechnology 28:111-125.
Fux et al. (2003) "Novel Macrolide-Adjustable Bidirectional Expression Modules for Coordinated Expression of Two Different Transgenes in Mice," J Gene Medicine 5:1067-1079.
Schwechheimer et al. (2000) "Transactivation of a Target Gene Through Feedforward Loop Activation in Plants," Funct Integr Genomics 1:35-43.
Adelman et al., "Formation and loss of large, unstable tandem arrays of the piggyBac transposable element in the yellow fever mosquito, *Aedes aegypti*," Transgenic Res (2004) 13(5):411-425.
Alphey et al., "Modeling resistance to genetic control of insects," Journal of Theoretical Biology (2011) 270:42-55.
Atkinson et al., "Genetic transformation systems in insects," Annu Rev Entomol (2001) 46:317-346.
Bello et al., "Spatial and temporal targeting of gene expression in *Drosophila* by means of a tetracycline-dependent transactivator system," Development (1998) 125(12):2193-2202.
Beullens et al., "The isolation of novel inhibitory polypeptides of protein phosphatase 1 from bovine thymus nuclei," J Biol Chem (1992) 267(23):16538-16544.
Beullens et al., "Inactivation of nuclear inhibitory polypeptides of protein phosphatase-1 (NIPP-1) by protein kinase A," J Biol Chem (1993) 268(18):13172-13177.
Beullens et al., "Molecular determinants of nuclear protein phosphatase-1 regulation by NIPP-1," J Biol Chem (1999) 274(20):14053-14061.
Boudrez et al., "Identification of MYPT1 and NIPP1 as subunits of protein phosphatase 1 in rat liver cytosol," FEBS Letters 455 (1999) 175-178.
Burcin et al., "A regulatory system for target gene expression," Frontiers in Biosc. (1998) 3:c1-7.
Communication pursuant to Article 96(2) EPC for EP 00979774.7, mailed Mar. 8, 2006, 4 pages.
Communication pursuant to Article 96(2) EPC for EP 00979774.7, mailed Aug. 2, 2005, 4 pages.
Communication pursuant to Article 96(2) EPC for EP 00979774.7, mailed Oct. 4, 2004, 4 pages.
Communication pursuant to Article 96(2) EPC for EP 00979774.7, mailed Nov. 28, 2003, 5 pages.
Communication under Rule 51(4) EPC, directed to EP 00979774.7, mailed May 9, 2007, 4 pages.
Decision on Further Processing for EP 00979774.7, mailed Jan. 29, 2007, 1 page.
Deng et al., "A targeted gene silencing technique shows that *Drosophila* myosin VI is required for egg chamber and imaginal disc morphogenesis," J Cell Science (1999) 112:3677-3690.
Devault et al., "Biotechnology and new integrated pest management approaches," Nature Biotechnology (1996) 14:46-49.
Egloff et al., "Structural basis for the recognition of regulatory subunits by the catalytic subunit of protein phosphatase 1," EMBO J (1997) 16(8):1876-1887.
Examination Report for NZ 519175, mailed Jul. 9, 2002, 2 pages.
Examination Report for NZ 519175, mailed Nov. 28, 2003, 1 page.
Fryxell et al., "Autocidal biological control: a general strategy for insect control based on genetic transformation with a highly conserved gene," J Econ Entomol (1995) 88(5):1221-1232.
Fu et al., "Female-specific flightless phenotype for mosquito control," PNAS (2010) 107(10):4550-4554.
"Gene Linkage and Genetic Mapping," in Essential Genetics, Daniel L. Hartl and Elizabeth W. Jones (eds.), (1999) Jones and Bartlett Publishers, Sudbury, Massachussetts, pp. 126-127.
Golovnin et al., "The su(Hw) insulator can disrupt enhancer-promoter interactions when located more than 20 kilobases away from the *Drosophila* achaete-scute complex," Mol Cell Biol (1999) 19(5):3443-3456.
Guo et al., "Species-specific signals for the splicing of a short *Drosophila* intron in vitro," Mol Cell Biol (1993) 13(2):1104-1118.
Harris et al., "Field performance of engineered male mosquitoes," Nature Biotechnology (2011) 29(11):1034-1039.
Inoue et al., "Binding of the *Drosophila* Sex-lethal gene product to the alternative splice site of transformer primary transcript," Nature (1990) 344:461-463.
International Search Report for PCT/GB00/04541, mailed Dec. 5, 2001.
Jagiello et al., "NIPP-1, a nuclear inhibitory subunit of protein phosphatase-1, has RNA-binding properties," J Biol Chem (1997) 272(35):22067-22071.
Jin et al., "Mapping of the RNA-binding and endoribonuclease domains of NIPP1, a nuclear targeting subunit of protein phosphatase 1," Biochem J (1999) 342:13-19.
Krafsur, "Bionomics of the face fly, *Musca autumnalis*," Annu Rev Entomol (1997) 42:503-523 (Abstract).
Namciu et al., "Human matrix attachment regions insulate transgene expression from chromosomal position effects in *Drosophila melanogaster*," Mol Cell Biol (1998) 18(4):2382-2391.
Nitasaka et al., "Repressor of P elements in *Drosophila melanogaster*: Cytotype determination by a defective P element carrying only open reading frames 0 through 2," Proc Natl Acad Sci USA (1987) 84(21):7605-7608.
O'Brochta et al., "Gene vector and transposable element behavior in mosquitos," J Exp Biol (2003) 206(Pt 21):3823-3834.
Office Action in U.S. Appl. No. 10/556,804, mailed May 12, 2010, 8 pages.
Response to Office Action for U.S. Appl. No. 10/556,804, filed Nov. 12, 2010, 12 pages.
Office Action in U.S. Appl. No. 10/556,804, mailed Feb. 1, 2011, 4 pages.
Response to Office Action for U.S. Appl. No. 10/556,804, filed Mar. 25, 2011, 9 pages.

(56) References Cited

OTHER PUBLICATIONS

Office Action in U.S. Appl. No. 10/562,843, mailed Nov. 12, 2008, 6 pages.
Response for U.S. Appl. No. 10/562,843, filed Feb. 24, 2009, 13 pages.
Office Action in U.S. Appl. No. 10/562,843, mailed Jun. 9, 2009, 5 pages.
Response for U.S. Appl. No. 10/562,843, filed Oct. 5, 2009, 10 pages.
Final Office Action for U.S. Appl. No. 10/562,843, mailed Feb. 3, 2010, 5 pages.
Office Action in U.S. Appl. No. 10/562,843, mailed Jul. 30, 2010, 7 pages.
Response for U.S. Appl. No. 10/562,843, filed Nov. 30, 2010, 8 pages.
Office Action in U.S. Appl. No. 10/562,843, mailed Feb. 16, 2011, 4 pages.
Response to Office Action in U.S. Appl. No. 10/562,843, filed Jun. 16, 2011, 9 pages.
Final Office Action in U.S. Appl. No. 10/562,843, filed Aug. 25, 2011, 5 pages.
Response to Final Office Action in U.S. Appl. No. 10/562,843, filed Nov. 21, 2011, 6 pages.
Office Action in U.S. Appl. No. 11/352,177, mailed Jun. 10, 2009, 14 pages.
Response for U.S. Appl. No. 11/352,177, filed Dec. 10, 2009, 20 pages.
Office Action in U.S. Appl. No. 11/352,177, mailed Apr. 14, 2010, 15 pages.
Response for U.S. Appl. No. 11/352,177, filed Oct. 14, 2010, 13 pages.
Supplemental Response for U.S. Appl. No. 11/352,177, filed Oct. 21, 2010, 15 pages.
Supplemental Response for U.S. Appl. No. 11/352,177, filed Dec. 6, 2010, 4 pages.
Final Office Action in U.S. Appl. No. 11/352,177, mailed Mar. 16, 2011, 18 pages.
Response to Final Office Action in U.S. Appl. No. 11/352,177, filed Sep. 16, 2011, 15 pages.
Office Action in U.S. Appl. No. 11/352,177, dated Jan. 30, 2014, 17 pages.
Response to Office Action in U.S. Appl. No. 11/352,177, dated May 28, 2014, 14 pages.
Office Action in U.S. Appl. No. 12/278,849, dated Oct. 10, 2012, 12 pages.
Response to Office Action in U.S. Appl. No. 12/278,849, dated Apr. 10, 2013, 19 pages.
Final Office Action in U.S. Appl. No. 12/278,849, dated Jun. 6, 2013, 24 pages.
Office Action in U.S. Appl. No. 12/278,849, dated Aug. 9, 2013, 22 pages.
Response to Office Action in U.S. Appl. No. 12/278,849, dated Jan. 9, 2014, 21 pages.
Office Action in U.S. Appl. No. 12/278,849 dated Mar. 17, 2014, 24 pages.
Office Action for U.S. Appl. No. 13/942,601, mailed Nov. 4, 2013, 16 pages.
Response to Office Action for U.S. Appl. No. 13/942,601, dated Feb. 4, 2014, 45 pages.
Office Action for AU 17165/01, mailed Jul. 13, 2004, 3 pages.
Office Action for CN 00818682.0, fax dated Feb. 4, 2005, 7 pages.
Office Action for IL 149885, dated Apr. 26, 2007, 4 pages.
Oxitec Nov. 2011 Newsletter, http://www.oxitec.com/our-news/newsletters/november-2011-newsletter/, downloaded Dec. 13, 2011, 6 pages.
Parker et al., "Functional interaction between nuclear inhibitor of protein phosphatase type 1 (NIPP1) and protein phosphatase type 1 (PP1) in *Drosophila*: consequences of over-expression of NIPP1 in flies and suppression by co-expression of PP1," Biochem J (2002) 368:789-797.
Phuc et al., "Late-acting dominant lethal genetic systems and mosquito control," BMC Biology (2007) 5:11, 11 pages.
Rejection for CN 00818682.0, fax dated Jan. 26, 2006, 4 pages.
Request for Further Processing for EP 00979774.7, filed Jan. 4, 2007, 4 pages.
Response to Communication pursuant to Article 96(2) EPC for EP 00979774.7, filed Feb. 13, 2006, 8 pages.
Response to Communication for EP 00979774.7, filed Apr. 14, 2005, 7 pages.
Response to Communication for EP 00979774.7, filed Sep. 20, 2004, 8 pages.
Restriction Requirement for U.S. Appl. No. 11/352,177, mailed Jan. 13, 2009, 10 pages.
Response to Restriction Requirement for U.S. Appl. No. 11/352,177, filed Mar. 13, 2009, 12 pages.
Restriction Requirement for U.S. Appl. No. 10/556,804, mailed May 28, 2009, 5 pages.
Response to Restriction Requirement for U.S. Appl. No. 10/556,804, filed Jun. 29, 2009, 2 pages.
Restriction Requirement for U.S. Appl. No. 10/562,843, mailed Jun. 12, 2008, 6 pages.
Response to Restriction Requirement for U.S. Appl. No. 10/562,843, filed Jun. 27, 2008, 2 pages.
Restriction Requirement for U.S. Appl. No. 11/352,177, mailed Mar. 31, 2008, 8 pages.
Response to Restriction Requirement for U.S. Appl. No. 11/352,177, filed Jun. 9, 2008, 9 pages.
Restriction Requirement for U.S. Appl. No. 11/352,177, mailed Sep. 2, 2008, 5 pages.
Response to Restriction Requirement for U.S. Appl. No. 11/352,177, filed Nov. 3, 2008, 8 pages.
Restriction Requirement for U.S. Appl. No. 12/278,849, mailed May 28, 2010, 7 pages.
Response to Restriction Requirement for U.S. Appl. No. 12/278,849, filed Sep. 28, 2010, 13 pages.
Ronaldson et al., "Two independent cis-acting elements regulate the sex- and tissue-specific expression of yp3 in *Drosophila melanogaster*," Genet Res. (1995) 66(1):9-17.
Second Office Action for AU 17165/01, mailed Mar. 21, 2006, 2 pages.
Second Office Action for CN 00818682.0, dated Jul. 28, 2006, 4 pages.
Simmons et al., "Field Performance of a Genetically Engineered Strain of Pink Bollworm," PLoS One (2011) 6(9):1-11.
Sondergaard et al., "Nutritional response in a *Drosophila* yolk protein gene promoter," Mol Gen Genet (1995) 248(1):25-32.
Spradling et al., "Transposition of cloned P elements into *Drosophila* germ line chromosomes," Science (1982) 218(4570):341-347.
Stadtfeld et al., "Without a trace? PiggyBac-ing toward pluripotency," Nat Methods (2009) 6(5):329-330.
Summary of Office Action for MX PA/a/2002/005337, mailed Jan. 3, 2007, 2 pages.
Van Eynde et al., "Molecular cloning of NIPP-1, a nuclear inhibitor of protein phosphatase-1, reveals homology with polypeptides involved in RNA processing," J Biol Chem (1995) 270(47):28068-28074.
Van Eynde et al., "Organization and alternate splice products of the gene encoding nuclear inhibitor of protein phosphatase-1 (NIPP-1)," Eur J Biochem (1999) 261(1):291-300.
Vulsteke et al., "Properties and phosphorylation sites of baculovirus-expressed nuclear inhibitor of protein phosphatase-1 (NIPP-1)," J Biol Chem (1997) 272(52):32972-32978.
Weinmann et al., "A chimeric transactivator allows tetracycline-responsive gene expression in whole plants," Plant J (1994) 5(4):559-569.
Wera et al., "Inhibition of translation by mRNA encoding NIPP-1, a nuclear inhibitor of protein phosphatase-1," Eur J Biochem (1997) 247(1):411-415.
Wharton et al., "CNS midline enhancers of the *Drosophila* slit and Toll genes," Mech Dev (1993) 40(3):141-154.
Wimmer, "Eco-friendly insect management," Nat Biotechnology (2005) 23(4):432-433.

(56) References Cited

OTHER PUBLICATIONS

Wise de Valdez et al., "Genetic elimination of dengue vector mosquitoes," Proc Natl Acad Sci USA (2011) 108(12):4772-4775.
Woltjen et al., "piggyBac transposition reprograms fibroblasts to induced pluripotent stem cells," Nature (2009) 458(7239):766-770.
Prosecution history for related U.S. Appl. No. 10/148,041, 64 pp., Dec. 22, 2010.
Prosecution history for related U.S. Appl. No. 11/733,737, 175 pp., Dec. 22, 2010.
Prosecution history for related U.S. Appl. No. 10/556,804, 27 pp., Dec. 14, 2010.
Prosecution history for related U.S. Appl. No. 11/352,177, 129 pp., Dec. 14, 2010.
Prosecution history for related U.S. Appl. No. 12/278,849, 20 pp., Dec. 14, 2010.
Prosecution history for related U.S. Appl. No. 10/562,843, 63 pp., Dec. 14, 2010.
Search Report corresponding to International Application No. PCT/GB2007/000488, parent of the present application, Dec. 14, 2010.
Written Opinion corresponding to International Application No. PCT/GB2007/000488, parent of the present application, Dec. 14, 2010.
International Preliminary Report on Patentability, corresponding to International Application No. PCT/GB2007/000488, parent of the present application.
Alphey et al. (2007) "Managing Insecticide Resistance by Mass Release of Engineered Insects" J. Econ. Entomol. 100(5):1642-1649.
Arribas et al. (1986) "The ubiquitin genes in *D. melanogaster*: transcription and polymorphism" Biochimica et Biophysica Acta 868:119-127.
Atkinson et al. (2000) "*Hermes* and Other *hAT* Elements as Gene Vectors in Insects," In; *Insect Transgenesis: Methods and Applications*, Hadler et al. eds., Boca Raton CRC Press, pp. 219-235.
Blitvich et al. (2002) "Developmental- and tissue-specific expression of an inhibitor of apoptosis protein 1 homologue from *Aedes triseriatus* mosquitoes" Insect Molecular Biology 11(5):431-442.
Cabera et al. (2002) "Expression Pattern of Gal4 Enhancer Trap Insertions Into the bric à brac Locus Generated by P Element Replacement," Genesis 34:62-65.
Carriere and Tabashnik (2001) "Reversing Insect Adaptation to Transgenic Insecticidal Plants," Proc. R. Soc. Lond. B. 268:1475-1480.
Chen et al. (1996) "Apoptotic Activity of REAPER Is Distict from Signaling by the Tumor Necrosis Factor Receptor 1 Death Domain" The Journal of Biological Chemistry 271(42):25735-25737.
Davis et al. (2001) "Engineered Underdominance Allows Efficient and Economical Introgression of Traits into Pest Populations," J. Theor. Biol. 212(1):83-98.
Elick et al. (1997) "Analysis of the Cis-Acting DNA Elements Required for piggyback Transposable Element Excision," Mol. Gen. Genet. 255:605-610.
Ernst, U. (1991) "Regulation of Sexual Differentiation in *Drosophila*: Alternative Splicing of the Transformer Primary Transcript Requires Masking of the Non-Specific Acceptor Site in Females," Inaugural Dissertation, Aus Frankfurt / Main, BRD.
Fu et al. (2007) "Female-specific insect lethality engineered using alternative splicing", Nature Biotechnology 25(3):353-357.
Funaguma et al. (2005) "The Bmdsx transgene including trimmed introns is sex-specifically spliced in tissues of the silkworm, *Bombyx mori*", Journal of Insect Science (online), 5(17):1-6.
Gloor et al. (1991) "Targeted Gene Replacement in *Drosophila* Via P Element-Induced Gap Repair," Science 253:1110-1117.
Gong et al. (2005) "A dominant lethal genetic system for autocidal control of the Mediterranean fruitfly", Nature Biotechnology 23(4):453-456.
Gonzy-Treboul et al. (1995) "Enhancer-Trap Targeting at the Broad-Complex Locus of *Drosophila melanogaster*," Genes Dev. 9:1137-1148.
Handler et al. (2001) "A Current Prospective on Insect Gene Transformation," Insect Biochem. Mol. Biol. 31(2):111-128.
Handler, A. (2002) "Use of piggyback Transposon for Germ-Line Transformation of Insects," Insect Biochem. Mol. Biol. 32:1211-1220.
Heslip et al. (1994) "Targeted Transposition at the *vestigial* Locus of *Drosophila melanogaster*," Genetics 138:1127-1135.
Hondred et al. (1999) "Use of Ubiquitin Fusions to Augment Protein Expression in Transgenic Plants" Plant Physiology 119:713-723.
Horn et al. (2003) "piggyBac-Based Insertional Metagenesis and Enhancer Detection as a Tool for Functional Insect Genomics," Genetics 163(2):647-661.
Horn et al. (2002) "Fluorescent Transformation Markers for Insect Transgenesis," Insect Biochem. Mol. Biol. 32:1221-1235.
Imai, C. (1987) "Control of Insecticide Resistance in a Field Population of Houseflies, *Musca domestica*, by Releasing Susceptible Flies," Res. Popul. Ecol. 29:129-146.
Johnson-Schlitz et al. (1993) "P-Element-Induced Interallelic Gene Conversion of Insertions and Deletions in *Drosophila melanogaster*," Mol Cell Biol. 13:7006-7018.
Lankenau et al. (1996) "Comparison of Targeted-Gene Replacement Frequencies in *Drosophila melanogaster* at the Forked and White Loci," Mol. Cell Biol. 16:3535-3544.
Munoz et al. (2004) "The AeAct-4 gene is expressed in the developing flight muscles of female *Aedes aegypti*", Insect Molecular Biology 13(5):563-568.
piggyBac website, http://piggybac.bio.nd.edu/, Mar. 21, 2006, 5 pp.
Robinson et al. (2002) "Mutations and Their Use in Insect Control," Mutation Research 511(2):113-132.
Rong et al. (2000) "Gene Targeting by Homologous Recombination in *Drosophila*," Science 288:2013-2018.
Rong et al. (2001) "A Targeted Gene Knockout in *Drosophila*," Genetics 157:1307-1312.
Russ et al. (1996) "Self-Deleting Retrovirus Vectors for Gene Therapy," J. Virol. 70:4927-4932.
Saccone et al. (2002) "Sex determination in flies, fruitflies and butterflies" Genetica 116:15-23.
Scali et al. (2005) "Identification of sex-specific transcripts of the *Anopheles gambiae* doublesex gene", Journal of Experimental Biology 208(19):3701-3709.
Sepp et al. (1999) "Conversion of *lacZ* Enhanced Trap Lines to *GAL4* Lines Using Targeted Transposition in *Drosophila melanogaster*," Genetics 151:1093-1101.
Shelton et al. (2000) "Field Tests on Managing Resistance to *Bt*-Engineered Plants", Nature Biotechnology 18(3):339-342.
Steiner et al. (1995) "Homologous Recombination as the Main Mechanism for DNA Integration and Cause of Rearrangements in the Filamentous Ascomycete *Ashbya gossypii*," Genetics 140:973-987.
Wobus et al. (1990) "A New Transposable Element in *Chironomus thummi*," Mol. General Genet. 222:311-316.
Wool and Manheim (1980) "Genetically-Induced Susceptibility to Malathion in *Tribolium castaneum* Despite Selection for Resistance," Ent. Exp. & Appl. 28:183-190.
Further Search Report for GB 9928181.8, mailed Apr. 30, 2001.
Communication pursuant to Article 94(3) EPC for EP 07 712 717.3, mailed Jul. 11, 2014, 8 pages.
Alignment of SEQ ID No:22 of D1 (WO 2005/012534) with tTAV, Jul. 4, 2014.
Restriction Requirement for U.S. Appl. No. 10/148,041, mailed Mar. 10, 2005, 5 pages.
Response to Restriction Requirement for U.S. Appl. No. 10/148,041, filed Apr. 13, 2005, 10 pages.
Office Action for U.S. Appl. No. 10/148,041, mailed Jul. 1, 2005, 14 pages.
Response to Office Action for U.S. Appl. No. 10/148,041, filed Dec. 5, 2005, 11 pages.
Final Office Action for U.S. Appl. No. 10/148,041, mailed Mar. 7, 2006, 9 pages.
Request for Continued Examination for U.S. Appl. No. 10/148,041, filed Sep. 11, 2006, 8 pages.
Office Action for U.S. Appl. No. 10/148,041, mailed Oct. 10, 2006, 8 pages.
Office Action for U.S. Appl. No. 11/733,737, mailed Apr. 10, 2008, 8 pages.

(56) References Cited

OTHER PUBLICATIONS

Response to Office Action for U.S. Appl. No. 11/733,737, filed Oct. 10, 2008, 8 pages.
Restriction Requirement for U.S. Appl. No. 11/733,737, mailed Dec. 31, 2008, 9 pages.
Response to Restriction Requirement for U.S. Appl. No. 11/733,737, filed Jan. 26, 2009, 8 pages.
Final Office Action for U.S. Appl. No. 11/733,737, mailed Apr. 17, 2009, 16 pages.
Response to Final Office Action for U.S. Appl. No. 11/733,737, filed Jul. 17, 2009, 26 pages.
Advisory Action for U.S. Appl. No. 11/733,737, mailed Aug. 5, 2009, 4 pages.
Request for Continued Examination for U.S. Appl. No. 11/733,737, filed Aug. 14, 2009, 1 page.
Office Action for U.S. Appl. No. 11/733,737, mailed Oct. 1, 2009, 21 pages.
Response to Office Action for U.S. Appl. No. 11/733,737, filed Jan. 29, 2010, 23 pages.
Final Office Action for U.S. Appl. No. 11/733,737, mailed Aug. 4, 2010, 18 pages.
Response to Final Office Action for U.S. Appl. No. 11/733,737, filed Dec. 6, 2010, 26 pages.
Office Action for U.S. Appl. No. 11/733,737, mailed Feb. 8, 2011, 6 pages.
Response to Office Action for U.S. Appl. No. 11/733,737, filed Feb. 18, 2011, 11 pages.
Office Action for U.S. Appl. No. 11/733,737, mailed Jun. 28, 2011, 14 pages.
Response to Office Action for U.S. Appl. No. 11/733,737, filed Oct. 28, 2011, 27 pages.
Office Action for U.S. Appl. No. 11/733,737, mailed Mar. 27, 2012, 17 pages.
Response to Office Action for U.S. Appl. No. 11/733,737, filed Aug. 9, 2012, 24 pages.
Final Office Action for U.S. Appl. No. 11/733,737, mailed Jan. 7, 2013, 26 pages.
Response to Final Office Action for U.S. Appl. No. 11/733,737, filed Apr. 8, 2013, 25 pages.
Advisory Action for U.S. Appl. No. 11/733,737, mailed Jun. 3, 2013, 7 pages.
Notice of Appeal for U.S. Appl. No. 11/733,737, filed Jul. 3, 2013, 1 page.
Appeal Brief for U.S. Appl. No. 11/733,737, filed Feb. 3, 2014, 40 pages.
Examiner's Answer to Appeal Brief for U.S. Appl. No. 11/733/737, mailed Jul. 18, 2014, 12 pages.
Reply Brief and Request for Oral Hearing for U.S. Appl. No. 11/733,737, filed Sep. 18, 2014, 16 pages.
Final Office Action for U.S. Appl. No. 13/942,601, mailed Jul. 31, 2014, 23 pages.
Notice of Appeal for U.S. Appl. No. 13/942,601, filed Feb. 2, 2015, 1 page.
Notice of Allowance for U.S. Appl. No. 13/942,601, mailed Apr. 10, 2015, 11 pages.
Notice of Appeal for U.S. Appl. No. 12/278,849, filed Jun. 17, 2014, 1 page.
Appeal Brief for U.S. Appl. No. 12/278,849, filed Oct. 16, 2014, 31 pages.
Office Action for U.S. Appl. No. 12/278,849, mailed Dec. 5, 2014, 15 pages.
Office Action for U.S. Appl. No. 12/278,849, mailed Mar. 10, 2015, 18 pages.
International Preliminary Examination Report for PCT/GB00/04541, mailed Apr. 4, 2002, 2 pages.
Written Opinion for PCT/GB2004/002021, received Oct. 4, 2004, 5 pages.
International Search Report for PCT/GB2004/002021, mailed Oct. 6, 2004, 3 pages.
International Preliminary Report on Patentability for PCT/GB2004/002021, issued Nov. 18, 2005, 6 pages.
International Search Report for PCT/GB2004/002869, mailed Jan. 11, 2005, 5 pages.
Written Opinion for PCT/GB2004/002869, received Jan. 12, 2005, 8 pages.
International Preliminary Report on Patentability for PCT/GB2004/002869, issued Jan. 3, 2006, 9 pages.
Written Opinion for PCT/GB2004/003263, received Nov. 5, 2004, 5 pages.
International Preliminary Report on Patentability for PCT/GB2004/003263, issued Jan. 30, 2006, 6 pages.
Final Office Action for U.S. Appl. No. 11/352,177, mailed Oct. 14, 2014, 6 pages.
Response to Final Office Action for U.S. Appl. No. 11/352,177, filed Dec. 3, 2014, 8 pages.
Notice of Allowance for U.S. Appl. No. 11/352,177, mailed Mar. 17, 2015, 10 pages.

* cited by examiner tetO₇   minimal          tTA coding region
        promoter
                  other control signals not marked, e.g.
                  5'UTR, 3'UTR, intron(s), polyA Heterologous    minimal    tetO₇  minimal   tTA coding region
   gene        promoter            promoter
                  B                   A Diagram of $tetO_7$-tTA region of pJY2004

Potential PCR products generated:

1. If intron is not excised → ~1550 bp
2. If intron is spliced in male form (M1 or M2)→ ~600 bp
3. If intron is spliced in female form → ~200 bp

SEQUENCE LISTING

```
<160> NUMBER OF SEQ ID NOS: 33

<210> SEQ ID NO 1
<211> LENGTH: 44
<212> TYPE: DNA
<213> ORGANISM: Drosophila sp.

<400> SEQUENCE: 1

cacagcgcat gatgagcaca ttaacaaaat gtagtaaaat agga                        44


<210> SEQ ID NO 2
<211> LENGTH: 44
<212> TYPE: DNA
<213> ORGANISM: Drosophila sp.

<400> SEQUENCE: 2

gtttcgataa atattgctat ttaaaatgct tattttcaat gcta                        44


<210> SEQ ID NO 3
<211> LENGTH: 44
<212> TYPE: DNA
<213> ORGANISM: Drosophila sp.

<400> SEQUENCE: 3

tttgttttct aacgttaaag ttaaagagag tccagccaca tttt                        44


<210> SEQ ID NO 4
<211> LENGTH: 21
<212> TYPE: DNA
<213> ORGANISM: Artificial
<220> FEATURE:
<223> OTHER INFORMATION: PCR Primer

<400> SEQUENCE: 4

acgcgagagg tgaaattctt g                                                 21


<210> SEQ ID NO 5
<211> LENGTH: 23
<212> TYPE: DNA
<213> ORGANISM: Artificial
<220> FEATURE:
<223> OTHER INFORMATION: PCR Primer

<400> SEQUENCE: 5

gaaaacatct ttggcaaatg ctt                                               23


<210> SEQ ID NO 6
<211> LENGTH: 16
<212> TYPE: DNA
<213> ORGANISM: Artificial
<220> FEATURE:
<223> OTHER INFORMATION: Nucleotide portion of TaqMan MGB probe

<400> SEQUENCE: 6

ccgtcgtaag actaac                                                       16


<210> SEQ ID NO 7
<211> LENGTH: 17
```

<212> TYPE: DNA
<213> ORGANISM: Artificial
<220> FEATURE:
<223> OTHER INFORMATION: PCR Primer

<400> SEQUENCE: 7
catgccgacg cgctaga 17

<210> SEQ ID NO 8
<211> LENGTH: 26
<212> TYPE: DNA
<213> ORGANISM: Artificial
<220> FEATURE:
<223> OTHER INFORMATION: PCR Primer

<400> SEQUENCE: 8
gtaaacatct gctcaaactc gaagtc 26

<210> SEQ ID NO 9
<211> LENGTH: 18
<212> TYPE: DNA
<213> ORGANISM: Artificial
<220> FEATURE:
<223> OTHER INFORMATION: Nucleotide portion of TaqMan MGB probe

<400> SEQUENCE: 9
tcgatctgga catgttgg 18

<210> SEQ ID NO 10
<211> LENGTH: 25
<212> TYPE: DNA
<213> ORGANISM: Artificial
<220> FEATURE:
<223> OTHER INFORMATION: PCR Primer

<400> SEQUENCE: 10
gccctcgatg gtagacccgt aattg 25

<210> SEQ ID NO 11
<211> LENGTH: 27
<212> TYPE: DNA
<213> ORGANISM: Artificial
<220> FEATURE:
<223> OTHER INFORMATION: PCR Primer

<400> SEQUENCE: 11
gctaaacaat ctgcaggtac cctggcg 27

<210> SEQ ID NO 12
<211> LENGTH: 20
<212> TYPE: DNA
<213> ORGANISM: Artificial
<220> FEATURE:
<223> OTHER INFORMATION: PCR Primer

<400> SEQUENCE: 12
cctgccagga ctcgccttcc 20

<210> SEQ ID NO 13
<211> LENGTH: 22
<212> TYPE: DNA
<213> ORGANISM: Artificial
<220> FEATURE:
<223> OTHER INFORMATION: PCR Primer

<400> SEQUENCE: 13

-continued

```
gtcatcaact ccgcgttgga gc                                             22


<210> SEQ ID NO 14
<211> LENGTH: 2556
<212> TYPE: DNA
<213> ORGANISM: Artificial
<220> FEATURE:
<223> OTHER INFORMATION: JY2004-tTA

<400> SEQUENCE: 14

gcggccgcat agtcgacatt tcgagtttac cactccctat cagtgataga gaaaagtgaa     60

agtcgagttt accactccct atcagtgata gagaaaagtg aaagtcgagt ttaccactcc    120

ctatcagtga tagagaaaag tgaaagtcga gtttaccact ccctatcagt gatagagaaa    180

agtgaaagtc gagtttacca ctccctatca gtgatagaga aaagtgaaag tcgagtttac    240

cactccctat cagtgataga gaaaagtgaa agtcgagttt accactccct atcagtgata    300

gagaaaagtg aaagtcgagc tcggtacccg ggtcgaggta ggcgtgtacg gtgggaggcc    360

tatataagca gagctcgttt agtgaaccgt cagatcgcct ggagacgcca tccacgctgt    420

tttgacctcc atagaagaca ccgggaccga tccagcctcc gcggccccga attcgagctc    480

ggtacccggg gatccccgct cgagctgaat agggaattgg gaattggagc agaggtgggt    540

tcttcgcatt acactgttcg ccacaatctt gtttattcat tcgccttgca ggttgccacc    600

atggaattga gattagataa aagtaaagtg attaacagcg cattagagct gcttaatgag    660

gtcggaatcg aaggtttaac aacccgtaaa ctcgcccaga agctaggtgt agagcagcct    720

acattgtatt ggcatgtaaa aaataagcgg gctttgctcg acgccttagc cattgagatg    780

ttagataggc accatactca cttttgccct ttagaagggg aaagctggca agatttttta    840

cgtaataacg ctaaaagttt tagatgtgct ttactaagtc atcgcgatgg agcaaaagta    900

catttaggta cacggcctac agaaaaacag tatgaaactc tcgaaaatca attagccttt    960

ttatgccaac aaggtttttc actagagaat gcattatatg cactcagcgc tgtggggcat   1020

tttactttag gttgcgtatt ggaagatcaa gagcatcaag tcgctaaaga agaaagggaa   1080

acacctacta ctgatagtat gccgccatta ttacgacaag ctatcgaatt atttgatcac   1140

caaggtgcag agccagcctt cttattcggc cttgaattga tcatatgcgg attagaaaaa   1200

caacttaaat gtgaaagtgg gtccgcgtac agccgcgcgc gtacgaaaaa caattacggg   1260

tctaccatcg agggcctgct cgatctcccg gacgacgacg cccccgaaga ggcggggctg   1320

gcggctccgc gcctgtcctt tctccccgcg ggacacacgc gcagactgtc gacggccccc   1380

ccgaccgatg tcagcctggg ggacgagctc cacttagacg gcgaggacgt ggcgatggcg   1440

catgccgacg cgctagacga tttcgatctg gacatgttgg gggacgggga ttccccgggt   1500

ccgggattta ccccccacga ctccgccccc tacggcgctc tggatatggc cgacttcgag   1560

tttgagcaga tgtttaccga tgcccttgga attgacgagt acggtgggta gtgaaacgcg   1620

tctagagctg agaacttcag ggtgagtttg gggacccttg attgttcttt ctttttcgct   1680

attgtaaaat tcatgttata tggagggggc aaagttttca gggtgttgtt tagaatggga   1740

agatgtccct tgtatcacca tggaccctca tgataatttt gtttctttca ctttctactc   1800

tgttgacaac cattgtctcc tcttattttc ttttcatttt ctgtaacttt ttcgttaaac   1860

tttagcttgc atttgtaacg aatttttaaa ttcacttttg tttatttgtc agattgtaag   1920

tactttctct aatcactttt ttttcaaggc aatcagggta tattatattg tacttcagca   1980

cagttttaga gaacaattgt tataattaaa tgataaggta gaatatttct gcatataaat   2040
```

tctggctggc gtggaaatat tcttattggt agaaacaact acaccctggt catcatcctg 2100
cctttctctt tatggttaca atgatataca ctgtttgaga tgaggataaa atactctgag 2160
tccaaaccgg gcccctctgc taaccatgtt catgccttct tctctttcct acagctcctg 2220
ggcaacgtgc tggttgttgt gctgtctcat cattttggca aagaattcac tcctcaggtg 2280
caggctgcct atcagaaggt ggtggctggt gtggccaatg ccctggctca caaataccac 2340
tgagatcttt ttccctctgc caaaaattat ggggacatca tgaagcccct tgagcatctg 2400
acttctggct aataaaggaa atttattttc attgcaatag tgtgttggaa tttttgtgt 2460 ctctcactcg gaaggacata tgggagggca aatcatttaa aacatcagaa tgagtatttg 2520
gtttagagtt tggcaacata tgcccatagc ggccgc 2556

<210> SEQ ID NO 15
<211> LENGTH: 12087
<212> TYPE: DNA
<213> ORGANISM: Artificial
<220> FEATURE:
<223> OTHER INFORMATION: pP[Casper-Act5C-tTA]

<400> SEQUENCE: 15
gatccatgag caattagcat gaacgttctg aaaagcgcgt ttagctctcc actacttaca 60
catattctat gctgcaatat tgaaaatcta ataaacaaaa ctaatgtaca ttaattcttc 120
agttttgaat atccttctcc tgactttctt atttagaatt aatataatac tgcatacatt 180
aatactgtaa atatgataag tacctgcaaa acactgcagc tcaagtctta atgaggttct 240
gcgatagctt agcataatta gtaacttatc gcgcagaatt ccctaatgtt cccgacctac 300
atgtacttct gatagttgcc gaggtcaaat gttgttgtat ttgtattata cctcaatatt 360
ggtatattca atatctaata gtacccaatt caattgcaaa gatagtcatt aaaaaaacct 420
aaatcacttg caaattgact tttctgccgg aaaagcaacc ttgacacaca aagttaatta 480
gtttatctgg aagtcatgtg agaaatttgt aaataaaatt tttcgcagta atttaagtgg 540
gcctaatccc ttttaagcat cttggtttta cgatgacacc gcaataaggt acaactttat 600
attgtttttg caatcagctt gagtctttat taggcatcag tctttctctc taagtttctt 660
cgtgcaataa atgaggttcc aaactccgta gatttttcct tctttgttga atccagatcc 720
tgcaaagaaa aaagagcaaa cccctaggtc tgtccaggaa tgtattttcg tgtttgtcga 780
tcgaccatgg tctcgagagg ccttgcagcc aagctttgcg tactcgcaaa ttattaaaaa 840
taaaacttta aaaataattt cgtctaatta atattatgag ttaattcaaa ccccacggac 900
atgctaaggg ttaatcaaca atcatatcgc tgtctcactc agactcaata cgacactcag 960
aatactattc ctttcactcg cacttattgc aagcatacgt taagtggatg tctcttgccg 1020
acgggaccac cttatgttat ttcatcatgg tctggccatt ctcatcgtga gcttccgggt 1080
gctcgcatat ctggctctaa gacttcgggc ccgacgcaag gagtagccga catatatccg 1140
aaataactgc ttgttttttt ttttaccatt attaccatcg tgtttactgt ttattgcccc 1200
ctcaaaaagc taatgtaatt atatttgtgc caataaaaac aagatatgac ctatagaata 1260
caagtatttc cccttcgaac atccccacaa gtagactttg gatttgtctt ctaaccaaaa 1320
gacttacaca cctgcatacc ttacatcaaa aactcgttta tcgctacata aaacaccggg 1380
atatattttt tatatacata cttttcaaat cgcgcgccct cttcataatt cacctccacc 1440
acaccacgtt tcgtagttgc tctttcgctg tctcccaccc gctctccgca acacattcac 1500

-continued

```
cttttgttcg acgaccttgg agcgactgtc gttagttccg cgcgattcgg tgcggtattt   1560
cacaccgcat atggtgcact ctcagtacaa tctgctctga tgccgcatag ttaagccagc   1620
cccgacaccc gccaacaccc gctgacgcgc cctgacgggc ttgtctgctc ccggcatccg   1680
cttacagaca agctgtgacc gtctccggga gctgcatgtg tcagaggttt tcaccgtcat   1740
caccgaaacg cgcgagacga aagggcctcg tgatacgcct atttttatag gttaatgtca   1800
tgataataat ggtttcttag acgtcaggtg gcacttttcg gggaaatgtg cgcggaaccc   1860
ctatttgttt atttttctaa atacattcaa atatgtatcc gctcatgaga caataaccct   1920
gataaatgct tcaataatat tgaaaaagga agagtatgag tattcaacat ttccgtgtcg   1980
cccttattcc cttttttgcg gcattttgcc ttcctgtttt tgctcaccca gaaacgctgg   2040
tgaaagtaaa agatgctgaa gatcagttgg gtgcacgagt gggttacatc gaactggatc   2100
tcaacagcgg taagatcctt gagagttttc gccccgaaga acgttttcca atgatgagca   2160
cttttaaagt tctgctatgt ggcgcggtat tatcccgtat tgacgccggg caagagcaac   2220
tcggtcgccg catacactat tctcagaatg acttggttga gtactcacca gtcacagaaa   2280
agcatcttac ggatggcatg acagtaagag aattatgcag tgctgccata accatgagtg   2340
ataacactgc ggccaactta cttctgacaa cgatcggagg accgaaggag ctaaccgctt   2400
ttttgcacaa catgggggat catgtaactc gccttgatcg ttgggaaccg gagctgaatg   2460
aagccatacc aaacgacgag cgtgacacca cgatgcctgt agcaatggca acaacgttgc   2520
gcaaactatt aactggcgaa ctacttactc tagcttcccg gcaacaatta atagactgga   2580
tggaggcgga taaagttgca ggaccacttc tgcgctcggc ccttccggct ggctggttta   2640
ttgctgataa atctggagcc ggtgagcgtg ggtctcgcgg tatcattgca gcactggggc   2700
cagatggtaa gccctcccgt atcgtagtta tctacacgac ggggagtcag gcaactatgg   2760
atgaacgaaa tagacagatc gctgagatag gtgcctcact gattaagcat tggtaactgt   2820
cagaccaagt ttactcatat atactttaga ttgatttaaa acttcatttt taatttaaaa   2880
ggatctaggt gaagatcctt tttgataatc tcatgaccaa aatcccttaa cgtgagtttt   2940
cgttccactg agcgtcagac cccgtagaaa agatcaaagg atcttcttga gatccttttt   3000
ttctgcgcgt aatctgctgc ttgcaaacaa aaaaaccacc gctaccagcg gtggtttgtt   3060
tgccggatca agagctacca actctttttc cgaaggtaac tggcttcagc agagcgcaga   3120
taccaaatac tgtccttcta gtgtagccgt agttaggcca ccacttcaag aactctgtag   3180
caccgcctac atacctcgct ctgctaatcc tgttaccagt ggctgctgcc agtggcgata   3240
agtcgtgtct taccgggttg gactcaagac gatagttacc ggataaggcg cagcggtcgg   3300
gctgaacggg gggttcgtgc acacagccca gcttggagcg aacgacctac accgaactga   3360
gatacctaca gcgtgagcta tgagaaagcg ccacgcttcc cgaagggaga aaggcggaca   3420
ggtatccggt aagcggcagg gtcggaacag gagagcgcac gagggagctt ccagggggaa   3480
acgcctggta tctttatagt cctgtcgggt ttcgccacct ctgacttgag cgtcgatttt   3540
tgtgatgctc gtcagggggg cggagcctat ggaaaaacgc cttcttcttg aactcgggct   3600
cggtgccagt atacctcaaa tggttgtcgt acctctcatg gttccgttac gccaacgagg   3660
gtctgctgat taaccaatgg gcggacgtgg agccgggcga aattagctgc acatcgtcga   3720
acaccacgtg ccccagttcg ggcaaggtca tcctggagac gcttaacttc tccgccgccg   3780
atctgccgct ggactacgtg ggtctggccc atgatgaaat aacataaggt ggtcccgtcg   3840
aaagccgaag cttaccgaag tatacactta aattcagtgc acgtttgctt gttgagagga   3900
```

-continued

```
aaggttgtgt gcggacgaat ttttttttga aaacattaac ccttacgtgg aataaaaaaa   3960
aatgaaatat tgcaaatttt gctgcaaagc tgtgactgga gtaaaattaa ttcacgtgcc   4020
gaagtgtgct attaagagaa aattgtggga gcagagcctt gggtgcagcc ttggtgaaaa   4080
ctcccaaatt tgtgataccc actttaatga ttcgcagtgg aaggctgcac ctgcaaaagg   4140
tcagacattt aaaaggaggc gactcaacgc agatgccgta cctagtaaag tgatagagcc   4200
tgaaccagaa aagataaaag aaggctatac cagtgggagt acacaaacag agtaagtttg   4260
aatagtaaaa aaaatcattt atgtaaacaa taacgtgact gtgcgttagg tcctgttcat   4320
tgtttaatga aaataagagc ttgagggaaa aaattcgtac tttggagtac gaaatgcgtc   4380
gtttagagca gcagccgaat taattctagt tccagtgaaa tccaagcatt ttctaaatta   4440
aatgtattct tattattata gttgttattt ttgatatata taaacaacac tattatgccc   4500
accatttttt tgagatgcat ctacacaagg aacaaacact ggatgtcact ttcagttcaa   4560
attgtaacgc taatcactcc gaacaggtca caaaaaatta ccttaaaaag tcataatatt   4620
aaattagaat aaatatagct gtgagggaaa tatatacaaa tatattggag caaataaatt   4680
gtacatacaa atatttatta ctaatttcta ttgagacgaa atgaaccact cggaaccatt   4740
tgagcgaacc gaatcgcgcg gaactaacga cagtcgctcc aaggtcgtcg aacaaaaggt   4800
gaatgtgttg cggagagcgg gtgggagaca gcgaaagagc aactacgaaa cgtggtgtgg   4860
tggaggtgaa ttatgaagag ggcgcgcgat ttgaaaagta tgtatataaa aaatatatcc   4920
cggtgtttta tgtagcgata aacgagtttt tgatgtaagg tatgcaggtg tgtaagtctt   4980
ttggttagaa gacaaatcca aagtctactt gtggggatgt tcgaagggga aatacttgta   5040
ttctataggt catatcttgt ttttattggc acaaatataa ttacattagc tttttgaggg   5100
ggcaataaac agtaaacacg atggtaataa tggtaaaaaa aaaaaacaag cagttatttc   5160
ggatatatgt cggctactcc ttgcgtcggg cccgaagtct tagagccaga tatgcgagca   5220
cccggaagct cacgatgaga atggccagac ccacgtagtc cagcggcaga tcggcggcgg   5280
agaagttaag cgtctccagg atgaccttgc ccgaactggg gcacgtggtg ttcgacgatg   5340
tgcagctaat ttcgcccggc tccacgtccg cccattggtt aatcagcaga ccctcgttgg   5400
cgtaacggaa ccatgagagg tacgacaacc atttgaggta tactggcacc gagcccgagt   5460
tcaagaagaa gccgccaaag agcaggaatg gtatgataac cggcggaccc acagacagcg   5520
ccatcgaggt cgaggagctg gcgcaggata ttagatatcc gaaggacgtt gacacattgg   5580
ccaccagagt gaccagcgcc aggcagttga agaagtgcag cactccggcc cgcagtccga   5640
tcatcggata ggcaatcgcc gtgaagacca gtggcactgt gagaaaaagc ggcaattcgg   5700
caatcgtttt gcccagaaag tatgtgtcac agcgataaag tcgacttcgg gcctccctca   5760
taaaaactgg cagctctgag gtgaacacct aaatcgaatc gattcattag aaagttagta   5820
aattattgaa atgcaaatgt attctaaaca tgacttacat ttatcgtggc aaagacgttt   5880
tgaaaggtca tgttggtcag gaagaggaag atggctccgt tgatattcat cacacccact   5940
tgcgtgagtt gttggcccaa aaagatgagg ccaatcaaga tggcaaccat ctgcaaatta   6000
aaatgttact cgcatctcat taatattcgc gagttaaatg aaatttattt atcttctgca   6060
aaactataaa ctatacatct cattgaaaaa aactaagaag ggtgtggaat caggcaattc   6120
tatctaaaat ctagcgaatt tgtttccaag aattgtaagc gttatatcat ttgtttccac   6180
tggaaccact caccgttgtc tgaataagtc gcacttttac gaggagtggt tccttgagca   6240
```

-continued

```
ccgacagcca ggatcgccac aggaccgccc ggaactgcat gaaccaggtg gccttgtagg   6300
tgtacccatt ctccggctgc tccagtggct tctccagatt tttggtggcc aacaactgct   6360
ccatatcccg ggctactttg ctaatggcaa aattgtcgcc atatcttggc gatccgatca   6420
cgggactcga tctcccgtcc gggcacaacg gccaacacct gtacgtaaaa gtccgccgga   6480
ttgtagttgg taggacactg ggcacccacg ctggatagga gttgagatgt aatgtaatgc   6540
tagataccct taataaacac atcgaactca ctaggaaaag aagtcgacgg cttcgctggg   6600
agtgcccaag aaagctaccc tgccctcggc catcagaagg atcttgtcaa agagctcaaa   6660
cagctcggaa gacggctgat gaatggtcag gatgacggtc ttgcccttct gcgacagctt   6720
cttcagcacc tggacgacgc tgtgggcggt aaatgagtcc agtccggagg tgggctcatc   6780
gcagatcaga agcggcggat cggttagtgc ctcggaggcg aatgccagac gcttcctttc   6840
tccgccggac agacctttca ccctgccggg cacaccgatg atcgtgtgct gacatttgct   6900
gagcgaaagc tcctggatca cctgatccac gcgggccact cgctgccgat aggtcagatg   6960
tcgtggcatc cgcaccatgg cttggaaaat caggtgttcc ctggccgtta gggagccgat   7020
aaagaggtca tcctgctgga cataggcgca cctggcctgc atctccttgg cgtccacagg   7080
ttggccattg agcagtcgca tcccggatgg cgatacttgg atgccctgcg gcgatcgaaa   7140
ggcaagggca ttcagcaggg tcgtctttcc ggcaccggaa ctgcccatca cggccaaaag   7200
ttcgcccgga taggccacgc cgcaaactga gtttcaaatt ggtaattgga ccctttatta   7260
agatttcaca cagatcagcc gactgcgaat agaaactcac cgttcttgag caaatgtttc   7320
ctgggcgccg gtatgtgtcg ctcgttgcag aatagtccgc gtgtccggtt gaccagctgc   7380
cgccatccgg agcccggctg attgaccgcc ccaaagatgt ccatattgtg ccaggcatag   7440
gtgaggttct cggctagttg gccgctccct gaaccggagt cctccggcgg actgggtggc   7500
aggagcgtgc cgtagttttt ggcctgcccg aagccctggt taatgcagct ctgcgaagcg   7560
tccgctgtca ccctgcaatg ataggggatc tcaaatatca actacaagcg ttatgctcat   7620
ctaaccccga acaaaacgaa gtatcctacg aagtaggttt atacttttat ttatttttg    7680
tgcatagctt aaaatatctg gttgttatat tttttgtaaa aaagaatgta gtcgaaaatg   7740
aatgccttta gatgtcttga tcatgatatg atcttaaaaa ttgtcttata tagcgagcac   7800
agctaccaga ataatctgtt tcgtgtcact atttgtttgt gcgattgcgg tttgggattt   7860
ttgtgggtcg cagttctcac gccgcagaca atttgatgtt gcaatcgcag ttcctataga   7920
tcaagtgaac ttaagatgta tgcacatgta ctactcacat tgttcagatg ctcggcagat   7980
gggtgtttgc tgcctccgcg aattaatagc tcctgatcct cttggcccat tgccgggatt   8040
tttcacactt tcccctgctt acccacccaa aaccaatcac caccccaatc actcaaaaaa   8100
caaacaaaaa taagaagcga gaggagtttt ggcacagcac tttgtgttta attgatggcg   8160
taaaccgctt ggagcttcgt cacgaaaccg ctgacaaagt gcaactgaag gcggacattg   8220
acgctaggta acgctacaaa cggtggcgaa agagatagcg gacgcagcgg cgaaagagac   8280
ggcgatattt ctgtggacag agaaggaggc aaacagcgct gactttgagt ggaatgtcat   8340
tttgagtgag aggtaatcga aagaacctgg tacatcaaat acccttggat cgaagtaaat   8400
ttaaaactga tcagataagt tcaatgatat ccagtgcagt aaaaaaaaaa aatgtttttt   8460
ttatctactt tccgcaaaaa tgggttttat taacttacat acatactaga attctaaaaa   8520
aaatcatgaa tggcatcaac tctgaatcaa atctttgcag atgcacctac ttctcatttc   8580
cactgtcaca tcatttttcc agatctcgct gcctgttatg tggcccacaa accaagacac   8640
```

-continued

```
gttttatggc cattaaagct ggctgatcgt cgccaaacac caaatacata tcaatatgta   8700
cattcgagaa agaagcgatc aaagaagcgt cttcgggcga gtaggagaat gcggaggaga   8760
aggagaacga gctgatctag tatctctcca caatccaatg ccaactgacc aactggccat   8820
attcggagca atttgaagcc aatttccatc gcctggcgat cgctccattc ttggctatat   8880
gtttttcacc gttcccgggg ccattttcaa agactcgtcg gtaagataag attgtgtcac   8940
tcgctgtctc tcttcatttg tcgaagaatg ctgaggaatt tcgcgatgac gtcggcgagt   9000
attttgaaga atgagaataa tttgtattta tacgaaaatc agttagtgga attttctaca   9060
aaaacatgtt atctatagat aattttgttg caaaatatgt tgactatgac aaagattgta   9120
tgtatatacc tttaatgtat tctcattttc ttatgtattt ataatggcaa tgatgatact   9180
gatgatattt taagatgatg ccagaccaca ggctgatttc tgcgtctttt gccgaacgca   9240
gtgcatgtgc ggttgttgtt ttttggaata gtttcaattt tcggactgtc cgctttgatt   9300
tcagtttctt ggcttattca aaaagcaaag taaagccaaa aaagcgagat ggcaatacca   9360
aatgcggcaa aacggtagtg gaaggaaagg ggtgcggggc agcggaagga agggtggggc   9420
ggggcgtggc ggggtctgtg gctgggcgcg acgtcaccga cgttggagcc actcctttga   9480
ccatgtgtgc gtgtgtgtat tattcgtgtc tcgccactcg ccggttgttt ttttcttttt   9540
atctcgctct ctctagcgcc atctcgtacg catgctcaac gcaccgcatg ttgccgtgtc   9600
ctttatgcgt cattttggct cgaaataggc aattatttaa acaaagatta gtcaacgaaa   9660
acgctaaaat aaataagtct acaatatggt tacttattgc catgtgtgtg cagccaacga   9720
tagcaacaaa agcaacaaca cagtggcttt ccctctttca ctttttgttt gcaagcgcgt   9780
gcgagcaaga cggcacgacc ggcaaacgca attacgctga caaagagcag acgaagtttt   9840
ggccgaaaaa catcaaggcg cctgatacga atgcatttgc aataacaatt gcgatattta   9900
atattgttta tgaagctgtt tgacttcaaa acacacaaaa aaaaaaataa aacaaattat   9960
ttgaaagaga attaggaatc ggacagctta tcgttacggg ctaacagcac accgagacga  10020
aatagcttac ctgacgtcac agcctctgga agaactgccg ccaagcagac gatgcagagg  10080
acgacacata gagtagcgga gtaggccagc gtagtacgca tgtgcttgtg tgtgaggcgt  10140
ctctctcttc gtctcctgtt tgcgcaaacg catagactgc actgagaaaa tcgattacct  10200
attttttatg aatgaatatt tgcactatta ctattcaaaa ctattaagat agcaatcaca  10260
ttcaatagcc aaatactata ccacctgagc gatgcaacga aatgatcaat ttgagcaaaa  10320
atgctgcata tttaggacgg catcattata gaaatgcttc ttgctgtgta cttttctctc  10380
gtctggcagc tgtttcgccg ttattgttaa aaccggctta agttaggtgt gttttctacg  10440
actagtgatg cccctactag aagatgtgtg ttgcacaaat gtccctgaat aaccaatttg  10500
aagtgcagat agcagtaaac gtaagctaat atgaatatta tttaactgta atgttttaat  10560
atcgctggac attactaata aacccactat aaacacatgt acatatgtat gttttggcat  10620
acaatgagta gttggggaaa aaatgtgtaa aagcaccgtg accatcacag cataaagata  10680
accagctgaa gtatcgaata tgagtaaccc ccaaattgaa tcacatgccg caactgatag  10740
gacccatgga agtacactct tcatggcgat atacaagaca cacacaagca cgaacaccca  10800
gttgcggagg aaattctccg taaatgaaaa cccaatcggc gaacaattca tacccatata  10860
tggtaaaagt tttgaacgcg acttgagagc ggagagcatt gcggctgata aggttttagc  10920
gctaagcggg ctttataaaa cgggctgcgg gaccagtttt catatcacta ccgtttgagt  10980
```

-continued

```
tcttgtgctg tgtggatact cctcccgaca caaagccgct ccatcagcca gcagtcgtct  11040
aatccagaga ccccggatct agaaccaaaa tggctagatt agataaaagt aaagtgatta  11100
acagcgcatt agagctgctt aatgaggtcg gaatcgaagg tttaacaacc cgtaaactcg  11160
cccagaagct aggtgtagag cagcctacat tgtattggca tgtaaaaaat aagcgggctt  11220
tgctcgacgc cttagccatt gagatgttag ataggcacca tactcacttt tgccctttag  11280
aaggggaaag ctggcaagat tttttacgta ataacgctaa aagttttaga tgtgctttac  11340
taagtcatcg cgatggagca aaagtacatt taggtacacg gcctacagaa aaacagtatg  11400
aaactctcga aaatcaatta gcctttttat gccaacaagg tttttcacta gagaatgcat  11460
tatatgcact cagcgctgtg gggcatttta ctttaggttg cgtattggaa gatcaagagc  11520
atcaagtcgc taaagaagaa agggaaacac ctactactga tagtatgccg ccattattac  11580
gacaagctat cgaattattt gatcaccaag gtgcagagcc agccttctta ttcggccttg  11640
aattgatcat atgcggatta gaaaaacaac ttaaatgtga aagtgggtcc gcgtacagcc  11700
gcgcgcgtac gaaaaacaat tacgggtcta ccatcgaggg cctgctcgat ctcccggacg  11760
acgacgcccc cgaagaggcg gggctggcgg ctccgcgcct gtcctttctc cccgcgggac  11820
acacgcgcag actgtcgacg gcccccccga ccgatgtcag cctgggggac gagctccact  11880
tagacggcga ggacgtggcg atggcgcatg ccgacgcgct agacgatttc gatctggaca  11940
tgttggggga cggggattcc ccgggtccgg gatttacccc ccacgactcc gccccctacg  12000
gcgctctgga tatggccgac ttcgagtttg agcagatgtt taccgatgcc cttggaattg  12060
acgagtacgg tgggtagggg gcgcgag                                      12087
```

<210> SEQ ID NO 16
<211> LENGTH: 11920
<212> TYPE: DNA
<213> ORGANISM: Artificial
<220> FEATURE:
<223> OTHER INFORMATION: pLA513

<400> SEQUENCE: 16

```
gggccgatct gacaatgttc agtgcagaga ctcggctacg cctcgtggac tttgaagttg     60
accaacaatg tttattctta cctctaatag tcctctgtgg caaggtcaag attctgttag    120
aagccaatga agaacctggt tgttcaataa cattttgttc gtctaatatt tcactaccgc    180
ttgacgttgg ctgcacttca tgtacctcat ctataaacgc ttcttctgta tcgctctgga    240
cgtcatcttc acttacgtga tctgatattt cactgtcaga atcctcacca acaagctcgt    300
catcgctttg cagaagagca gagaggatat gctcatcgtc taaagaacta cccattttat    360
tatatattag tcacgatatc tataacaaga aaatatatat ataataagtt atcacgtaag    420
tagaacatga aataacaata taattatcgt atgagttaaa tcttaaaagt cacgtaaaag    480
ataatcatgc gtcattttga ctcacgcggt cgttatagtt caaaatcagt gacacttacc    540
gcattgacaa gcacgcctca cgggagctcc aagcggcgac tgagatgtcc taaatgcaca    600
gcgacggatt cgcgctattt agaaagagag agcaatattt caagaatgca tgcgtcaatt    660
ttacgcagac tatctttcta gggttaaaaa agatttgcgc tttactcgac ctaaacttta    720
aacacgtcat agaatcttcg tttgacaaaa accacattgt ggccaagctg tgtgacgcga    780
cgcgcgctaa agaatggcaa accaagtcgc gcgagcgtcg acctgcaggc atgcaagctt    840
gcatgcctgc aggtcgaaat tcgtaatcat ggtcatagct gtttcctgtg tgaaattgtt    900
atccgctcac aattccacac aacatacgag ccggaagcat aaagtgtaaa gcctggggtg    960
```

```
cctaatgagt gagctaactc acattaattg cgttgcgctc actgcccgct ttccagtcgg   1020

gaaacctgtc gtgccagctg cattaatgaa tcggccaacg cgcgggg aga ggcggtttgc   1080

gtattgggcg ctcttccgct tcctcgctca ctgactcgct gcgctcggtc gttcggctgc   1140

ggcgagcggt atcagctcac tcaaaggcgg taatacggtt atccacagaa tcaggggata   1200

acgcaggaaa gaacatgtga gcaaaaggcc agcaaaaggc caggaaccgt aaaaaggccg   1260

cgttgctggc gtttttccat aggctccgcc cccctgacga gcatcacaaa aatcgacgct   1320

caagtcagag gtggcgaaac ccgacaggac tataaagata ccaggcgttt ccccctggaa   1380

gctccctcgt gcgctctcct gttccgaccc tgccgcttac cggatacctg tccgcctttc   1440

tcccttcggg aagcgtggcg ctttctcaat gctcacgctg taggtatctc agttcggtgt   1500

aggtcgttcg ctccaagctg ggctgtgtgc acgaaccccc cgttcagccc gaccgctgcg   1560

ccttatccgg taactatcgt cttgagtcca acccggtaag acacgactta tcgccactgg   1620

cagcagccac tggtaacagg attagcagag cgaggtatgt aggcggtgct acagagttct   1680

tgaagtggtg gcctaactac ggctacacta gaaggacagt atttggtatc tgcgctctgc   1740

tgaagccagt taccttcgga aaaagagttg gtagctcttg atccggcaaa caaaccaccg   1800

ctggtagcgg tggttttttt gtttgcaagc agcagattac gcgcagaaaa aaaggatctc   1860

aagaagatcc tttgatcttt tctacggggt ctgacgctca gtggaacgaa aactcacgtt   1920

aagggatttt ggtcatgaga ttatcaaaaa ggatcttcac ctagatcctt ttaaattaaa   1980

aatgaagttt taaatcaatc taaagtatat atgagtaaac ttggtctgac agttaccaat   2040

gcttaatcag tgaggcacct atctcagcga tctgtctatt tcgttcatcc atagttgcct   2100

gactccccgt cgtgtagata actacgatac gggagggctt accatctggc cccagtgctg   2160

caatgatacc gcgagaccca cgctcaccgg ctccagattt atcagcaata aaccagccag   2220

ccggaagggc cgagcgcaga agtggtcctg caactttatc cgcctccatc cagtctatta   2280

attgttgccg ggaagctaga gtaagtagtt cgccagttaa tagtttgcgc aacgttgttg   2340

ccattgctac aggcatcgtg gtgtcacgct cgtcgtttgg tatggcttca ttcagctccg   2400

gttcccaacg atcaaggcga gttacatgat cccccatgtt gtgcaaaaaa gcggttagct   2460

ccttcggtcc tccgatcgtt gtcagaagta agttggccgc agtgttatca ctcatggtta   2520

tggcagcact gcataattct cttactgtca tgccatccgt aagatgcttt tctgtgactg   2580

gtgagtactc aaccaagtca ttctgagaat agtgtatgcg gcgaccgagt tgctcttgcc   2640

cggcgtcaat acgggataat accgcgccac atagcagaac tttaaaagtg ctcatcattg   2700

gaaaacgttc ttcggggcga aaactctcaa ggatcttacc gctgttgaga tccagttcga   2760

tgtaacccac tcgtgcaccc aactgatctt cagcatcttt tactttcacc agcgtttctg   2820

ggtgagcaaa aacaggaagg caaaatgccg caaaaaaggg aataagggcg acacggaaat   2880

gttgaatact catactcttc ctttttcaat attattgaag catttatcag ggttattgtc   2940

tcatgagcgg atacatattt gaatgtattt agaaaaataa acaaataggg gttccgcgca   3000

catttccccg aaaagtgcca cctgacgtct aagaaaccat tattatcatg acattaacct   3060

ataaaaatag gcgtatcacg aggccctttc gtctcgcgcg tttcggtgat gacggtgaaa   3120

acctctgaca catgcagctc ccggagacgg tcacagcttg tctgtaagcg gatgccggga   3180

gcagacaagc ccgtcagggc gcgtcagcgg gtgttggcgg gtgtcggggc tggcttaact   3240

atgcggcatc agagcagatt gtactgagag tgcaccatat gcggtgtgaa ataccgcaca   3300
```

-continued

```
gatgcgtaag gagaaaatac cgcatcaggc gccattcgcc attcaggctg cgcaactgtt   3360
gggaagggcg atcggtgcgg gcctcttcgc tattacgcca gctggcgaaa gggggatgtg   3420
ctgcaaggcg attaagttgg gtaacgccag ggttttccca gtcacgacgt tgtaaaacga   3480
cggccagtgc caagctttgt ttaaaatata acaaaattgt gatcccacaa aatgaagtgg   3540
ggcaaaatca aataattaat agtgtccgta aacttgttgg tcttcaactt tttgaggaac   3600
acgttggacg gcaaatccgt gactataaca caagttgatt taataatttt agccaacacg   3660
tcgggctgcg tgtttttgc cgacgcgtct gtgtacacgt tgattaactg gtcgattaaa   3720
ctgttgaaat aatttaattt ttggttcttc tttaaatctg tgatgaaatt ttttaaaata   3780
actttaaatt cttcattggt aaaaaatgcc acgttttgca acttgtgagg gtctaatatg   3840
aggtcaaact cagtaggagt tttatccaaa aaagaaaaca tgattacgtc tgtacacgaa   3900
cgcgtattaa cgcagagtgc aaagtataag agggttaaaa aatatatttt acgcaccata   3960
tacgcatcgg gttgatatcg ttaatatgga tcaatttgaa cagttgatta acgtgtctct   4020
gctcaagtct ttgatcaaaa cgcaaatcga cgaaaatgtg tcggacaata tcaagtcgat   4080
gagcgaaaaa ctaaaaaggc tagaatacga caatctcaca gacagcgttg agatatacgg   4140
tattcacgac agcaggctga ataataaaaa aattagaaac tattatttaa ccctagaaag   4200
ataatcatat tgtgacgtac gttaaagata atcatgcgta aaattgacgc atgtgtttta   4260
tcggtctgta tatcgaggtt tatttattaa tttgaataga tattaagttt tattatattt   4320
acacttacat actaataata aattcaacaa acaatttatt tatgtttatt tatttattaa   4380
aaaaaaacaa aaactcaaaa tttcttctat aaagtaacaa aacttttaaa cattctctct   4440
tttacaaaaa taaacttatt ttgtacttta aaaacagtca tgttgtatta taaaataagt   4500
aattagctta acttatacat aatagaaaca aattatactt attagtcagt cagaaacaac   4560
tttggcacat atcaatatta tgctctcgac aaataacttt tttgcatttt ttgcacgatg   4620
catttgcctt tcgccttatt ttagaggggc agtaagtaca gtaagtacgt tttttcatta   4680
ctggctcttc agtactgtca tctgatgtac caggcacttc atttggcaaa atattagaga   4740
tattatcgcg caaatatctc ttcaaagtag gagcttctaa acgcttacgc ataaacgatg   4800
acgtcaggct catgtaaagg tttctcataa attttttgcg actttggacc ttttctccct   4860
tgctactgac attatggctg tatataataa aagaatttat gcaggcaatg tttatcattc   4920
cgtacaataa tgccataggc cacctattcg tcttcctact gcaggtcatc acagaacaca   4980
tttggtctag cgtgtccact ccgcctttag tttgattata atacataacc atttgcggtt   5040
taccggtact ttcgttgata gaagcatcct catcacaaga tgataataag tataccatct   5100
tagctggctt cggtttatat gagacgagag taaggggtcc gtcaaaacaa aacatcgatg   5160
ttcccactgg cctggagcga ctgtttttca gtacttccgg tatctcgcgt ttgtttgatc   5220
gcacggttcc cacaatggtt gcggccggcc agatttaaat gagcggccgc agatatccag   5280
tgcagtaaaa aaaaaaaatg ttttttttat ctactttccg caaaaatggg ttttattaac   5340
ttacatacat actagaattc tatattctaa aaacacaaat gatacttcta aaaaaaatca   5400
tgaatggcat caactctgaa tcaaatcttt gcagatgcac ctacttctca tttccactgt   5460
cacatcattt ttccagatct cgctgcctgt tatgtggccc acaaaccaag acacgtttta   5520
tggccattaa agctggctga tcgtcgccaa acaccaaata catatcaata tgtacattcg   5580
agaaagaagc gatcaaagaa gcgtcttcgg gcgagtagga gaatgcggag gagaaggaga   5640
acgagctgat ctagtatctc tccacaatcc aatgccaact gaccaactgg ccatattcgg   5700
```

-continued

```
agcaatttga agccaatttc catcgcctgg cgatcgctcc attcttggct atatgttttt   5760
caccgttccc ggggccattt tcaaagactc gtcggtaaga taagattgtg tcactcgctg   5820
tctctcttca tttgtcgaag aatgctgagg aatttcgcga tgacgtcggc gagtattttg   5880
aagaatgaga ataatttgta tttatacgaa aatcagttag tggaattttc tacaaaaaca   5940
tgttatctat agataatttt gttgcaaaat atgttgacta tgacaaagat tgtatgtata   6000
tacctttaat gtattctcat tttcttatgt atttataatg gcaatgatga tactgatgat   6060
attttaagat gatgccagac cacaggctga tttctgcgtc ttttgccgaa cgcagtgcat   6120
gtgcggttgt tgtttttttgg aatagtttca attttcggac tgtccgcttt gatttcagtt   6180
tcttggctta ttcaaaaagc aaagtaaagc caaaaaagcg agatggcaat accaaatgcg   6240
gcaaaacggt agtggaagga aaggggtgcg gggcagcgga aggaagggtg gggcggggcg   6300
tggcggggtc tgtggctggg cgcgacgtca ccgacgttgg agccactcct ttgaccatgt   6360
gtgcgtgtgt gtattattcg tgtctcgcca ctcgccggtt gtttttttct ttttatctcg   6420
ctctctctag cgccatctcg tacgcatgct caacgcaccg catgttgccg tgtcctttat   6480
gcgtcatttt ggctcgaaat aggcaattat ttaaacaaag attagtcaac gaaaacgcta   6540
aaataaataa gtctacaata tggttactta ttgccatgtg tgtgcagcca acgatagcaa   6600
caaaagcaac aacacagtgg ctttccctct ttcacttttt gtttgcaagc gcgtgcgagc   6660
aagacggcac gaccggcaaa cgcaattacg ctgacaaaga gcagacgaag ttttggccga   6720
aaaacatcaa ggcgcctgat acgaatgcat ttgcaataac aattgcgata tttaatattg   6780
tttatgaagc tgtttgactt caaaacacac aaaaaaaaaa ataaaacaaa ttatttgaaa   6840
gagaattagg aatcggacag cttatcgtta cgggctaaca gcacaccgag acgaaatagc   6900
ttacctgacg tcacagcctc tggaagaact gccgccaagc agacgatgca gaggacgaca   6960
catagagtag cggagtaggc cagcgtagta cgcatgtgct tgtgtgtgag gcgtctctct   7020
cttcgtctcc tgtttgcgca aacgcataga ctgcactgag aaaatcgatt acctattttt   7080
tatgaatgaa tatttgcact attactattc aaaactatta agatagcaat cacattcaat   7140
agccaaatac tataccacct gagcgatgca acgaaatgat caatttgagc aaaaatgctg   7200
catatttagg acggcatcat tatagaaatg cttcttgctg tgtacttttc tctcgtctgg   7260
cagctgtttc gccgttattg ttaaaaccgg cttaagttag gtgtgttttc tacgactagt   7320
gatgccccta ctagaagatg tgtgttgcac aaatgtccct gaataaccaa tttgaagtgc   7380
agatagcagt aaacgtaagc taatatgaat attatttaac tgtaatgttt taatatcgct   7440
ggacattact aataaaccca ctataaacac atgtacatat gtatgttttg gcatacaatg   7500
agtagttggg gaaaaaatgt gtaaaagcac cgtgaccatc acagcataaa gataaccagc   7560
tgaagtatcg aatatgagta acccccaaat tgaatcacat gccgcaactg ataggaccca   7620
tggaagtaca ctcttcatgg cgatatacaa gacacacaca agcacgaaca cccagttgcg   7680
gaggaaattc tccgtaaatg aaaacccaat cggcgaacaa ttcataccca tatatggtaa   7740
aagttttgaa cgcgacttga gagcggagag cattgcggct gataaggttt tagcgctaag   7800
cgggctttat aaaacgggct gcgggaccag ttttcatatc actaccgttt gagttcttgt   7860
gctgtgtgga tactcctccc gacacaaagc cgctccatca gccagcagtc gtctaatcca   7920
gagaccccgg atctagaacc aaaatggcta gaatggcctc ctccgagaac gtcatcaccg   7980
agttcatgcg cttcaaggtg cgcatggagg gcaccgtgaa cggccacgag ttcgagatcg   8040
```

-continued

```
agggcgaggg cgagggccgc ccctacgagg gccacaacac cgtgaagctg aaggtgacca   8100
agggcggccc cctgcccttc gcctgggaca tcctgtcccc ccagttccag tacggctcca   8160
aggtgtacgt gaagcacccc gccgacatcc ccgactacaa gaagctgtcc ttccccgagg   8220
gcttcaagtg ggagcgcgtg atgaacttcg aggacggcgg cgtggcgacc gtgacccagg   8280
actcctccct gcaggacggc tgcttcatct acaaggtgaa gttcatcggc gtgaacttcc   8340
cctccgacgg ccccgtgatg cagaagaaga ccatgggctg ggaggcctcc accgagcgcc   8400
tgtacccccg cgacggcgtg ctgaagggcg agacccacaa ggccctgaag ctgaaggacg   8460
gcggccacta cctggtggag ttcaagtcca tctacatggc caagaagccc gtgcagctgc   8520
ccggctacta ctacgtggac gccaagctgg acatcacctc ccacaacgag gactacacca   8580
tcgtggagca gtacgagcgc accgagggcc gccaccacct gttcctgtga gatccatgag   8640
caattagcat gaacgttctg aaaagcgcgt ttagctctcc actacttaca catattctat   8700
gctgcaatat tgaaaatcta ataaacaaaa ctaatgtaca ttaattcttc agttttgaat   8760
atccttctcc tgactttctt atttagaatt aatataatac tgcatacatt aatactgtaa   8820
atatgataag tacctgcaaa acactgcagc tcaagtctta atgaggttct gcgatagctt   8880
agcataatta gtaacttatc gcgcagaatt ccctaatgtt cccgacctac atgtacttct   8940
gatagttgcc gaggtcaaat gttgttgtat ttgtattata cctcaatatt ggtatattca   9000
atatctaata gtacccaatt caattgcaaa gatagtcatt aaaaaaacct aaatcacttg   9060
caaattgact ttctgccgg aaaagcaacc ttgacacaca aagttaatta gtttatctgg   9120
aagtcatgtg agaaatttgt aaataaaatt tttcgcagta atttaagtgg cctaatccc   9180
ttttaagcat cttggtttta cgatgacacc gcaataaggt acaactttat attgtttttg   9240
caatcagctt gagtctttat taggcatcag tctttctctc taagtttctt cgtgcaataa   9300
atgaggttcc aaactccgta gatttttcct tctttgttga atccagatcc tgcaaagaaa   9360
aaagagcaaa cccctaggtc tgtccaggaa tgtattttcg tgtttgtcga tcgaccatgg   9420
tctcgagggg gggccttaat taagaggcgc gccaggtttc gactttcact tttctctatc   9480
actgataggg agtggtaaac tcgactttca cttttctcta tcactgatag ggagtggtaa   9540
actcgacttt cacttttctc tatcactgat agggagtggt aaactcgact ttcacttttc   9600
tctatcactg atagggagtg gtaaactcga ctttcacttt tctctatcac tgatagggag   9660
tggtaaactc gactttcact tttctctatc actgataggg agtggtaaac tcgactttca   9720
cttttctcta tcactgatag ggagtggtaa actcgaaaac gagcgccgga gtataaatag   9780
aggcgcttcg tctacggagc gacaattcaa ttcaaacaag caaagtgaac acgtcgctaa   9840
gcgaaagcta agcaaataaa caagcgcagc tgaacaagct aaacaatctg cggtaccctg   9900
gcggtaagtt gatcaaagga aacgcaaagt tttcaagaaa aaacaaaact aatttgattt   9960
ataacacctt tagaaaccac catgggcagc cgcctggata agtccaaagt catcaactcc  10020
gcgttggagc tgttgaacga agttggcatt gagggactga cgacccgcaa gttggcgcag  10080
aagctgggcg tggagcagcc caccctctac tggcacgtga agaataagcg ggcgctgctg  10140
gatgccctgg ccatcgagat gctcgaccgc caccacacgc atttttgccc gttggaaggc  10200
gagtcctggc aggacttcct ccgcaataac gccaagtcgt tccgctgcgc tctgctgtcc  10260
caccgagacg gtgccaaagt ccatctcggc acgcgcccga ccgaaaagca atacgagaca  10320
ctggagaacc agctcgcgtt cctgtgccag caaggcttca gcctggaaaa tgctctctac  10380
gctctgagcg ccgtcggtca ctttaccctg ggctgcgtgc tggaggacca agagcatcaa  10440
```

gtcgcaaaag aggagcgcga gaccccaaca accgattcga tgccccact gctgcgtcag 10500 gcaatcgagc tgttcgatca tcaaggagcc gagccggcat tcctgttcgg cttggagctg 10560
attatctgcg gattggaaaa gcaactgaaa tgcgagtcgg gctcgggccc cgcgtacagc 10620
cgcgcgcgta cgaaaaacaa ttacgggtct accatcgagg gcctgctcga tctcccggac 10680
gacgacgccc ccgaagaggc ggggctggcg gctccgcgcc tgtcctttct ccccgcggga 10740
cacacgcgca gactgtcgac ggcccccccg accgatgtca gcctgggga cgagctccac 10800 ttagacggcg aggacgtggc gatggcgcat gccgacgcgc tagacgattt cgatctggac 10860
atgttggggg acggggattc cccgggtccg ggatttaccc cccacgactc cgcccccctac 10920 ggcgctctgg atatggccga cttcgagttt gagcagatgt ttaccgatgc ccttggaatt 10980
gacgagtacg gtgggtagtt ctagagtcga cctcgaacgt taacgttaac gtaacgttaa 11040
ctcgaggagc ttgataacat tatacctaaa cccatggtca agagtaaaca tttctgcctt 11100
tgaagttgag aacacaatta agcatcccct ggttaaacct gacattcata cttgttaata 11160
gcgccataaa catagcacca atttcgaaga aatcagttaa aagcaattag caattagcaa 11220
ttagcaataa ctctgctgac ttcaaaacga gaagagttgc aagtatttgt aaggcacagt 11280
ttatagacca ccgacggctc attagggctc gtcatgtaac taagcgcggt gaaacccaat 11340
tgaacatata gtggaattat tattatcaat ggggaagatt taaccctcag gtagcaaagt 11400
aatttaattg caaatagaga gtcctaagac taaataatat atttaaaaat ctggcccttt 11460
gaccttgctt gtcaggtgca tttgggttca atcgtaagtt gcttctatat aaacactttc 11520
cccatccccg caataatgaa gaataccgca gaataaagag agatttgcaa caaaaaataa 11580
aggcattgcg aaaacttttt atgggggatc attacactcg ggcctacggt tacaattccc 11640
agccacttaa gcgacaagtt tggccaacaa tccatctaat agctaatagc gcaatcactg 11700
gtaatcgcaa gagtatatag gcaatagaac ccatggattt gaccaaaggt aaccgagaca 11760
atggagaagc aagaggattt caaactgaac acccacagta ctgtgtacta ccactggcgc 11820
gtttgggagc tccaagcggc gactgagatg tcctaaatgc acagcgacgg attcgcgcta 11880
tttagaaaga gagagcaata tttcaagaaa aacggcgccc 11920

<210> SEQ ID NO 17
<211> LENGTH: 11570
<212> TYPE: DNA
<213> ORGANISM: Artificial
<220> FEATURE:
<223> OTHER INFORMATION: pLA517

<400> SEQUENCE: 17
ggccgctcat ttaaatctgg ccggccgcaa ccattgtggg aaccgtgcga tcaaacaaac 60
gcgagatacc ggaagtactg aaaaacagtc gctccaggcc agtgggaaca tcgatgtttt 120
gttttgacgg accccttact ctcgtctcat ataaaccgaa gccagctaag atggtatact 180
tattatcatc ttgtgatgag gatgcttcta tcaacgaaag taccggtaaa ccgcaaatgg 240
ttatgtatta taatcaaact aaaggcggag tggacacgct agaccaaatg tgttctgtga 300
tgacctgcag taggaagacg aataggtggc ctatggcatt attgtacgga atgataaaca 360
ttgcctgcat aaattctttt attatataca gccataatgt cagtagcaag ggagaaaagg 420
tccaaagtcg caaaaaattt atgagaaacc tttacatgag cctgacgtca tcgtttatgc 480
gtaagcgttt agaagctcct actttgaaga gatatttgcg cgataatatc tctaatattt 540

-continued

```
tgccaaatga agtgcctggt acatcagatg acagtactga agagccagta atgaaaaaac    600
gtacttactg tacttactgc ccctctaaaa taaggcgaaa ggcaaatgca tcgtgcaaaa    660
aatgcaaaaa agttatttgt cgagagcata atattgatat gtgccaaagt tgtttctgac    720
tgactaataa gtataatttg tttctattat gtataagtta agctaattac ttattttata    780
atacaacatg actgttttta aagtacaaaa taagtttatt tttgtaaaag agagaatgtt    840
taaaagtttt gttactttat agaagaaatt ttgagttttt gttttttttt aataaataaa    900
taaacataaa taaattgttt gttgaattta ttattagtat gtaagtgtaa atataataaa    960
acttaatatc tattcaaatt aataaataaa cctcgatata cagaccgata aaacacatgc   1020
gtcaatttta cgcatgatta tctttaacgt acgtcacaat atgattatct ttctagggtt   1080
aaataatagt ttctaatttt tttattattc agcctgctgt cgtgaatacc gtatatctca   1140
acgctgtctg tgagattgtc gtattctagc ctttttagtt tttcgctcat cgacttgata   1200
ttgtccgaca cattttcgtc gatttgcgtt ttgatcaaag acttgagcag agacacgtta   1260
atcaactgtt caaattgatc catattaacg atatcaaccc gatgcgtata tggtgcgtaa   1320
aatatatttt ttaaccctct tatactttgc actctgcgtt aatacgcgtt cgtgtacaga   1380
cgtaatcatg ttttcttttt tggataaaac tcctactgag tttgacctca tattagaccc   1440
tcacaagttg caaaacgtgg catttttttac caatgaagaa tttaaagtta ttttaaaaaa   1500
tttcatcaca gatttaaaga agaaccaaaa attaaattat ttcaacagtt taatcgacca   1560
gttaatcaac gtgtacacag acgcgtcggc aaaaaacacg cagcccgacg tgttggctaa   1620
aattattaaa tcaacttgtg ttatagtcac ggatttgccg tccaacgtgt tcctcaaaaa   1680
gttgaagacc aacaagttta cggacactat taattatttg attttgcccc acttcatttt   1740
gtgggatcac aattttgtta tattttaaac aaagcttggc actggccgtc gttttacaac   1800
gtcgtgactg ggaaaaccct ggcgttaccc aacttaatcg ccttgcagca catccccctt   1860
tcgccagctg gcgtaatagc gaagaggccc gcaccgatcg cccttcccaa cagttgcgca   1920
gcctgaatgg cgaatggcgc ctgatgcggt attttctcct tacgcatctg tgcggtattt   1980
cacaccgcat atggtgcact ctcagtacaa tctgctctga tgccgcatag ttaagccagc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgagacga aagggcctcg tgatacgcct atttttatag gttaatgtca   2220
tgataataat ggtttcttag acgtcaggtg gcacttttcg gggaaatgtg cgcggaaccc   2280
ctatttgttt atttttctaa atacattcaa atatgtatcc gctcatgaga caataaccct   2340
gataaatgct tcaataatat tgaaaaagga agagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
```

-continued

```
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactggggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa aatcccttaa cgtgagtttt   3360
cgttccactg agcgtcagac cccgtagaaa agatcaaagg atcttcttga gatccttttt   3420
ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
ggtatccggt aagcggcagg gtcggaacag gagagcgcac gagggagctt ccagggggaa   3900
acgcctggta tctttatagt cctgtcgggt ttcgccacct ctgacttgag cgtcgatttt   3960
tgtgatgctc gtcagggggg cggagcctat ggaaaaacgc cagcaacgcg gcctttttac   4020
ggttcctggc cttttgctgg ccttttgctc acatgttctt tcctgcgtta tcccctgatt   4080
ctgtggataa ccgtattacc gcctttgagt gagctgatac cgctcgccgc agccgaacga   4140
ccgagcgcag cgagtcagtg agcgaggaag cggaagagcg cccaatacgc aaaccgcctc   4200
tccccgcgcg ttggccgatt cattaatgca gctggcacga caggtttccc gactggaaag   4260
cgggcagtga gcgcaacgca attaatgtga gttagctcac tcattaggca ccccaggctt   4320
tacactttat gcttccggct cgtatgttgt gtggaattgt gagcggataa caatttcaca   4380
caggaaacag ctatgaccat gattacgaat ttcgacctgc aggcatgcaa gcttgcatgc   4440
ctgcaggtcg acgctcgcgc gacttggttt gccattcttt agcgcgcgtc gcgtcacaca   4500
gcttggccac aatgtggttt ttgtcaaacg aagattctat gacgtgttta aagtttaggt   4560
cgagtaaagc gcaaatcttt tttaacccta gaaagatagt ctgcgtaaaa ttgacgcatg   4620
cattcttgaa atattgctct ctctttctaa atagcgcgaa tccgtcgctg tgcatttagg   4680
acatctcagt cgccgcttgg agctcccgtg aggcgtgctt gtcaatgcgg taagtgtcac   4740
tgattttgaa ctataacgac cgcgtgagtc aaaatgacgc atgattatct tttacgtgac   4800
ttttaagatt taactcatac gataattata ttgttatttc atgttctact tacgtgataa   4860
cttattatat atatatttc ttgttataga tatcgtgact aatatataat aaaatgggta   4920
gttctttaga cgatgagcat atcctctctg ctcttctgca aagcgatgac gagcttgttg   4980
gtgaggattc tgacagtgaa atatcagatc acgtaagtga agatgacgtc cagagcgata   5040
cagaagaagc gtttatagat gaggtacatg aagtgcagcc aacgtcaagc ggtagtgaaa   5100
tattagacga acaaaatgtt attgaacaac caggttcttc attggcttct aacagaatct   5160
tgaccttgcc acagaggact attagaggta agaataaaca ttgttggtca acttcaaagt   5220
ccacgaggcg tagccgagtc tctgcactga acattgtcag atcggcccgg gcgccgtttc   5280
```

```
ccaaacgcgc cagtggtagt acacagtact gtgggtgttc agtttgaaat cctcttgctt   5340
ctccattgtc tcggttacct ttggtcaaat ccatgggttc tattgcctat atactcttgc   5400
gattaccagt gattgcgcta ttagctatta gatggattgt tggccaaact tgtcgcttaa   5460
gtggctggga attgtaaccg taggcccgag tgtaatgatc ccccataaaa agttttcgca   5520
atgcctttat tttttgttgc aaatctctct ttattctgcg gtattcttca ttattgcggg   5580
gatggggaaa gtgtttatat agaagcaact tacgattgaa cccaaatgca cctgacaagc   5640
aaggtcaaag ggccagattt ttaaatatat tatttagtct taggactctc tatttgcaat   5700
taaattactt tgctacctga gggttaaatc ttccccattg ataataataa ttccactata   5760
tgttcaattg ggtttcaccg cgcttagtta catgacgagc cctaatgagc cgtcggtggt   5820
ctataaactg tgccttacaa atacttgcaa ctcttctcgt tttgaagtca gcagagttat   5880
tgctaattgc taattgctaa ttgcttttaa ctgatttctt cgaaattggt gctatgttta   5940
tggcgctatt aacaagtatg aatgtcaggt ttaaccaggg gatgcttaat tgtgttctca   6000
acttcaaagg cagaaatgtt tactcttgac catgggttta ggtataatgt tatcaagctc   6060
ctcgagttaa cgttacgtta acgttaacgt tcgaggtcga ctctagatta ttacagcatg   6120
tcgagatcaa agtcgtccaa agcatcagcg ggcaacatat ccaagtcaaa atcatcgaga   6180
gcgtccgccg gcagcatatc caggtcgaag tcatccaggg catcggcggg gcccgagccc   6240
gactcgcatt tcagttgctt ttccaatccg cagataatca gctccaagcc gaacaggaat   6300
gccggctcgg ctccttgatg atcgaacagc tcgattgcct gacgcagcag tgggggcatc   6360
gaatcggttg ttggggtctc gcgctcctct tttgcgactt gatgctcttg gtcctccagc   6420
acgcagccca gggtaaagtg accgacggcg ctcagagcgt agagagcatt ttccaggctg   6480
aagccttgct ggcacaggaa cgcgagctgg ttctccagtg tctcgtattg cttttcggtc   6540
gggcgcgtgc cgagatggac tttggcaccg tctcggtggg acagcagagc gcagcggaac   6600
gacttggcgt tattgcggag gaagtcctgc caggactcgc cttccaacgg gcaaaaatgc   6660
gtgtggtggc ggtcgagcat ctcgatggcc agggcatcca gcagcgcccg cttattcttc   6720
acgtgccagt agagggtggg ctgctccacg cccagcttct gcgccaactt gcgggtcgtc   6780
agtccctcaa tgccaacttc gttcaacagc tccaacgcgg agttgatgac tttggactta   6840
tccaggcggc tgcccatggt ggtttctaaa ggtgttataa atcaaattag ttttgttttt   6900
tcttgaaaac tttgcgtttc ctttgatcaa cttaccgcca gggtaccgca gattgtttag   6960
cttgttcagc tgcgcttgtt tatttgctta gctttcgctt agcgacgtgt tcactttgct   7020
tgtttgaatt gaattgtcgc tccgtagacg aagcgcctct atttatactc cggcgctcgt   7080
tttcgagttt accactccct atcagtgata gagaaaagtg aaagtcgagt ttaccactcc   7140
ctatcagtga tagagaaaag tgaaagtcga gtttaccact ccctatcagt gatagagaaa   7200
agtgaaagtc gagtttacca ctccctatca gtgatagaga aaagtgaaag tcgagtttac   7260
cactccctat cagtgataga gaaaagtgaa agtcgagttt accactccct atcagtgata   7320
gagaaaagtg aaagtcgagt ttaccactcc ctatcagtga tagagaaaag tgaaagtcga   7380
aacctggcgc gcctcttaat taaggccccc cctcgagacc atggtcgatc gacaaacacg   7440
aaaatacatt cctggacaga cctaggggtt tgctcttttt tctttgcagg atctggattc   7500
aacaaagaag gaaaaatcta cggagtttgg aacctcattt attgcacgaa gaaacttaga   7560
gagaaagact gatgcctaat aaagactcaa gctgattgca aaaacaatat aaagttgtac   7620
cttattgcgg tgtcatcgta aaaccaagat gcttaaaagg gattaggccc acttaaatta   7680
```

-continued

```
ctgcgaaaaa ttttatttac aaatttctca catgacttcc agataaacta attaactttg   7740
tgtgtcaagg ttgcttttcc ggcagaaaag tcaatttgca agtgatttag gtttttttaa   7800
tgactatctt tgcaattgaa ttgggtacta ttagatattg aatataccaa tattgaggta   7860
taatacaaat acaacaacat ttgacctcgg caactatcag aagtacatgt aggtcgggaa   7920
cattagggaa ttctgcgcga taagttacta attatgctaa gctatcgcag aacctcatta   7980
agacttgagc tgcagtgttt tgcaggtact tatcatattt acagtattaa tgtatgcagt   8040
attatattaa ttctaaataa gaaagtcagg agaaggatat tcaaaactga agaattaatg   8100
tacattagtt ttgtttatta gattttcaat attgcagcat agaatatgtg taagtagtgg   8160
agagctaaac gcgcttttca gaacgttcat gctaattgct catggatctc acaggaacag   8220
gtggtggcgg ccctcggtgc gctcgtactg ctccacgatg gtgtagtcct cgttgtggga   8280
ggtgatgtcc agcttggcgt ccacgtagta gtagccgggc agctgcacgg gcttcttggc   8340
catgtagatg gacttgaact ccaccaggta gtggccgccg tccttcagct tcagggcctt   8400
gtgggtctcg cccttcagca cgccgtcgcg ggggtacagg cgctcggtgg aggcctccca   8460
gcccatggtc ttcttctgca tcacggggcc gtcggagggg aagttcacgc cgatgaactt   8520
caccttgtag atgaagcagc cgtcctgcag ggaggagtcc tgggtcacgg tcgccacgcc   8580
gccgtcctcg aagttcatca cgcgctccca cttgaagccc tcggggaagg acagcttctt   8640
gtagtcgggg atgtcggcgg ggtgcttcac gtacaccttg gagccgtact ggaactgggg   8700
ggacaggatg tcccaggcga agggcagggg gccgcccttg gtcaccttca gcttcacggt   8760
gttgtggccc tcgtaggggc ggccctcgcc ctcgccctcg atctcgaact cgtggccgtt   8820
cacggtgccc tccatgcgca ccttgaagcg catgaactcg gtgatgacgt tctcggagga   8880
ggccattcta gccatttggg ttctagatcc ggggtctctg gattagacga ctgctggctg   8940
atggagcggc tttgtgtcgg gaggagtatc cacacagcac aagaactcaa acggtagtga   9000
tatgaaaact ggtcccgcag cccgttttat aaagcccgct tagcgctaaa accttatcag   9060
ccgcaatgct ctccgctctc aagtcgcgtt caaaactttt accatatatg ggtatgaatt   9120
gttcgccgat tgggttttca tttacggaga atttcctccg caactgggtg ttcgtgcttg   9180
tgtgtgtctt gtatatcgcc atgaagagtg tacttccatg ggtcctatca gttgcggcat   9240
gtgattcaat ttgggggtta ctcatattcg atacttcagc tggttatctt tatgctgtga   9300
tggtcacggt gcttttacac attttttccc caactactca ttgtatgcca aaacatacat   9360
atgtacatgt gtttatagtg ggtttattag taatgtccag cgatattaaa acattacagt   9420
taaataatat tcatattagc ttacgtttac tgctatctgc acttcaaatt ggttattcag   9480
ggacatttgt gcaacacaca tcttctagta ggggcatcac tagtcgtaga aaacacacct   9540
aacttaagcc ggttttaaca ataacggcga aacagctgcc agacgagaga aaagtacaca   9600
gcaagaagca tttctataat gatgccgtcc taaatatgca gcatttttgc tcaaattgat   9660
catttcgttg catcgctcag gtggtatagt atttggctat tgaatgtgat tgctatctta   9720
atagttttga atagtaatag tgcaaatatt cattcataaa aaataggtaa tcgattttct   9780
cagtgcagtc tatgcgtttg cgcaaacagg agacgaagag agagacgcct cacacacaag   9840
cacatgcgta ctacgctggc ctactccgct actctatgtg tcgtcctctg catcgtctgc   9900
ttggcggcag ttcttccaga ggctgtgacg tcaggtaagc tatttcgtct cggtgtgctg   9960
ttagcccgta acgataagct gtccgattcc taattctctt tcaaataatt tgttttattt  10020
```

-continued

```
ttttttttgt gtgttttgaa gtcaaacagc ttcataaaca atattaaata tcgcaattgt  10080
tattgcaaat gcattcgtat caggcgcctt gatgtttttc ggccaaaact tcgtctgctc  10140
tttgtcagcg taattgcgtt tgccggtcgt gccgtcttgc tcgcacgcgc ttgcaaacaa  10200
aaagtgaaag agggaaagcc actgtgttgt tgcttttgtt gctatcgttg gctgcacaca  10260
catggcaata agtaaccata ttgtagactt atttatttta gcgttttcgt tgactaatct  10320
ttgtttaaat aattgcctat ttcgagccaa aatgacgcat aaaggacacg gcaacatgcg  10380
gtgcgttgag catgcgtacg agatggcgct agagagagcg agataaaaag aaaaaaacaa  10440
ccggcgagtg gcgagacacg aataatacac acacgcacac atggtcaaag gagtggctcc  10500
aacgtcggtg acgtcgcgcc cagccacaga ccccgccacg ccccgcccca cccttccttc  10560
cgctgccccg cacccctttc cttccactac cgttttgccg catttggtat tgccatctcg  10620
ctttttttggc tttactttgc tttttgaata agccaagaaa ctgaaatcaa agcggacagt  10680
ccgaaaattg aaactattcc aaaaaacaac aaccgcacat gcactgcgtt cggcaaaaga  10740
cgcagaaatc agcctgtggt ctggcatcat cttaaaatat catcagtatc atcattgcca  10800
ttataaatac ataagaaaat gagaatacat taaaggtata tacatacaat ctttgtcata  10860
gtcaacatat tttgcaacaa aattatctat agataacatg tttttgtaga aaattccact  10920
aactgatttt cgtataaata caaattattc tcattcttca aaatactcgc cgacgtcatc  10980
gcgaaattcc tcagcattct tcgacaaatg aagagagaca gcgagtgaca caatcttatc  11040
ttaccgacga gtctttgaaa atggccccgg gaacggtgaa aaacatatag ccaagaatgg  11100
agcgatcgcc aggcgatgga aattggcttc aaattgctcc gaatatggcc agttggtcag  11160
ttggcattgg attgtggaga gatactagat cagctcgttc tccttctcct ccgcattctc  11220
ctactcgccc gaagacgctt ctttgatcgc ttctttctcg aatgtacata ttgatatgta  11280
tttggtgttt ggcgacgatc agccagcttt aatggccata aaacgtgtct tggtttgtgg  11340
gccacataac aggcagcgag atctggaaaa atgatgtgac agtggaaatg agaagtaggt  11400
gcatctgcaa agatttgatt cagagttgat gccattcatg atttttttta gaagtatcat  11460
ttgtgttttt agaatataga attctagtat gtatgtaagt taataaaacc catttttgcg  11520
gaaagtagat aaaaaaaaca ttttttttt ttactgcact ggatatctgc             11570
```

<210> SEQ ID NO 18
<211> LENGTH: 11251
<212> TYPE: DNA
<213> ORGANISM: Artificial
<220> FEATURE:
<223> OTHER INFORMATION: pLA656

<400> SEQUENCE: 18

```
cgccaggcga tggaaattgg cttcaaattg ctccgaatat ggccagttgg tcagttggca     60
ttggattgtg gagagatact agatcagctc gttctccttc tcctccgcat tctcctactc    120
gcccgaagac gcttctttga tcgcttcttt ctcgaatgta catattgata tgtatttggt    180
gtttggcgac gatcagccag ctttaatggc cataaaacgt gtcttggttt gtgggccaca    240
taacaggcag cgagatctgg aaaaatgatg tgacagtgga aatgagaagt aggtgcatct    300
gcaaagattt gattcagagt tgatgccatt catgattttt tttagaagta tcatttgtgt    360
ttttagaata tagaattcta gtatgtatgt aagttaataa aacccatttt tgcggaaagt    420
agataaaaaa aacatttttt tttttactg cactggatat ctgcggccgc tcatttaaat    480
ctggccggcc gcaaccattg tgggaaccgt gcgatcaaac aaacgcgaga taccggaagt    540
```

-continued actgaaaaac agtcgctcca ggccagtggg aacatcgatg ttttgttttg acggacccct 600
tactctcgtc tcatataaac cgaagccagc taagatggta tacttattat catcttgtga 660
tgaggatgct tctatcaacg aaagtaccgg taaaccgcaa atggttatgt attataatca 720
aactaaaggc ggagtggaca cgctagacca aatgtgttct gtgatgacct gcagtaggaa 780
gacgaatagg tggcctatgg cattattgta cggaatgata aacattgcct gcataaattc 840
ttttattata tacagccata atgtcagtag caagggagaa aaggtccaaa gtcgcaaaaa 900
atttatgaga aacctttaca tgagcctgac gtcatcgttt atgcgtaagc gtttagaagc 960
tcctactttg aagagatatt tgcgcgataa tatctctaat attttgccaa atgaagtgcc 1020
tggtacatca gatgacagta ctgaagagcc agtaatgaaa aaacgtactt actgtactta 1080
ctgcccctct aaaataaggc gaaaggcaaa tgcatcgtgc aaaaaatgca aaaaagttat 1140
ttgtcgagag cataatattg atatgtgcca aagttgtttc tgactgacta ataagtataa 1200
tttgtttcta ttatgtataa gttaagctaa ttacttattt tataatacaa catgactgtt 1260
tttaaagtac aaaataagtt tatttttgta aaagagagaa tgtttaaaag ttttgttact 1320
ttatagaaga aattttgagt ttttgttttt ttttaataaa taaataaaca taaataaatt 1380
gtttgttgaa tttattatta gtatgtaagt gtaaatataa taaaacttaa tatctattca 1440
aattaataaa taaacctcga tatacagacc gataaaacac atgcgtcaat tttacgcatg 1500
attatcttta acgtacgtca caatatgatt atctttctag ggttaaataa tagtttctaa 1560
tttttttatt attcagcctg ctgtcgtgaa taccgtatat ctcaacgctg tctgtgagat 1620
tgtcgtattc tagccttttt agtttttcgc tcatcgactt gatattgtcc gacacatttt 1680
cgtcgatttg cgttttgatc aaagacttga gcagagacac gttaatcaac tgttcaaatt 1740
gatccatatt aacgatatca acccgatgcg tatatggtgc gtaaaatata ttttttaacc 1800
ctcttatact ttgcactctg cgttaatacg cgttcgtgta cagacgtaat catgttttct 1860
tttttggata aaactcctac tgagtttgac ctcatattag accctcacaa gttgcaaaac 1920
gtggcatttt ttaccaatga agaatttaaa gttattttaa aaaatttcat cacagattta 1980
aagaagaacc aaaaattaaa ttatttcaac agtttaatcg accagttaat caacgtgtac 2040
acagacgcgt cggcaaaaaa cacgcagccc gacgtgttgg ctaaaattat taaatcaact 2100
tgtgttatag tcacggattt gccgtccaac gtgttcctca aaaagttgaa gaccaacaag 2160
tttacggaca ctattaatta tttgattttg ccccacttca ttttgtggga tcacaatttt 2220
gttatatttt aaacaaagct tggcactggc cgtcgtttta caacgtcgtg actgggaaaa 2280
ccctggcgtt acccaactta atcgccttgc agcacatccc cctttcgcca gctggcgtaa 2340
tagcgaagag gcccgcaccg atcgcccttc ccaacagttg cgcagcctga atggcgaatg 2400
gcgcctgatg cggtattttc tccttacgca tctgtgcggt atttcacacc gcatatggtg 2460
cactctcagt acaatctgct ctgatgccgc atagttaagc cagccccgac acccgccaac 2520
acccgctgac gcgccctgac gggcttgtct gctcccggca tccgcttaca gacaagctgt 2580
gaccgtctcc gggagctgca tgtgtcagag gttttcaccg tcatcaccga aacgcgcgag 2640
acgaaagggc ctcgtgatac gcctattttt ataggttaat gtcatgataa taatggtttc 2700
ttagacgtca ggtggcactt ttcggggaaa tgtgcgcgga acccctattt gtttattttt 2760
ctaaatacat tcaaatatgt atccgctcat gagacaataa ccctgataaa tgcttcaata 2820
atattgaaaa aggaagagta tgagtattca acatttccgt gtcgccctta ttcccttttt 2880

-continued

```
tgcggcattt tgccttcctg tttttgctca cccagaaacg ctggtgaaag taaaagatgc   2940
tgaagatcag ttgggtgcac gagtgggtta catcgaactg gatctcaaca gcggtaagat   3000
ccttgagagt tttcgccccg aagaacgttt tccaatgatg agcactttta aagttctgct   3060
atgtggcgcg gtattatccc gtattgacgc cgggcaagag caactcggtc gccgcataca   3120
ctattctcag aatgacttgg ttgagtactc accagtcaca gaaaagcatc ttacggatgg   3180
catgacagta agagaattat gcagtgctgc cataaccatg agtgataaca ctgcggccaa   3240
cttacttctg acaacgatcg gaggaccgaa ggagctaacc gcttttttgc acaacatggg   3300
ggatcatgta actcgccttg atcgttggga accggagctg aatgaagcca taccaaacga   3360
cgagcgtgac accacgatgc ctgtagcaat ggcaacaacg ttgcgcaaac tattaactgg   3420
cgaactactt actctagctt cccggcaaca attaatagac tggatggagg cggataaagt   3480
tgcaggacca cttctgcgct cggcccttcc ggctggctgg tttattgctg ataaatctgg   3540
agccggtgag cgtgggtctc gcggtatcat tgcagcactg gggccagatg gtaagccctc   3600
ccgtatcgta gttatctaca cgacggggag tcaggcaact atggatgaac gaaatagaca   3660
gatcgctgag ataggtgcct cactgattaa gcattggtaa ctgtcagacc aagtttactc   3720
atatatactt tagattgatt taaaacttca tttttaattt aaaaggatct aggtgaagat   3780
cctttttgat aatctcatga ccaaaatccc ttaacgtgag ttttcgttcc actgagcgtc   3840
agaccccgta gaaaagatca aaggatcttc ttgagatcct ttttttctgc gcgtaatctg   3900
ctgcttgcaa acaaaaaaac caccgctacc agcggtggtt tgtttgccgg atcaagagct   3960
accaactctt tttccgaagg taactggctt cagcagagcg cagataccaa atactgtcct   4020
tctagtgtag ccgtagttag gccaccactt caagaactct gtagcaccgc ctacatacct   4080
cgctctgcta atcctgttac cagtggctgc tgccagtggc gataagtcgt gtcttaccgg   4140
gttggactca agacgatagt taccggataa ggcgcagcgg tcgggctgaa cggggggttc   4200
gtgcacacag cccagcttgg agcgaacgac ctacaccgaa ctgagatacc tacagcgtga   4260
gcattgagaa agcgccacgc ttcccgaagg gagaaaggcg gacaggtatc cggtaagcgg   4320
cagggtcgga acaggagagc gcacgaggga gcttccaggg ggaaacgcct ggtatcttta   4380
tagtcctgtc gggtttcgcc acctctgact tgagcgtcga tttttgtgat gctcgtcagg   4440
ggggcggagc ctatggaaaa acgccagcaa cgcggccttt ttacggttcc tggccttttg   4500
ctggcctttt gctcacatgt tctttcctgc gttatcccct gattctgtgg ataaccgtat   4560
taccgccttt gagtgagctg ataccgctcg ccgcagccga acgaccgagc gcagcgagtc   4620
agtgagcgag gaagcggaag agcgcccaat acgcaaaccg cctctccccg cgcgttggcc   4680
gattcattaa tgcagctggc acgacaggtt tcccgactgg aaagcgggca gtgagcgcaa   4740
cgcaattaat gtgagttagc tcactcatta ggcaccccag gctttacact ttatgcttcc   4800
ggctcgtatg ttgtgtggaa ttgtgagcgg ataacaattt cacacaggaa acagctatga   4860
ccatgattac gaatttcgac ctgcaggcat gcaagcttgc atgcctgcag gtcgacgctc   4920
gcgcgacttg gtttgccatt ctttagcgcg cgtcgcgtca cacagcttgg ccacaatgtg   4980
gtttttgtca aacgaagatt ctatgacgtg tttaaagttt aggtcgagta aagcgcaaat   5040
ctttttttaac cctagaaaga tagtctgcgt aaaattgacg catgcattct tgaaatattg   5100
ctctctcttt ctaaatagcg cgaatccgtc gctgtgcatt taggacatct cagtcgccgc   5160
ttggagctcc cgtgaggcgt gcttgtcaat gcggtaagtg tcactgattt tgaactataa   5220
cgaccgcgtg agtcaaaatg acgcatgatt atcttttacg tgacttttaa gatttaactc   5280
```

atacgataat tatattgtta tttcatgttc tacttacgtg ataacttatt atatatatat 5340
tttcttgtta tagatatcgt gactaatata taataaaatg ggtagttctt tagacgatga 5400
gcatatcctc tctgctcttc tgcaaagcga tgacgagctt gttggtgagg attctgacag 5460
tgaaatatca gatcacgtaa gtgaagatga cgtccagagc gatacagaag aagcgtttat 5520
agatgaggta catgaagtgc agccaacgtc aagcggtagt gaaatattag acgaacaaaa 5580
tgttattgaa caaccaggtt cttcattggc ttctaacaga atcttgacct tgccacagag 5640
gactattaga ggtaagaata aacattgttg gtcaacttca aagtccacga ggcgtagccg 5700
agtctctgca ctgaacattg tcagatcggc ccgggcgccg tttttcttga aatattgctc 5760
tctctttcta aatagcgcga atccgtcgct gtgcatttag gacatctcag tcgccgcttg 5820
gagctcccaa acgcgccagt ggtagtacac agtactgtgg gtgttcagtt tgaaatcctc 5880
ttgcttctcc attgtctcgg ttacctttgg tcaaatccat gggttctatt gcctatatac 5940
tcttgcgatt accagtgatt gcgctattag ctattagatg gattgttggc caaacttgtc 6000
gcttaagtgg ctgggaattg taaccgtagg cccgagtgta atgatccccc ataaaaagtt 6060
ttcgcaatgc ctttattttt tgttgcaaat ctctctttat tctgcggtat tcttcattat 6120
tgcggggatg gggaaagtgt ttatatagaa gcaacttacg attgaaccca aatgcacctg 6180
acaagcaagg tcaaagggcc agatttttaa atatattatt tagtcttagg actctctatt 6240
tgcaattaaa ttactttgct acctgagggt taaatcttcc ccattgataa taataattcc 6300
actatatgtt caattgggtt tcaccgcgct tagttacatg acgagcccta atgagccgtc 6360
ggtggtctat aaactgtgcc ttacaaatac ttgcaactct tctcgttttg aagtcagcag 6420
agttattgct aattgctaat tgctaattgc ttttaactga tttcttcgaa attggtgcta 6480
tgtttatggc gctattaaca agtatgaatg tcaggtttaa ccaggggatg cttaattgtg 6540
ttctcaactt caaaggcaga aatgtttact cttgaccatg ggtttaggta taatgttatc 6600
aagctcctcg agttaacgtt acgttaacgt taacgttcga ggtcgactct agaactaccc 6660
accgtactcg tcaattccaa gggcatcggt aaacatctgc tcaaactcga agtcggccat 6720
atccagagcg ccgtaggggg cggagtcgtg gggggtaaat cccggacccg gggaatcccc 6780
gtcccccaac atgtccagat cgaaatcgtc tagcgcgtcg gcatgcgcca tcgccacgtc 6840
ctcgccgtct aagtggagct cgtcccccag gctgacatcg gtcggggggg ccgtcgacag 6900
tctgcgcgtg tgtcccgcgg ggagaaagga caggcgcgga gccgccagcc ccgcctcttc 6960
gggggcgtcg tcgtccggga gatcgagcag gccctcgatg gtagacccgt aattgttttt 7020
cgtacgcgcg cggctgtacg cggggcccga gcccgactcg catttcagtt gcttttccaa 7080
tccgcagata atcagctcca agccgaacag gaatgccggc tcggctcctt gatgatcgaa 7140
cagctcgatt gcctgacgca gcagtggggg catcgaatcg gttgttgggg tctcgcgctc 7200
ctcttttgcg acttgatgct cttggtcctc cagcacgcag cccagggtaa agtgaccgac 7260
ggcgctcaga gcgtagagag cattttccag gctgaagcct tgctggcaca ggaacgcgag 7320
ctggttctcc agtgtctcgt attgcttttc ggtcgggcgc gtgccgagat ggactttggc 7380
accgtctcgg tgggacagca gagcgcagcg gaacgacttg gcgttattgc ggaggaagtc 7440
ctgccaggac tcgccttcca acgggcaaaa atgcgtgtgg tggcggtcga gcatctcgat 7500
ggccagggca tccagcagcg cccgcttatt cttcacgtgc cagtagaggg tgggctgctc 7560
cacgcccagc ttctgcgcca acttgcgggt cgtcagtccc tcaatgccaa cttcgttcaa 7620

-continued

```
cagctccaac gcggagttga tgactttgga cttatccagg cggctgccca tggtggtttc   7680
taaaggtgtt ataaatcaaa ttagttttgt tttttcttga aaactttgcg tttcctttga   7740
tcaacttacc gccagggtac cgcagattgt ttagcttgtt cagctgcgct tgtttatttg   7800
cttagctttc gcttagcgac gtgttcactt tgcttgtttg aattgaattg tcgctccgta   7860
gacgaagcgc ctctatttat actccggcgc tcgttttcga gtttaccact ccctatcagt   7920
gatagagaaa agtgaaagtc gagtttacca ctccctatca gtgatagaga aaagtgaaag   7980
tcgagtttac cactccctat cagtgataga gaaaagtgaa agtcgagttt accactccct   8040
atcagtgata gagaaaagtg aaagtcgagt ttaccactcc ctatcagtga tagagaaaag   8100
tgaaagtcga gtttaccact ccctatcagt gatagagaaa agtgaaagtc gagtttacca   8160
ctccctatca gtgatagaga aaagtgaaag tcgaaacctg gcgcgcctct taattaactc   8220
gcgttaagat acattgatga gtttggacaa accacaacta gaatgcagtg aaaaaaatgc   8280
tttatttgtg aaatttgtga tgctattgct ttatttgtaa ccattataag ctgcaataaa   8340
caagttaaca acaacaattg cattcatttt atgtttcagg ttcaggggga ggtgtgggag   8400
gttttttaaa gcaagtaaaa cctctacaaa tgtggtatgg ctgattatga tcagttatct   8460
agatccggtg gatcttacgg gtcctccacc ttccgctttt tcttgggtcg agatctcagg   8520
aacaggtggt ggcggccctc ggtgcgctcg tactgctcca cgatggtgta gtcctcgttg   8580
tgggaggtga tgtccagctt ggcgtccacg tagtagtagc cgggcagctg cacgggcttc   8640
ttggccatgt agatggactt gaactccacc aggtagtggc cgccgtcctt cagcttcagg   8700
gccttgtggg tctcgccctt cagcacgccg tcgcgggggt acaggcgctc ggtggaggcc   8760
tcccagccca tggtcttctt ctgcatcacg gggccgtcgg aggggaagtt cacgccgatg   8820
aacttcacct tgtagatgaa gcagccgtcc tgcagggagg agtcctgggt cacggtcgcc   8880
acgccgccgt cctcgaagtt catcacgcgc tcccacttga agccctcggg gaaggacagc   8940
ttcttgtagt cggggatgtc ggcggggtgc ttcacgtaca ccttggagcc gtactggaac   9000
tggggggaca ggatgtccca ggcgaagggc agggggccgc ccttggtcac cttcagcttc   9060
acggtgttgt ggccctcgta ggggcggccc tcgccctcgc cctcgatctc gaactcgtgg   9120
ccgttcacgg tgccctccat gcgcaccttg aagcgcatga actcggtgat gacgttctcg   9180
gaggaggcca tggtggcgac cggtttgcgc ttcttcttgg gtggggtggg atccccgatc   9240
tgcattttgg attattctgc gggtcaaaat agagatgtgg aaaattagta cgaaatcaaa   9300
tgagtttcgt tgaaattaca aaactattga aactaacttc ctggctgggg aataaaaatg   9360
ggaaacttat ttatcgacgc caactttgtt gagaaacccc tattaaccct ctacgaatat   9420
tggaacaaag gaaagcgaag aaacaggaac aaaggtagtt gagaaacctg ttccgttgct   9480
cgtcatcgtt ttcataatgc gagtgtgtgc atgtatatat acacagctga aacgcatgca   9540
tacacattat tttgtgtgta tatggtgacg tcacaactac taagcaataa gaaattttcc   9600
agacgtggct ttcgtttcaa gcaacctact ctatttcagc taaaaataag tggatttcgt   9660
tggtaaaata cttcaattaa gcaaagaact aactaactaa taacatgcac acaaatgctc   9720
gagtgcgttc gtgatttctc gaattttcaa atgcgtcact gcgaatttca caatttgcca   9780
ataaatcttg gcgaaaatca acacgcaagt tttatttata gatttgtttg cgttttgatg   9840
ccaattgatt gggaaaacaa gatgcgtggc tgccaatttc ttattttgta attacgtaga   9900
gcgttgaata aaaaaaaaat ggccgaacaa agaccttgaa atgcagtttt tcttgaaatt   9960
actcaacgtc ttgttgctct tattactaat tggtaacagc gagttaaaaa cttacgtttc  10020
```

-continued

```
ttgtgacttt cgagaatgtt cttttaattg tactttaatc accaacaatt aagtataaat  10080
ttttcgctga ttgcgcttta ctttctgctt gtacttgctg ctgcaaatgt caattggttt  10140
tgaaggcgac cgttcgcgaa cgctgtttat ataccttcgg tgtccgttga aaatcactaa  10200
aaaataccgt agtgttcgta acactttagt acagagaaaa aaaattgtgc cgaaatgttt  10260
ttgatacgta cgaatacctt gtattaaaat tttttatgat ttctgtgtat cacttttttt  10320
ttgtgttttt cgtttaaact caccacagta caaaacaata aaatattttt aagacaattt  10380
caaattgaga cctttctcgt actgacttga ccggctgaat gaggatttct acctagacga  10440
cctacttctt accatgacat tgaatgcaat gccacctttg atctaaactt acaaaagtcc  10500
aaggcttgtt aggattggtg tttatttagt ttgcttttga aatagcactg tcttctctac  10560
cggctataat tttgaaactc gcagcttgac tggaaattta aaaagtaatt ctgtgtaggt  10620
aaagggtgtt ttaaaagtgt gatgtgttga gcgttgcggc aacgactgct atttatgtat  10680
atattttcaa aacttattgt ttttgaagtg ttttaaatgg agctatctgg caacgctgcg  10740
cataatctta cacaagcttt tcttaatcca tttttaagtg aaatttgttt ttactctttc  10800
ggcaaataat tgttaaatcg ctttaagtgg gcttacatct ggataagtaa tgaaaacctg  10860
catattataa tattaaaaca tataatccac tgtgctttcc ccgtgtgtgg ccatatacct  10920
aaaaaagttt attttcgcag agccccgcac ggtcacacta cggttcggcg attttcgatt  10980
ttggacagta ctgattgcaa gcgcaccgaa agcaaaatgg agctggagat tttgaacgcg  11040
aagaacagca agccgtacgg caaggtgaag gtgccctccg gcgccacgcc catcggcgat  11100
ctgcgcgccc taattcacaa gaccctgaag cagaccccac acgcgaatcg ccagtcgctt  11160
cgtctggaac tgaagggcaa aagcctgaaa gatacggaca cattggaatc tctgtcgctg  11220
cgttccggcg acaagatcgg ggtaccgcga t                                 11251
```

<210> SEQ ID NO 19
<211> LENGTH: 9468
<212> TYPE: DNA
<213> ORGANISM: Artificial
<220> FEATURE:
<223> OTHER INFORMATION: pLA710

<400> SEQUENCE: 19

```
ggccgctcat ttaaatctgg ccggccgcaa ccattgtggg aaccgtgcga tcaaacaaac     60
gcgagatacc ggaagtactg aaaaacagtc gctccaggcc agtgggaaca tcgatgtttt    120
gttttgacgg accccttact ctcgtctcat ataaaccgaa gccagctaag atggtatact    180
tattatcatc ttgtgatgag gatgcttcta tcaacgaaag taccggtaaa ccgcaaatgg    240
ttatgtatta taatcaaact aaaggcggag tggacacgct agaccaaatg tgttctgtga    300
tgacctgcag taggaagacg aataggtggc ctatggcatt attgtacgga atgataaaca    360
ttgcctgcat aaattctttt attatataca gccataatgt cagtagcaag ggagaaaagg    420
tccaaagtcg caaaaaattt atgagaaacc tttacatgag cctgacgtca tcgtttatgc    480
gtaagcgttt agaagctcct actttgaaga gatatttgcg cgataatatc tctaatattt    540
tgccaaatga agtgcctggt acatcagatg acagtactga agagccagta atgaaaaaac    600
gtacttactg tacttactgc ccctctaaaa taaggcgaaa ggcaaatgca tcgtgcaaaa    660
aatgcaaaaa agttatttgt cgagagcata atattgatat gtgccaaagt tgtttctgac    720
tgactaataa gtataatttg tttctattat gtataagtta agctaattac ttattttata    780
```

-continued

```
atacaacatg actgttttta aagtacaaaa taagtttatt tttgtaaaag agagaatgtt    840
taaaagtttt gttactttat agaagaaatt ttgagttttt gttttttttt aataaataaa    900
taaacataaa taaattgttt gttgaattta ttattagtat gtaagtgtaa atataataaa    960
acttaatatc tattcaaatt aataaataaa cctcgatata cagaccgata aaacacatgc   1020
gtcaatttta cgcatgatta tctttaacgt acgtcacaat atgattatct ttctagggtt   1080
aaataatagt ttctaatttt tttattattc agcctgctgt cgtgaatacc gtatatctca   1140
acgctgtctg tgagattgtc gtattctagc ctttttagtt tttcgctcat cgacttgata   1200
ttgtccgaca cattttcgtc gatttgcgtt ttgatcaaag acttgagcag agacacgtta   1260
atcaactgtt caaattgatc catattaacg atatcaaccc gatgcgtata tggtgcgtaa   1320
aatatatttt ttaaccctct tatactttgc actctgcgtt aatacgcgtt cgtgtacaga   1380
cgtaatcatg ttttcttttt tggataaaac tcctactgag tttgacctca tattagaccc   1440
tcacaagttg caaaacgtgg catttttttac caatgaagaa tttaaagtta ttttaaaaaa   1500
tttcatcaca gatttaaaga agaaccaaaa attaaattat ttcaacagtt taatcgacca   1560
gttaatcaac gtgtacacag acgcgtcggc aaaaaaacacg cagcccgacg tgttggctaa   1620
aattattaaa tcaacttgtg ttatagtcac ggatttgccg tccaacgtgt tcctcaaaaa   1680
gttgaagacc aacaagttta cggacactat taattatttg attttgcccc acttcatttt   1740
gtgggatcac aattttgtta tattttaaac aaagcttggc actggccgtc gttttacaac   1800
gtcgtgactg ggaaaaccct ggcgttaccc aacttaatcg ccttgcagca catccccctt   1860
tcgccagctg gcgtaatagc gaagaggccc gcaccgatcg cccttcccaa cagttgcgca   1920
gcctgaatgg cgaatggcgc ctgatgcggt attttctcct tacgcatctg tgcggtattt   1980
cacaccgcat atggtgcact ctcagtacaa tctgctctga tgccgcatag ttaagccagc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgagacga aagggcctcg tgatacgcct atttttatag gttaatgtca   2220
tgataataat ggtttcttag acgtcaggtg gcacttttcg gggaaatgtg cgcggaaccc   2280
ctatttgttt atttttctaa atacattcaa atatgtatcc gctcatgaga caataaccct   2340
gataaatgct tcaataatat tgaaaaagga agagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactggggc   3120
cagatggtaa gccctcccgt atcgtagtta tctacacgac ggggagtcag gcaactatgg   3180
```

-continued atgaacgaaa tagacagatc gctgagatag gtgcctcact gattaagcat tggtaactgt 3240
cagaccaagt ttactcatat atactttaga ttgatttaaa acttcatttt taatttaaaa 3300
ggatctaggt gaagatcctt tttgataatc tcatgaccaa aatcccttaa cgtgagtttt 3360
cgttccactg agcgtcagac cccgtagaaa agatcaaagg atcttcttga gatccttttt 3420
ttctgcgcgt aatctgctgc ttgcaaacaa aaaaaccacc gctaccagcg gtggtttgtt 3480
tgccggatca agagctacca actctttttc cgaaggtaac tggcttcagc agagcgcaga 3540
taccaaatac tgtccttcta gtgtagccgt agttaggcca ccacttcaag aactctgtag 3600
caccgcctac atacctcgct ctgctaatcc tgttaccagt ggctgctgcc agtggcgata 3660
agtcgtgtct taccgggttg gactcaagac gatagttacc ggataaggcg cagcggtcgg 3720
gctgaacggg gggttcgtgc acacagccca gcttggagcg aacgacctac accgaactga 3780
gatacctaca gcgtgagcat tgagaaagcg ccacgcttcc cgaagggaga aaggcggaca 3840
ggtatccggt aagcggcagg gtcggaacag gagagcgcac gagggagctt ccagggggaa 3900
acgcctggta tctttatagt cctgtcgggt ttcgccacct ctgacttgag cgtcgatttt 3960
tgtgatgctc gtcagggggg cggagcctat ggaaaaacgc cagcaacgcg gcctttttac 4020
ggttcctggc cttttgctgg ccttttgctc acatgttctt tcctgcgtta tcccctgatt 4080
ctgtggataa ccgtattacc gcctttgagt gagctgatac cgctcgccgc agccgaacga 4140
ccgagcgcag cgagtcagtg agcgaggaag cggaagagcg cccaatacgc aaaccgcctc 4200
tccccgcgcg ttggccgatt cattaatgca gctggcacga caggtttccc gactggaaag 4260
cgggcagtga gcgcaacgca attaatgtga gttagctcac tcattaggca ccccaggctt 4320
tacactttat gcttccggct cgtatgttgt gtggaattgt gagcggataa caatttcaca 4380
caggaaacag ctatgaccat gattacgaat ttcgacctgc aggcatgcaa gcttgcatgc 4440
ctgcaggtcg acgctcgcgc gacttggttt gccattcttt agcgcgcgtc gcgtcacaca 4500
gcttggccac aatgtggttt ttgtcaaacg aagattctat gacgtgttta aagtttaggt 4560
cgagtaaagc gcaaatcttt tttaacccta gaaagatagt ctgcgtaaaa ttgacgcatg 4620
cattcttgaa atattgctct ctctttctaa atagcgcgaa tccgtcgctg tgcatttagg 4680
acatctcagt cgccgcttgg agctcccgtg aggcgtgctt gtcaatgcgg taagtgtcac 4740
tgattttgaa ctataacgac cgcgtgagtc aaaatgacgc atgattatct tttacgtgac 4800
ttttaagatt taactcatac gataattata ttgttatttc atgttctact tacgtgataa 4860
cttattatat atatatttc ttgttataga tatcgtgact aatatataat aaaatgggta 4920
gttctttaga cgatgagcat atcctctctg ctcttctgca aagcgatgac gagcttgttg 4980
gtgaggattc tgacagtgaa atatcagatc acgtaagtga agatgacgtc cagagcgata 5040
cagaagaagc gtttatagat gaggtacatg aagtgcagcc aacgtcaagc ggtagtgaaa 5100
tattagacga acaaaatgtt attgaacaac caggttcttc attggcttct aacagaatct 5160
tgaccttgcc acagaggact attagaggta agaataaaca ttgttggtca acttcaaagt 5220
ccacgaggcg tagccgagtc tctgcactga acattgtcag atcggcccgg gcgccgtttt 5280
tcttgaaata ttgctctctc tttctaaata gcgcgaatcc gtcgctgtgc atttaggaca 5340
tctcagtcgc cgcttggagc tcccaaacgc gccagtggta gtacacagta ctgtgggtgt 5400
tcagtttgaa atcctcttgc ttctccattg tctcggttac ctttggtcaa atccatgggt 5460
tctattgcct atatactctt gcgattacca gtgattgcgc tattagctat tagatggatt 5520

-continued

```
gttggccaaa cttgtcgctt aagtggctgg gaattgtaac cgtaggcccg agtgtaatga   5580
tcccccataa aaagttttcg caatgccttt attttttgtt gcaaatctct ctttattctg   5640
cggtattctt cattattgcg ggatgggga aagtgtttat atagaagcaa cttacgattg    5700
aacccaaatg cacctgacaa gcaaggtcaa agggccagat ttttaaatat attatttagt   5760
cttaggactc tctatttgca attaaattac tttgctacct gagggttaaa tcttccccat   5820
tgataataat aattccacta tatgttcaat tgggtttcac cgcgcttagt tacatgacga   5880
gccctaatga gccgtcggtg gtctataaac tgtgccttac aaatacttgc aactcttctc   5940
gttttgaagt cagcagagtt attgctaatt gctaattgct aattgctttt aactgatttc   6000
ttcgaaattg gtgctatgtt tatggcgcta ttaacaagta tgaatgtcag gtttaaccag   6060
gggatgctta attgtgttct caacttcaaa ggcagaaatg tttactcttg accatgggtt   6120
taggtataat gttatcaagc tcctcgagtt aacgttacgt taacgttaac gttcgaggtc   6180
gactctagaa ctacccaccg tactcgtcaa ttccaagggc atcggtaaac atctgctcaa   6240
actcgaagtc ggccatatcc agagcgccgt agggggcgga gtcgtggggg gtaaatcccg   6300
gacccgggga atccccgtcc cccaacatgt ccagatcgaa atcgtctagc gcgtcggcat   6360
gcgccatcgc cacgtcctcg ccgtctaagt ggagctcgtc ccccaggctg acatcggtcg   6420
ggggggccgt cgacagtctg cgcgtgtgtc ccgcggggag aaaggacagg cgcggagccg   6480
ccagccccgc ctcttcgggg gcgtcgtcgt ccgggagatc gagcaggccc tcgatggtag   6540
acccgtaatt gtttttcgta cgcgcgcggc tgtacgcggg gcccgagccc gactcgcatt   6600
tcagttgctt ttccaatccg cagataatca gctccaagcc gaacaggaat gccggctcgg   6660
ctccttgatg atcgaacagc tcgattgcct gacgcagcag tgggggcatc gaatcggttg   6720
ttggggtctc gcgctcctct tttgcgactt gatgctcttg gtcctccagc acgcagccca   6780
gggtaaagtg accgacggcg ctcagagcgt agagagcatt ttccaggctg aagccttgct   6840
ggcacaggaa cgcgagctgg ttctccagtg tctcgtattg cttttcggtc gggcgcgtgc   6900
cgagatggac tttggcaccg tctcggtggg acagcagagc gcagcggaac gacttggcgt   6960
tattgcggag gaagtcctgc caggactcgc cttccaacgg gcaaaaatgc gtgtggtggc   7020
ggtcgagcat ctcgatggcc agggcatcca gcagcgcccg cttattcttc acgtgccagt   7080
agagggtggg ctgctccacg cccagcttct gcgccaactt gcgggtcgtc agtccctcaa   7140
tgccaacttc gttcaacagc tccaacgcgg agttgatgac tttggactta tccaggcggc   7200
tgcccatggt ggtttctaaa ggtgttataa atcaaattag ttttgttttt tcttgaaaac   7260
tttgcgtttc ctttgatcaa cttaccgcca gggtaccgca gattgtttag cttgttcagc   7320
tgcgcttgtt tatttgctta gctttcgctt agcgacgtgt tcactttgct tgtttgaatt   7380
gaattgtcgc tccgtagacg aagcgcctct atttatactc cggcgctcgt tttcgagttt   7440
accactccct atcagtgata gagaaaagtg aaagtcgagt ttaccactcc ctatcagtga   7500
tagagaaaag tgaaagtcga gtttaccact ccctatcagt gatagagaaa agtgaaagtc   7560
gagtttacca ctccctatca gtgatagaga aaagtgaaag tcgagtttac cactccctat   7620
cagtgataga gaaaagtgaa agtcgagttt accactccct atcagtgata gagaaaagtg   7680
aaagtcgagt ttaccactcc ctatcagtga tagagaaaag tgaaagtcga aacctggcgc   7740
gcctcttaat taactcgcgt taagatacat tgatgagttt ggacaaacca caactagaat   7800
gcagtgaaaa aaatgcttta tttgtgaaat ttgtgatgct attgctttat ttgtaaccat   7860
tataagctgc aataaacaag ttaacaacaa caattgcatt cattttatgt ttcaggttca   7920
```

```
gggggaggtg tgggaggttt tttaaagcaa gtaaaacctc tacaaatgtg gtatggctga   7980

ttatgatcag ttatctagat ccggtggatc ttacgggtcc tccaccttcc gctttttctt   8040

gggtcgagat ctcaggaaca ggtggtggcg gccctcggtg cgctcgtact gctccacgat   8100

ggtgtagtcc tcgttgtggg aggtgatgtc cagcttggcg tccacgtagt agtagccggg   8160

cagctgcacg ggcttcttgg ccatgtagat ggacttgaac tccaccaggt agtggccgcc   8220

gtccttcagc ttcagggcct tgtgggtctc gcccttcagc acgccgtcgc gggggtacag   8280

gcgctcggtg gaggcctccc agcccatggt cttcttctgc atcacggggc cgtcggaggg   8340

gaagttcacg ccgatgaact tcaccttgta gatgaagcag ccgtcctgca gggaggagtc   8400

ctgggtcacg gtcgccacgc cgccgtcctc gaagttcatc acgcgctccc acttgaagcc   8460

ctcggggaag gacagcttct tgtagtcggg gatgtcggcg gggtgcttca cgtacacctt   8520

ggagccgtac tggaactggg gggacaggat gtcccaggcg aagggcaggg ggccgccctt   8580

ggtcaccttc agcttcacgg tgttgtggcc ctcgtagggg cggccctcgc cctcgccctc   8640

gatctcgaac tcgtggccgt tcacggtgcc ctccatgcgc accttgaagc gcatgaactc   8700

ggtgatgacg ttctcggagg aggccatggt ggcgaccggt ttgcgcttct tcttgggtgg   8760

ggtgggatcc tcgtcgcaca tcttgaatta gtctgcaaga aaagaaaaaa aacaattcaa   8820

actacattct cattccatac attatactaa gtaaacgaca aatttatttg cgtccatcta   8880

tttagtgacg ttaaagaaaa ctgtataaga ttcataattc actgttccca atttctgttt   8940

ccgaattgat cgatgcgagt ggacactttg aaatgtgcgt ccaataaact tatttcttat   9000

ttagtagtgt ttattaacat ctgcagtaca ctaaattccg aaaaatgttt tttttttataa   9060

aaaatttcac ttcactagtt atgcaacaat tatgtaacgt aacacgttat cattagcgta   9120

ttattaaaaa aaaaaaacac tcaaacatat gtaatactta aaggtaaagg gacggagaac   9180

cttcgaaatt caaattttac aaataaataa atatgttttt ttttctttcg caattttaaa   9240

attaaaactt acatagtatt attaaataag tgacaagtac gtagatgcga atgcgcactg   9300

ttcgagcaca ccttagtaaa tgagaaccga ctcgtgagga taaactatat aaaagagccg   9360

ttatcacaat ttacacagta tcggctccag tttgtttttc caccaatcgc gggctgactc   9420

agtttttgtc accatatatg gtaacgcgca cgctatcagg taccatgc                9468
```

<210> SEQ ID NO 20
<211> LENGTH: 10140
<212> TYPE: DNA
<213> ORGANISM: Artificial
<220> FEATURE:
<223> OTHER INFORMATION: pLA928

<400> SEQUENCE: 20

```
ggccgctcat ttaaatctgg ccggccgcaa ccattgtggg aaccgtgcga tcaaacaaac     60

gcgagatacc ggaagtactg aaaaacagtc gctccaggcc agtgggaaca tcgatgtttt    120

gttttgacgg accccttact ctcgtctcat ataaaccgaa gccagctaag atggtatact    180

tattatcatc ttgtgatgag gatgcttcta tcaacgaaag taccggtaaa ccgcaaatgg    240

ttatgtatta taatcaaact aaaggcggag tggacacgct agaccaaatg tgttctgtga    300

tgacctgcag taggaagacg aataggtggc ctatggcatt attgtacgga atgataaaca    360

ttgcctgcat aaattctttt attatataca gccataatgt cagtagcaag ggagaaaagg    420

tccaaagtcg caaaaaattt atgagaaacc tttacatgag cctgacgtca tcgtttatgc    480
```

-continued

```
gtaagcgttt agaagctcct actttgaaga gatatttgcg cgataatatc tctaatattt    540
tgccaaatga agtgcctggt acatcagatg acagtactga agagccagta atgaaaaaac    600
gtacttactg tacttactgc ccctctaaaa taaggcgaaa ggcaaatgca tcgtgcaaaa    660
aatgcaaaaa agttatttgt cgagagcata atattgatat gtgccaaagt tgtttctgac    720
tgactaataa gtataatttg tttctattat gtataagtta agctaattac ttattttata    780
atacaacatg actgttttta aagtacaaaa taagtttatt tttgtaaaag agagaatgtt    840
taaaagtttt gttactttat agaagaaatt ttgagttttt gttttttttt aataaataaa    900
taaacataaa taaattgttt gttgaattta ttattagtat gtaagtgtaa atataataaa    960
acttaatatc tattcaaatt aataaataaa cctcgatata cagaccgata aaacacatgc   1020
gtcaatttta cgcatgatta tctttaacgt acgtcacaat atgattatct ttctagggtt   1080
aaataatagt ttctaatttt tttattattc agcctgctgt cgtgaatacc gtatatctca   1140
acgctgtctg tgagattgtc gtattctagc ctttttagtt tttcgctcat cgacttgata   1200
ttgtccgaca cattttcgtc gatttgcgtt ttgatcaaag acttgagcag agacacgtta   1260
atcaactgtt caaattgatc catattaacg atatcaaccc gatgcgtata tggtgcgtaa   1320
aatatatttt ttaaccctct tatactttgc actctgcgtt aatacgcgtt cgtgtacaga   1380
cgtaatcatg ttttcttttt tggataaaac tcctactgag tttgacctca tattagaccc   1440
tcacaagttg caaaacgtgg catttttttac caatgaagaa tttaaagtta ttttaaaaaa   1500
tttcatcaca gatttaaaga agaaccaaaa attaaattat ttcaacagtt taatcgacca   1560
gttaatcaac gtgtacacag acgcgtcggc aaaaaaacacg cagcccgacg tgttggctaa   1620
aattattaaa tcaacttgtg ttatagtcac ggatttgccg tccaacgtgt tcctcaaaaa   1680
gttgaagacc aacaagttta cggacactat taattatttg attttgcccc acttcatttt   1740
gtgggatcac aattttgtta tattttaaac aaagcttggc actggccgtc gttttacaac   1800
gtcgtgactg ggaaaaccct ggcgttaccc aacttaatcg ccttgcagca catccccctt   1860
tcgccagctg gcgtaatagc gaagaggccc gcaccgatcg cccttcccaa cagttgcgca   1920
gcctgaatgg cgaatggcgc ctgatgcggt attttctcct tacgcatctg tgcggtattt   1980
cacaccgcat atggtgcact ctcagtacaa tctgctctga tgccgcatag ttaagccagc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgagacga aagggcctcg tgatacgcct atttttatag gttaatgtca   2220
tgataataat ggtttcttag acgtcaggtg gcacttttcg gggaaatgtg cgcggaaccc   2280
ctatttgttt atttttctaa atacattcaa atatgtatcc gctcatgaga caataaccct   2340
gataaatgct tcaataatat tgaaaaagga agagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
```

-continued aagccatacc aaacgacgag cgtgacacca cgatgcctgt agcaatggca acaacgttgc 2940
gcaaactatt aactggcgaa ctacttactc tagcttcccg gcaacaatta atagactgga 3000
tggaggcgga taaagttgca ggaccacttc tgcgctcggc ccttccggct ggctggttta 3060
ttgctgataa atctggagcc ggtgagcgtg ggtctcgcgg tatcattgca gcactggggc 3120
cagatggtaa gccctcccgt atcgtagtta tctacacgac ggggagtcag gcaactatgg 3180
atgaacgaaa tagacagatc gctgagatag gtgcctcact gattaagcat tggtaactgt 3240
cagaccaagt ttactcatat atactttaga ttgatttaaa acttcatttt taatttaaaa 3300
ggatctaggt gaagatcctt tttgataatc tcatgaccaa aatcccttaa cgtgagtttt 3360
cgttccactg agcgtcagac cccgtagaaa agatcaaagg atcttcttga gatccttttt 3420
ttctgcgcgt aatctgctgc ttgcaaacaa aaaaaccacc gctaccagcg gtggtttgtt 3480
tgccggatca agagctacca actctttttc cgaaggtaac tggcttcagc agagcgcaga 3540
taccaaatac tgtccttcta gtgtagccgt agttaggcca ccacttcaag aactctgtag 3600
caccgcctac atacctcgct ctgctaatcc tgttaccagt ggctgctgcc agtggcgata 3660
agtcgtgtct taccgggttg gactcaagac gatagttacc ggataaggcg cagcggtcgg 3720
gctgaacggg gggttcgtgc acacagccca gcttggagcg aacgacctac accgaactga 3780
gatacctaca gcgtgagcat tgagaaagcg ccacgcttcc cgaagggaga aaggcggaca 3840
ggtatccggt aagcggcagg gtcggaacag gagagcgcac gagggagctt ccagggggaa 3900
acgcctggta tctttatagt cctgtcgggt ttcgccacct ctgacttgag cgtcgatttt 3960
tgtgatgctc gtcagggggg cggagcctat ggaaaaacgc cagcaacgcg gcctttttac 4020
ggttcctggc cttttgctgg ccttttgctc acatgttctt tcctgcgtta tcccctgatt 4080
ctgtggataa ccgtattacc gcctttgagt gagctgatac cgctcgccgc agccgaacga 4140
ccgagcgcag cgagtcagtg agcgaggaag cggaagagcg cccaatacgc aaaccgcctc 4200
tccccgcgcg ttggccgatt cattaatgca gctggcacga caggtttccc gactggaaag 4260
cgggcagtga gcgcaacgca attaatgtga gttagctcac tcattaggca ccccaggctt 4320
tacactttat gcttccggct cgtatgttgt gtggaattgt gagcggataa caatttcaca 4380
caggaaacag ctatgaccat gattacgaat ttcgacctgc aggcatgcaa gcttgcatgc 4440
ctgcaggtcg acgctcgcgc gacttggttt gccattcttt agcgcgcgtc gcgtcacaca 4500
gcttggccac aatgtggttt ttgtcaaacg aagattctat gacgtgttta aagtttaggt 4560
cgagtaaagc gcaaatcttt tttaacccta gaaagatagt ctgcgtaaaa ttgacgcatg 4620
cattcttgaa atattgctct ctctttctaa atagcgcgaa tccgtcgctg tgcatttagg 4680
acatctcagt cgccgcttgg agctcccgtg aggcgtgctt gtcaatgcgg taagtgtcac 4740
tgattttgaa ctataacgac cgcgtgagtc aaaatgacgc atgattatct tttacgtgac 4800
ttttaagatt taactcatac gataattata ttgttatttc atgttctact tacgtgataa 4860
cttattatat atatattttc ttgttataga tatcgtgact aatatataat aaaatgggta 4920
gttctttaga cgatgagcat atcctctctg ctcttctgca aagcgatgac gagcttgttg 4980
gtgaggattc tgacagtgaa atatcagatc acgtaagtga agatgacgtc cagagcgata 5040
cagaagaagc gtttatagat gaggtacatg aagtgcagcc aacgtcaagc ggtagtgaaa 5100
tattagacga acaaaatgtt attgaacaac caggttcttc attggcttct aacagaatct 5160
tgaccttgcc acagaggact attagaggta agaataaaca ttgttggtca acttcaaagt 5220

-continued

```
ccacgaggcg tagccgagtc tctgcactga acattgtcag atcggcccgg gcgccgtttt   5280
tcttgaaata ttgctctctc tttctaaata gcgcgaatcc gtcgctgtgc atttaggaca   5340
tctcagtcgc cgcttggagc tcccaaacgc gccagtggta gtacacagta ctgtgggtgt   5400
tcagtttgaa atcctcttgc ttctccattg tctcggttac ctttggtcaa atccatgggt   5460
tctattgcct atatactctt gcgattacca gtgattgcgc tattagctat tagatggatt   5520
gttggccaaa cttgtcgctt aagtggctgg gaattgtaac cgtaggcccg agtgtaatga   5580
tccccccataa aaagttttcg caatgccttt atttttttgtt gcaaatctct ctttattctg   5640
cggtattctt cattattgcg gggatgggga aagtgtttat atagaagcaa cttacgattg   5700
aacccaaatg cacctgacaa gcaaggtcaa agggccagat ttttaaatat attatttagt   5760
cttaggactc tctatttgca attaaattac tttgctacct gagggttaaa tcttccccat   5820
tgataataat aattccacta tatgttcaat tgggtttcac cgcgcttagt tacatgacga   5880
gccctaatga gccgtcggtg gtctataaac tgtgccttac aaatacttgc aactcttctc   5940
gttttgaagt cagcagagtt attgctaatt gctaattgct aattgctttt aactgatttc   6000
ttcgaaattg gtgctatgtt tatggcgcta ttaacaagta tgaatgtcag gtttaaccag   6060
gggatgctta attgtgttct caacttcaaa ggcagaaatg tttactcttg accatgggtt   6120
taggtataat gttatcaagc tcctcgagtt aacgttacgt taacgttaac gttcgaggtc   6180
gactctagaa ctacccaccg tactcgtcaa ttccaagggc atcggtaaac atctgctcaa   6240
actcgaagtc ggccatatcc agagcgccgt agggggcgga gtcgtggggg gtaaatcccg   6300
gacccgggga atccccgtcc cccaacatgt ccagatcgaa atcgtctagc gcgtcggcat   6360
gcgccatcgc cacgtcctcg ccgtctaagt ggagctcgtc ccccaggctg acatcggtcg   6420
ggggggccgt cgacagtctg cgcgtgtgtc ccgcggggag aaaggacagg cgcggagccg   6480
ccagccccgc ctcttcgggg gcgtcgtcgt ccgggagatc gagcaggccc tcgatggtag   6540
acccgtaatt gtttttcgta cgcgcgcggc tgtacgcggg gcccgagccc gactcgcatt   6600
tcagttgctt ttccaatccg cagataatca gctccaagcc gaacaggaat gccggctcgg   6660
ctccttgatg atcgaacagc tcgattgcct gacgcagcag tgggggcatc gaatcggttg   6720
ttggggtctc gcgctcctct tttgcgactt gatgctcttg gtcctccagc acgcagccca   6780
gggtaaagtg accgacggcg ctcagagcgt agagagcatt ttccaggctg aagccttgct   6840
ggcacaggaa cgcgagctgg ttctccagtg tctcgtattg cttttcggtc gggcgcgtgc   6900
cgagatggac tttggcaccg tctcggtggg acagcagagc gcagcggaac gacttggcgt   6960
tattgcggag gaagtcctgc caggactcgc cttccaacgg gcaaaaaatgc gtgtggtggc   7020
ggtcgagcat ctcgatggcc agggcatcca gcagcgcccg cttattcttc acgtgccagt   7080
agagggtggg ctgctccacg cccagcttct gcgccaactt gcgggtcgtc agtccctcaa   7140
tgccaacttc gttcaacagc tccaacgcgg agttgatgac tttggactta tccaggcggc   7200
tgcccatggt ggtttctaaa ggtgttataa atcaaattag ttttgttttt tcttgaaaac   7260
tttgcgtttc ctttgatcaa cttaccgcca gggtaccgca gattgtttag cttgttcagc   7320
tgcgcttgtt tatttgctta gctttcgctt agcgacgtgt tcactttgct tgtttgaatt   7380
gaattgtcgc tccgtagacg aagcgcctct atttatactc cggcgctcgt tttcgagttt   7440
accactccct atcagtgata gagaaaagtg aaagtcgagt ttaccactcc ctatcagtga   7500
tagagaaaag tgaaagtcga gtttaccact ccctatcagt gatagagaaa agtgaaagtc   7560
gagtttacca ctccctatca gtgatagaga aaagtgaaag tcgagtttac cactccctat   7620
```

-continued

```
cagtgataga gaaaagtgaa agtcgagttt accactccct atcagtgata gagaaaagtg   7680
aaagtcgagt ttaccactcc ctatcagtga tagagaaaag tgaaagtcga aacctggcgc   7740
gcctcttaat taactcgcgt taagatacat tgatgagttt ggacaaacca caactagaat   7800
gcagtgaaaa aaatgcttta tttgtgaaat ttgtgatgct attgctttat ttgtaaccat   7860
tataagctgc aataaacaag ttaacaacaa caattgcatt cattttatgt ttcaggttca   7920
gggggaggtg tgggaggttt tttaaagcaa gtaaaacctc tacaaatgtg gtatggctga   7980
ttatgatcag ttatctagat ccggtggatc ttacgggtcc tccaccttcc gctttttctt   8040
gggtcgagat ctcaggaaca ggtggtggcg gccctcggtg cgctcgtact gctccacgat   8100
ggtgtagtcc tcgttgtggg aggtgatgtc cagcttggcg tccacgtagt agtagccggg   8160
cagctgcacg ggcttcttgg ccatgtagat ggacttgaac tccaccaggt agtggccgcc   8220
gtccttcagc ttcagggcct tgtgggtctc gcccttcagc acgccgtcgc gggggtacag   8280
gcgctcggtg gaggcctccc agcccatggt cttcttctgc atcacggggc cgtcggaggg   8340
gaagttcacg ccgatgaact tcaccttgta gatgaagcag ccgtcctgca gggaggagtc   8400
ctgggtcacg gtcgccacgc cgccgtcctc gaagttcatc acgcgctccc acttgaagcc   8460
ctcggggaag gacagcttct tgtagtcggg gatgtcggcg gggtgcttca cgtacacctt   8520
ggagccgtac tggaactggg gggacaggat gtcccaggcg aagggcaggg ggccgccctt   8580
ggtcaccttc agcttcacgg tgttgtggcc ctcgtagggg cggccctcgc cctcgccctc   8640
gatctcgaac tcgtggccgt tcacggtgcc ctccatgcgc accttgaagc gcatgaactc   8700
ggtgatgacg ttctcggagg aggccatggt ggcgaccggt ttgcgcttct tcttgggtgg   8760
ggtgggatct cccatggtgg cctgaatctc aacttgcacc tgaaggtagt gcagcaagga   8820
tgagcaaaag ggaagaaccc agaaaagaac gggaaaactt accccaatta gaattgcttg   8880
tcgccgccag tgtcaacttg caactgaaac aatatccaac atgaacgtca atttatactg   8940
ccctaatggc gaacacgata acaatatttc ttttattatg ccctctaaaa ccaacgcggt   9000
tatcgtttat ttattcaaat tagatataga acatccgccg acatacaatg ttaatgcaaa   9060
aacgcgtttg gtgagcggat acgaaaacag tcggccgata aacattaatc tgaggtcgat   9120
aacaccgtcc ttgaacggaa cacgaggagc gtacgtgatc agctgcattc gcgcgccgcg   9180
cctttatcga gatttatttg catacaacaa gtacactgcg ccgttgggat ttgtggtaac   9240
gcgcacacat gcagagctgc aagtgtggca cattttgtct gtgcgcaaaa cctttgaagc   9300
caaaagtacg aggtccgtta cgggcatgct agcgcacacg gacaatggac ccgacaaatt   9360
ctacgccaag gatttaatga taatgtcggg caacgtatcc gttcatttta tcaataacct   9420
acaaaaatgt cgcgcgcatc acaaagacat cgatatattt aaacatttat gtcccgaact   9480
gcaaatcgat aatagtgttg tgcaacctcg agcgtccgtt tgatttaacg tatagcttgc   9540
aaatgaatta tttaattatc aatcatgttt tacgcgtaga attctacccg taaagcgagt   9600
ttagttatga gccatgtgca aaacatgaca tcagctttta tttttataac aaatgacatc   9660
atttcttgat tgtgttttac acgtagaatt ctactcgtaa agcgagttca gttttgaaaa   9720
acaaatgaca tcatcttttt gattgtgctt tacaagtaga attctacccg taaatcaagt   9780
tcggttttga aaaacaaatg agtcatattg tatgatatca tattgcaaaa caaatgactc   9840
atcaatcgat cgtgcgttac acgtagaatt ctactcgtaa agcgagttta tgagccgtgt   9900
gcaaaacatg acatcatctc gatttgaaaa acaaatgaca tcatccactg atcgtgcatt   9960
```

-continued acaagtagaa ttctactcgt aaagccagtt cggttatgag ccgtgtacaa aacatgacat 10020
cagattatga ctcatacttg attgtgtttt acgcgtagaa ttctactcgt aaagccagtt 10080
caattttaaa aacaaatgac atcatccaaa ttaataaatg acaagcaatg ggtaccatgc 10140

<210> SEQ ID NO 21
<211> LENGTH: 10522
<212> TYPE: DNA
<213> ORGANISM: Artificial
<220> FEATURE:
<223> OTHER INFORMATION: pLA1124

<400> SEQUENCE: 21
gtggtttttg tcaaacgaag attctatgac gtgtttaaag tttaggtcga gtaaagcgca 60
aatctttttt aaccctagaa agatagtctg cgtaaaattg acgcatgcat tcttgaaata 120
ttgctctctc tttctaaata gcgcgaatcc gtcgctgtgc atttaggaca tctcagtcgc 180
cgcttggagc tcccgtgagg cgtgcttgtc aatgcggtaa gtgtcactga ttttgaacta 240
taacgaccgc gtgagtcaaa atgacgcatg attatctttt acgtgacttt taagatttaa 300
ctcatacgat aattatattg ttatttcatg ttctacttac gtgataactt attatatata 360
tattttcttg ttatagatat cgtgactaat atataataaa atgggtagtt ctttagacga 420
tgagcatatc ctctctgctc ttctgcaaag cgatgacgag cttgttggtg aggattctga 480
cagtgaaata tcagatcacg taagtgaaga tgacgtccag agcgatacag aagaagcgtt 540
tatagatgag gtacatgaag tgcagccaac gtcaagcggt agtgaaatat tagacgaaca 600
aaatgttatt gaacaaccag gttcttcatt ggcttctaac agaatcttga ccttgccaca 660
gaggactatt agaggtaaga ataaacattg ttggtcaact tcaaagtcca cgaggcgtag 720
ccgagtctct gcactgaaca ttgtcagatc ggcccgggcg ccgtttttct tgaaatattg 780
ctctctcttt ctaaatagcg cgaatccgtc gctgtgcatt taggacatct cagtcgccgc 840
ttggagctcc caaacgcgcc agtggtagta cacagtactg tgggtgttca gtttgaaatc 900
ctcttgcttc tccattgtct cggttacctt tggtcaaatc catgggttct attgcctata 960
tactcttgcg attaccagtg attgcgctat tagctattag atggattgtt ggccaaactt 1020
gtcgcttaag tggctgggaa ttgtaaccgt aggcccgagt gtaatgatcc cccataaaaa 1080
gttttcgcaa tgcctttatt ttttgttgca aatctctctt tattctgcgg tattcttcat 1140
tattgcgggg atggggaaag tgtttatata gaagcaactt acgattgaac ccaaatgcac 1200
ctgacaagca aggtcaaagg gccagatttt taaatatatt atttagtctt aggactctct 1260
atttgcaatt aaattacttt gctacctgag ggttaaatct tccccattga taataataat 1320
tccactatat gttcaattgg gtttcaccgc gcttagttac atgacgagcc ctaatgagcc 1380
gtcggtggtc tataaactgt gccttacaaa tacttgcaac tcttctcgtt ttgaagtcag 1440
cagagttatt gctaattgct aattgctaat tgcttttaac tgatttcttc gaaattggtg 1500
ctatgtttat ggcgctatta acaagtatga atgtcaggtt taaccagggg atgcttaatt 1560
gtgttctcaa cttcaaaggc agaaatgttt actcttgacc atgggtttag gtataatgtt 1620
atcaagctcc tcgagttaac gttacgttaa cgttaacgtt cgaggtcgac tctagaacta 1680
cccaccgtac tcgtcaattc caagggcatc ggtaaacatc tgctcaaact cgaagtcggc 1740
catatccaga gcgccgtagg gggcggagtc gtggggggta aatcccggac ccggggaatc 1800
cccgtccccc aacatgtcca gatcgaaatc gtctagcgcg tcggcatgcg ccatcgccac 1860
gtcctcgccg tctaagtgga gctcgtcccc caggctgaca tcggtcgggg gggccgtcga 1920

-continued

```
cagtctgcgc gtgtgtcccg cggggagaaa ggacaggcgc ggagccgcca gccccgcctc   1980
ttcgggggcg tcgtcgtccg ggagatcgag caggccctcg atggtagacc cgtaattgtt   2040
tttcgtacgc gcgcggctgt acgcggggcc cgagcccgac tcgcatttca gttgcttttc   2100
caatccgcag ataatcagct ccaagccgaa caggaatgcc ggctcggctc cttgatgatc   2160
gaacagctcg attgcctgac gcagcagtgg gggcatcgaa tcggttgttg gggtctcgcg   2220
ctcctctttt gcgacttgat gctcttggtc ctccagcacg cagcccaggg taaagtgacc   2280
gacggcgctc agagcgtaga gagcattttc caggctgaag ccttgctggc acaggaacgc   2340
gagctggttc tccagtgtct cgtattgctt ttcggtcggg cgcgtgccga gatggacttt   2400
ggcaccgtct cggtgggaca gcagagcgca gcggaacgac ttggcgttat tgcggaggaa   2460
gtcctgccag gactcgcctt ccaacgggca aaaatgcgtg tggtggcggt cgagcatctc   2520
gatggccagg gcatccagca gcgcccgctt attcttcacg tgccagtaga gggtgggctg   2580
ctccacgccc agcttctgcg ccaacttgcg ggtcgtcagt ccctcaatgc caacttcgtt   2640
caacagctcc aacgcggagt tgatgacttt ggacttatcc aggcggctgc ccatggtggt   2700
ttctaaaggt gttataaatc aaattagttt tgtttttttct tgaaaacttt gcgtttcctt   2760
tgatcaactt accgccaggg taccgcagat tgtttagctt gttcagctgc gcttgtttat   2820
ttgcttagct ttcgcttagc gacgtgttca ctttgcttgt ttgaattgaa ttgtcgctcc   2880
gtagacgaag cgcctctatt tatactccgg cgctcgtttt cgagtttacc actccctatc   2940
agtgatagag aaaagtgaaa gtcgagttta ccactcccta tcagtgatag agaaaagtga   3000
aagtcgagtt taccactccc tatcagtgat agagaaaagt gaaagtcgag tttaccactc   3060
cctatcagtg atagagaaaa gtgaaagtcg agtttaccac tccctatcag tgatagagaa   3120
aagtgaaagt cgagtttacc actccctatc agtgatagag aaaagtgaaa gtcgagttta   3180
ccactcccta tcagtgatag agaaaagtga aagtcgaaac ctggcgcgcc ccggccatcg   3240
agaaagagag agagaagaga agagagagaa cattcgagaa agagagagag aagagaagag   3300
agagaacata ctccctatca gtgatagaga agtccctatc agtgatagag atgtccctat   3360
cagtgataga gagttcccta tcagtgatag agacgtccct atcagtgata gagaagtccc   3420
tatcagtgat agagagatcc ctatcagtga tagagatttc cctatcagtg atagagaggt   3480
ccctatcagt gatagagact tccctatcag tgatagagaa atccctatca gtgatagaga   3540
catccctatc agtgatagag aactccctat cagtgataga gacctcccta tcagtgatag   3600
agatcgatgc ggccgcatgg tacccattgc ttgtcattta ttaatttgga tgatgtcatt   3660
tgtttttaaa attgaactgg ctttacgagt agaattctac gcgtaaaaca caatcaagta   3720
tgagtcataa tctgatgtca tgttttgtac acggctcata accgaactgg ctttacgagt   3780
agaattctac ttgtaatgca cgatcagtgg atgatgtcat ttgtttttca aatcgagatg   3840
atgtcatgtt ttgcacacgg ctcataaact cgctttacga gtagaattct acgtgtaacg   3900
cacgatcgat tgatgagtca tttgttttgc aatatgatat catacaatat gactcatttg   3960
tttttcaaaa ccgaacttga tttacgggta gaattctact tgtaaagcac aatcaaaaag   4020
atgatgtcat ttgtttttca aaactgaact cgctttacga gtagaattct acgtgtaaaa   4080
cacaatcaag aaatgatgtc atttgttata aaaataaaag ctgatgtcat gttttgcaca   4140
tggctcataa ctaaactcgc tttacgggta gaattctacg cgtaaaacat gattgataat   4200
taaataattc atttgcaagc tatacgttaa atcaaacgga cgctcgaggt tgcacaacac   4260
```

-continued

```
tattatcgat ttgcagttcg ggacataaat gtttaaatat atcgatgtct ttgtgatgcg   4320
cgcgacattt ttgtaggtta ttgataaaat gaacggatac gttgcccgac attatcatta   4380
aatccttggc gtagaatttg tcgggtccat tgtccgtgtg cgctagcatg cccgtaacgg   4440
acctcgtact tttggcttca aaggttttgc gcacagacaa aatgtgccac acttgcagct   4500
ctgcatgtgt gcgcgttacc acaaatccca acggcgcagt gtacttgttg tatgcaaata   4560
aatctcgata aaggcgcggc gcgcgaatgc agctgatcac gtacgctcct cgtgttccgt   4620
tcaaggacgg tgttatcgac ctcagattaa tgtttatcgg ccgactgttt tcgtatccgc   4680
tcaccaaacg cgtttttgca ttaacattgt atgtcggcgg atgttctata tctaatttga   4740
ataaataaac gataaccgcg ttggttttag agggcataat aaaagaaata ttgttatcgt   4800
gttcgccatt agggcagtat aaattgacgt tcatgttgga tattgtttca gttgcaagtt   4860
gacactggcg gcgacaagca attctaattg gggtaagttt tcccgttctt ttctgggttc   4920
ttccctttg ctcatccttg ctgcactacc ttcaggtgca agttgagatt caggccacca   4980
tgggagatcc caccccaccc aagaagaagc gcaaaccggt cgccaccatg gcctcctccg   5040
agaacgtcat caccgagttc atgcgcttca aggtgcgcat ggagggcacc gtgaacggcc   5100
acgagttcga gatcgagggc gagggcgagg gccgccccta cgagggccac aacaccgtga   5160
agctgaaggt gaccaagggc ggcccctgc ccttcgcctg ggacatcctg tccccccagt   5220
tccagtacgg ctccaaggtg tacgtgaagc accccgccga catccccgac tacaagaagc   5280
tgtccttccc cgagggcttc aagtgggagc gcgtgatgaa cttcgaggac ggcggcgtgg   5340
cgaccgtgac ccaggactcc tccctgcagg acggctgctt catctacaag gtgaagttca   5400
tcggcgtgaa cttcccctcc gacggccccg tgatgcagaa gaagaccatg ggctgggagg   5460
cctccaccga gcgcctgtac ccccgcgacg gcgtgctgaa gggcgagacc cacaaggccc   5520
tgaagctgaa ggacggcggc cactacctgg tggagttcaa gtccatctac atggccaaga   5580
agcccgtgca gctgcccggc tactactacg tggacgccaa gctggacatc acctcccaca   5640
acgaggacta caccatcgtg gagcagtacg agcgcaccga gggccgccac cacctgttcc   5700
tgagatctcg acccaagaaa aagcggaagg tggaggaccc gtaagatcca ccggatctag   5760
ataactgatc ataatcagcc ataccacatt tgtagaggtt ttacttgctt taaaaaacct   5820
cccacacctc cccctgaacc tgaaacataa aatgaatgca attgttgttg ttaacttgtt   5880
tattgcagct tataatggtt acaaataaag caatagcatc acaaatttca caaataaagc   5940
atttttttca ctgcattcta gttgtggttt gtccaaactc atcaatgtat cttaacgcga   6000
gttaattaag gccgctcatt taaatctggc cggccgcaac cattgtggga accgtgcgat   6060
caaacaaacg cgagataccg gaagtactga aaaacagtcg ctccaggcca gtgggaacat   6120
cgatgttttg ttttgacgga ccccttactc tcgtctcata taaaccgaag ccagctaaga   6180
tggtatactt attatcatct tgtgatgagg atgcttctat caacgaaagt accggtaaac   6240
cgcaaatggt tatgtattat aatcaaacta aaggcggagt ggacacgcta gaccaaatgt   6300
gttctgtgat gacctgcagt aggaagacga ataggtggcc tatggcatta ttgtacggaa   6360
tgataaacat tgcctgcata aattctttta ttatatacag ccataatgtc agtagcaagg   6420
gagaaaaggt ccaaagtcgc aaaaaattta tgagaaacct ttacatgagc ctgacgtcat   6480
cgtttatgcg taagcgttta gaagctccta ctttgaagag atatttgcgc gataatatct   6540
ctaatatttt gccaaatgaa gtgcctggta catcagatga cagtactgaa gagccagtaa   6600
tgaaaaaacg tacttactgt acttactgcc cctctaaaat aaggcgaaag gcaaatgcat   6660
```

-continued cgtgcaaaaa atgcaaaaaa gttatttgtc gagagcataa tattgatatg tgccaaagtt 6720
gtttctgact gactaataag tataatttgt ttctattatg tataagttaa gctaattact 6780
tattttataa tacaacatga ctgtttttaa agtacaaaat aagtttattt ttgtaaaaga 6840
gagaatgttt aaaagttttg ttactttata gaagaaattt tgagtttttg ttttttttta 6900
ataaataaat aaacataaat aaattgtttg ttgaatttat tattagtatg taagtgtaaa 6960
tataataaaa cttaatatct attcaaatta ataaataaac ctcgatatac agaccgataa 7020
aacacatgcg tcaattttac gcatgattat ctttaacgta cgtcacaata tgattatctt 7080
tctagggtta aataatagtt tctaattttt ttattattca gcctgctgtc gtgaataccg 7140
tatatctcaa cgctgtctgt gagattgtcg tattctagcc tttttagttt ttcgctcatc 7200
gacttgatat tgtccgacac attttcgtcg atttgcgttt tgatcaaaga cttgagcaga 7260
gacacgttaa tcaactgttc aaattgatcc atattaacga tatcaacccg atgcgtatat 7320
ggtgcgtaaa atatattttt taaccctctt atactttgca ctctgcgtta atacgcgttc 7380
gtgtacagac gtaatcatgt tttctttttt ggataaaact cctactgagt ttgacctcat 7440
attagaccct cacaagttgc aaaacgtggc atttttacc aatgaagaat ttaaagttat 7500
tttaaaaaat ttcatcacag atttaaagaa gaaccaaaaa ttaaattatt tcaacagttt 7560
aatcgaccag ttaatcaacg tgtacacaga cgcgtcggca aaaaacacgc agcccgacgt 7620
gttggctaaa attattaaat caacttgtgt tatagtcacg gatttgccgt ccaacgtgtt 7680
cctcaaaaag ttgaagacca acaagtttac ggacactatt aattatttga ttttgcccca 7740
cttcattttg tgggatcaca attttgttat attttaaaca aagcttggca ctggccgtcg 7800
ttttacaacg tcgtgactgg gaaaaccctg gcgttaccca acttaatcgc cttgcagcac 7860
atcccccttt cgccagctgg cgtaatagcg aagaggcccg caccgatcgc ccttcccaac 7920
agttgcgcag cctgaatggc gaatggcgcc tgatgcggta ttttctcctt acgcatctgt 7980
gcggtatttc acaccgcata tggtgcactc tcagtacaat ctgctctgat gccgcatagt 8040
taagccagcc ccgacacccg ccaacacccg ctgacgcgcc ctgacgggct tgtctgctcc 8100
cggcatccgc ttacagacaa gctgtgaccg tctccgggag ctgcatgtgt cagaggtttt 8160
caccgtcatc accgaaacgc gcgagacgaa agggcctcgt gatacgccta tttttatagg 8220
ttaatgtcat gataataatg gtttcttaga cgtcaggtgg cacttttcgg ggaaatgtgc 8280
gcggaacccc tatttgttta tttttctaaa tacattcaaa tatgtatccg ctcatgagac 8340
aataaccctg ataaatgctt caataatatt gaaaaaggaa gagtatgagt attcaacatt 8400
tccgtgtcgc ccttattccc ttttttgcgg cattttgcct tcctgttttt gctcacccag 8460
aaacgctggt gaaagtaaaa gatgctgaag atcagttggg tgcacgagtg ggttacatcg 8520
aactggatct caacagcggt aagatccttg agagttttcg ccccgaagaa cgttttccaa 8580
tgatgagcac ttttaaagtt ctgctatgtg gcgcggtatt atcccgtatt gacgccgggc 8640
aagagcaact cggtcgccgc atacactatt ctcagaatga cttggttgag tactcaccag 8700
tcacagaaaa gcatcttacg gatggcatga cagtaagaga attatgcagt gctgccataa 8760
ccatgagtga taacactgcg gccaacttac ttctgacaac gatcggagga ccgaaggagc 8820
taaccgcttt tttgcacaac atgggggatc atgtaactcg ccttgatcgt tgggaaccgg 8880
agctgaatga agccatacca aacgacgagc gtgacaccac gatgcctgta gcaatggcaa 8940
caacgttgcg caaactatta actggcgaac tacttactct agcttcccgg caacaattaa 9000

-continued

```
tagactggat ggaggcggat aaagttgcag gaccacttct gcgctcggcc cttccggctg   9060

gctggtttat tgctgataaa tctggagccg gtgagcgtgg gtctcgcggt atcattgcag   9120

cactggggcc agatggtaag ccctcccgta tcgtagttat ctacacgacg gggagtcagg   9180

caactatgga tgaacgaaat agacagatcg ctgagatagg tgcctcactg attaagcatt   9240

ggtaactgtc agaccaagtt tactcatata tactttagat tgatttaaaa cttcattttt   9300

aatttaaaag gatctaggtg aagatccttt ttgataatct catgaccaaa atcccttaac   9360

gtgagttttc gttccactga gcgtcagacc ccgtagaaaa gatcaaagga tcttcttgag   9420

atcctttttt tctgcgcgta atctgctgct tgcaaacaaa aaaaccaccg ctaccagcgg   9480

tggtttgttt gccggatcaa gagctaccaa ctctttttcc gaaggtaact ggcttcagca   9540

gagcgcagat accaaatact gtccttctag tgtagccgta gttaggccac cacttcaaga   9600

actctgtagc accgcctaca tacctcgctc tgctaatcct gttaccagtg gctgctgcca   9660

gtggcgataa gtcgtgtctt accgggttgg actcaagacg atagttaccg gataaggcgc   9720

agcggtcggg ctgaacgggg ggttcgtgca cacagcccag cttggagcga acgacctaca   9780

ccgaactgag atacctacag cgtgagcatt gagaaagcgc cacgcttccc gaagggagaa   9840

aggcggacag gtatccggta agcggcaggg tcggaacagg agagcgcacg agggagcttc   9900

caggggggaaa cgcctggtat ctttatagtc ctgtcgggtt tcgccacctc tgacttgagc   9960

gtcgattttt gtgatgctcg tcaggggggc ggagcctatg gaaaaacgcc agcaacgcgg  10020

cctttttacg gttcctggcc ttttgctggc cttttgctca catgttcttt cctgcgttat  10080

cccctgattc tgtggataac cgtattaccg cctttgagtg agctgatacc gctcgccgca  10140

gccgaacgac cgagcgcagc gagtcagtga gcgaggaagc ggaagagcgc ccaatacgca  10200

aaccgcctct ccccgcgcgt tggccgattc attaatgcag ctggcacgac aggtttcccg  10260

actggaaagc gggcagtgag cgcaacgcaa ttaatgtgag ttagctcact cattaggcac  10320

cccaggcttt acactttatg cttccggctc gtatgttgtg tggaattgtg agcggataac  10380

aatttcacac aggaaacagc tatgaccatg attacgaatt tcgacctgca ggcatgcaag  10440

cttgcatgcc tgcaggtcga cgctcgcgcg acttggtttg ccattcttta gcgcgcgtcg  10500

cgtcacacag cttggccaca at                                           10522
```

```
<210> SEQ ID NO 22
<211> LENGTH: 11867
<212> TYPE: DNA
<213> ORGANISM: Artificial
<220> FEATURE:
<223> OTHER INFORMATION: pLA1188

<400> SEQUENCE: 22

gtggtttttg tcaaacgaag attctatgac gtgtttaaag tttaggtcga gtaaagcgca     60

aatctttttt aaccctagaa agatagtctg cgtaaaattg acgcatgcat tcttgaaata    120

ttgctctctc tttctaaata gcgcgaatcc gtcgctgtgc atttaggaca tctcagtcgc    180

cgcttggagc tcccgtgagg cgtgcttgtc aatgcggtaa gtgtcactga ttttgaacta    240

taacgaccgc gtgagtcaaa atgacgcatg attatctttt acgtgacttt taagatttaa    300

ctcatacgat aattatattg ttatttcatg ttctacttac gtgataactt attatatata    360

tattttcttg ttatagatat cgtgactaat atataataaa atgggtagtt ctttagacga    420

tgagcatatc ctctctgctc ttctgcaaag cgatgacgag cttgttggtg aggattctga    480

cagtgaaata tcagatcacg taagtgaaga tgacgtccag agcgatacag aagaagcgtt    540
```

-continued

```
tatagatgag gtacatgaag tgcagccaac gtcaagcggt agtgaaatat tagacgaaca    600
aaatgttatt gaacaaccag gttcttcatt ggcttctaac agaatcttga ccttgccaca    660
gaggactatt agaggtaaga ataaacattg ttggtcaact tcaaagtcca cgaggcgtag    720
ccgagtctct gcactgaaca ttgtcagatc ggcccgggcg ccgtttttct tgaaatattg    780
ctctctcttt ctaaatagcg cgaatccgtc gctgtgcatt taggacatct cagtcgccgc    840
ttggagctcc caaacgcgcc agtggtagta cacagtactg tgggtgttca gtttgaaatc    900
ctcttgcttc tccattgtct cggttacctt tggtcaaatc catgggttct attgcctata    960
tactcttgcg attaccagtg attgcgctat tagctattag atggattgtt ggccaaactt   1020
gtcgcttaag tggctgggaa ttgtaaccgt aggcccgagt gtaatgatcc cccataaaaa   1080
gttttcgcaa tgcctttatt ttttgttgca aatctctctt tattctgcgg tattcttcat   1140
tattgcgggg atggggaaag tgtttatata gaagcaactt acgattgaac ccaaatgcac   1200
ctgacaagca aggtcaaagg gccagatttt taaatatatt atttagtctt aggactctct   1260
atttgcaatt aaattacttt gctacctgag ggttaaatct tccccattga taataataat   1320
tccactatat gttcaattgg gtttcaccgc gcttagttac atgacgagcc ctaatgagcc   1380
gtcggtggtc tataaactgt gccttacaaa tacttgcaac tcttctcgtt ttgaagtcag   1440
cagagttatt gctaattgct aattgctaat tgcttttaac tgatttcttc gaaattggtg   1500
ctatgtttat ggcgctatta acaagtatga atgtcaggtt taaccagggg atgcttaatt   1560
gtgttctcaa cttcaaaggc agaaatgttt actcttgacc atgggtttag gtataatgtt   1620
atcaagctcc tcgagttaac gttacgttaa cgttaacgtt cgaggtcgac tctagaacta   1680
cccaccgtac tcgtcaattc caagggcatc ggtaaacatc tgctcaaact cgaagtcggc   1740
catatccaga gcgccgtagg gggcggagtc gtggggggta aatcccggac ccggggaatc   1800
cccgtccccc aacatgtcca gatcgaaatc gtctagcgcg tcggcatgcg ccatcgccac   1860
gtcctcgccg tctaagtgga gctcgtcccc caggctgaca tcggtcgggg gggccgtcga   1920
cagtctgcgc gtgtgtcccg cggggagaaa ggacaggcgc ggagccgcca gccccgcctc   1980
ttcgggggcg tcgtcgtccg ggagatcgag caggccctcg atggtagacc cgtaattgtt   2040
tttcgtacgc gcgcggctgt acgcggggcc cgagcccgac tcgcatttca gttgcttttc   2100
caatccgcag ataatcagct ccaagccgaa caggaatgcc ggctcggctc cttgatgatc   2160
gaacagctcg attgcctgac gcagcagtgg gggcatcgaa tcggttgttg gggtctcgcg   2220
ctcctctttt gcgacttgat gctcttggtc ctccagcacg cagcccaggg taaagtgacc   2280
gacggcgctc agagcgtaga gagcattttc caggctgaag ccttgctggc acaggaacgc   2340
gagctggttc tccagtgtct cgtattgctt ttcggtcggg cgcgtgccga gatggacttt   2400
ggcaccgtct cggtgggaca gcagagcgca gcggaacgac ttggcgttat tgcggaggaa   2460
gtcctgccag gactcgcctt ccaacgggca aaaatgcgtg tggtggcggt cgagcatctc   2520
gatggccagg gcatccagca gcgcccgctt attcttcacc tatagatacc atagatgtat   2580
ggattagtat catatacata caaaggctat ttttgggaca tattaatatt aacaatttcc   2640
gtgatagttt tcaccatttt tgttgaatgt tacgttgaaa atttaaattt gttttaaatt   2700
aattttacca gtcatgtgtt cttaaaagtt tttatgattg aaacggcata aagtggttca   2760
aaaatttatc aagaaaggct ttcctttttt aaatcttatc tttttctctt aaaaatcact   2820
agtcaattca ttattaattt gttaacttga atttggaatg tctatttact ttcagataaa   2880
```

-continued

```
ttaaagcaag aaacttaata ttcgaaaaaa attgattcta aatggaattt cacttgatct   2940
tcatgtatgc atatcaattt ttatttacat tgtataataa gtttcgagtt gattgttgta   3000
atccacaggt gtcccagaga attaaattcc aaattaccca agtttattga atgttgattg   3060
tagtttcagt tgctttgttg ctgcaacaat ggcttgttga ttgtagatat tttccctttc   3120
cttggtttac ttattacata gactgaaaaa gaggtttact tttttgatac ttatgaaaaa   3180
tttctattag tgattactaa ccaatcgcta tatgtttact agaaaacaaa taaactcttt   3240
acattaacat tcaataatgt ttgctctgta accgacaatt gaaggcgtta cagcaacagt   3300
aatataacta gcttcttaac cctcatctat taaccccatc gtttaaaaca ctatgttaaa   3360
tggtctaaca aatctagata ctaatagatg tcttattact tagcagccac agctgcaaca   3420
tccaagacaa tttttgaaac ttcttattga gctcttggca gcagaaatgt tggtattttt   3480
cacagctttc tgaaagaccg gcaccttcct ccggttcccg tttctgaatt caagaggatt   3540
tccgaccccc aattaatccc gaaacaaata aggtatattc aaaatgatgg aaaagtcatg   3600
gctgctgacc ttatttttat tcctattgat agaatattat tccccttta aatacactgt   3660
actaagaggt ccggctataa ttttactcac ttgtcgatta tcccatagaa tgttgattgt   3720
agttggttgc ttttccaggt gagagttgat caagtcacaa aagttagcgt gtgttgattg   3780
tagatttgaa ggtaaaataa tttttgcacc cattcatcgg gtaaaacgtt ctccatagaa   3840
tacatttcca tcgataattg ataacttatg aatttcaaag aaaaaaatat gcttttaaaa   3900
ttacgtgcca gtagagggtg ggctgctcca cgcccagctt ctgcgccaac ttgcgggtcg   3960
tcagtccctc aatgccaact tcgttcaaca gctccaacgc ggagttgatg actttggact   4020
tatccaggcg gctgcccatg gtggtttcta aaggtgttat aaatcaaatt agttttgttt   4080
tttcttgaaa actttgcgtt tcctttgatc aacttaccgc cagggtaccg cagattgttt   4140
agcttgttca gctgcgcttg tttatttgct tagctttcgc ttagcgacgt gttcactttg   4200
cttgtttgaa ttgaattgtc gctccgtaga cgaagcgcct ctatttatac tccggcgctc   4260
gttttcgagt ttaccactcc ctatcagtga tagagaaaag tgaaagtcga gtttaccact   4320
ccctatcagt gatagagaaa agtgaaagtc gagtttacca ctccctatca gtgatagaga   4380
aaagtgaaag tcgagtttac cactccctat cagtgataga gaaaagtgaa agtcgagttt   4440
accactccct atcagtgata gagaaaagtg aaagtcgagt ttaccactcc ctatcagtga   4500
tagagaaaag tgaaagtcga gtttaccact ccctatcagt gatagagaaa agtgaaagtc   4560
gaaacctggc gcgccccggc catcgagaaa gagagagaga agagaagaga gagaacattc   4620
gagaaagaga gagagaagag aagagagaga acatactccc tatcagtgat agagaagtcc   4680
ctatcagtga tagagatgtc cctatcagtg atagagagtt ccctatcagt gatagagacg   4740
tccctatcag tgatagagaa gtccctatca gtgatagaga gatccctatc agtgatagag   4800
atttccctat cagtgataga gaggtcccta tcagtgatag agacttccct atcagtgata   4860
gagaaatccc tatcagtgat agagacatcc ctatcagtga tagagaactc cctatcagtg   4920
atagagacct ccctatcagt gatagagatc gatgcggccg catggtaccc attgcttgtc   4980
atttattaat ttggatgatg tcatttgttt ttaaaattga actggcttta cgagtagaat   5040
tctacgcgta aaacacaatc aagtatgagt cataatctga tgtcatgttt tgtacacggc   5100
tcataaccga actggcttta cgagtagaat tctacttgta atgcacgatc agtggatgat   5160
gtcatttgtt tttcaaatcg agatgatgtc atgttttgca cacggctcat aaactcgctt   5220
tacgagtaga attctacgtg taacgcacga tcgattgatg agtcatttgt tttgcaatat   5280
```

gatatcatac aatatgactc atttgttttt caaaaccgaa cttgatttac gggtagaatt 5340
ctacttgtaa agcacaatca aaaagatgat gtcatttgtt tttcaaaact gaactcgctt 5400
tacgagtaga attctacgtg taaaacacaa tcaagaaatg atgtcatttg ttataaaaat 5460
aaaagctgat gtcatgtttt gcacatggct cataactaaa ctcgctttac gggtagaatt 5520
ctacgcgtaa aacatgattg ataattaaat aattcatttg caagctatac gttaaatcaa 5580
acggacgctc gaggttgcac aacactatta tcgatttgca gttcgggaca taaatgttta 5640
aatatatcga tgtctttgtg atgcgcgcga catttttgta ggttattgat aaaatgaacg 5700
gatacgttgc ccgacattat cattaaatcc ttggcgtaga atttgtcggg tccattgtcc 5760
gtgtgcgcta gcatgcccgt aacggacctc gtacttttgg cttcaaaggt tttgcgcaca 5820
gacaaaatgt gccacacttg cagctctgca tgtgtgcgcg ttaccacaaa tcccaacggc 5880
gcagtgtact tgttgtatgc aaataaatct cgataaaggc gcggcgcgcg aatgcagctg 5940
atcacgtacg ctcctcgtgt tccgttcaag gacggtgtta tcgacctcag attaatgttt 6000
atcggccgac tgttttcgta tccgctcacc aaacgcgttt ttgcattaac attgtatgtc 6060
ggcggatgtt ctatatctaa tttgaataaa taaacgataa ccgcgttggt tttagagggc 6120
ataataaaag aaatattgtt atcgtgttcg ccattagggc agtataaatt gacgttcatg 6180
ttggatattg tttcagttgc aagttgacac tggcggcgac aagcaattct aattggggta 6240
agttttcccg ttcttttctg ggttcttccc ttttgctcat ccttgctgca ctaccttcag 6300
gtgcaagttg agattcaggc caccatggga gatcccaccc cacccaagaa gaagcgcaaa 6360
ccggtcgcca ccatggcctc ctccgagaac gtcatcaccg agttcatgcg cttcaaggtg 6420
cgcatggagg gcaccgtgaa cggccacgag ttcgagatcg agggcgaggg cgagggccgc 6480
ccctacgagg gccacaacac cgtgaagctg aaggtgacca agggcggccc cctgcccttc 6540
gcctgggaca tcctgtcccc ccagttccag tacggctcca aggtgtacgt gaagcacccc 6600
gccgacatcc ccgactacaa gaagctgtcc ttccccgagg gcttcaagtg ggagcgcgtg 6660
atgaacttcg aggacggcgg cgtggcgacc gtgacccagg actcctccct gcaggacggc 6720
tgcttcatct acaaggtgaa gttcatcggc gtgaacttcc cctccgacgg ccccgtgatg 6780
cagaagaaga ccatgggctg ggaggcctcc accgagcgcc tgtacccccg cgacggcgtg 6840
ctgaagggcg agacccacaa ggccctgaag ctgaaggacg gcggccacta cctggtggag 6900
ttcaagtcca tctacatggc caagaagccc gtgcagctgc ccggctacta ctacgtggac 6960
gccaagctgg acatcacctc ccacaacgag gactacacca tcgtggagca gtacgagcgc 7020
accgagggcc gccaccacct gttcctgaga tctcgaccca agaaaaagcg gaaggtggag 7080
gacccgtaag atccaccgga tctagataac tgatcataat cagccatacc acatttgtag 7140
aggttttact tgctttaaaa aacctcccac acctccccct gaacctgaaa cataaaatga 7200
atgcaattgt tgttgttaac ttgtttattg cagcttataa tggttacaaa taaagcaata 7260
gcatcacaaa tttcacaaat aaagcatttt tttcactgca ttctagttgt ggtttgtcca 7320
aactcatcaa tgtatcttaa cgcgagttaa ttaaggccgc tcatttaaat ctggccggcc 7380
gcaaccattg tgggaaccgt gcgatcaaac aaacgcgaga taccggaagt actgaaaaac 7440
agtcgctcca ggccagtggg aacatcgatg ttttgttttg acggacccct tactctcgtc 7500
tcatataaac cgaagccagc taagatggta tacttattat catcttgtga tgaggatgct 7560
tctatcaacg aaagtaccgg taaaccgcaa atggttatgt attataatca aactaaaggc 7620

```
ggagtggaca cgctagacca aatgtgttct gtgatgacct gcagtaggaa gacgaatagg   7680
tggcctatgg cattattgta cggaatgata aacattgcct gcataaattc ttttattata   7740
tacagccata atgtcagtag caagggagaa aaggtccaaa gtcgcaaaaa atttatgaga   7800
aacctttaca tgagcctgac gtcatcgttt atgcgtaagc gtttagaagc tcctactttg   7860
aagagatatt tgcgcgataa tatctctaat attttgccaa atgaagtgcc tggtacatca   7920
gatgacagta ctgaagagcc agtaatgaaa aaacgtactt actgtactta ctgcccctct   7980
aaaataaggc gaaaggcaaa tgcatcgtgc aaaaaatgca aaaaagttat ttgtcgagag   8040
cataatattg atatgtgcca aagttgtttc tgactgacta ataagtataa tttgtttcta   8100
ttatgtataa gttaagctaa ttacttattt tataatacaa catgactgtt tttaaagtac   8160
aaaataagtt tatttttgta aaagagagaa tgtttaaaag ttttgttact ttatagaaga   8220
aattttgagt ttttgttttt ttttaataaa taaataaaca taaataaatt gtttgttgaa   8280
tttattatta gtatgtaagt gtaaatataa taaaacttaa tatctattca aattaataaa   8340
taaacctcga tatacagacc gataaaacac atgcgtcaat tttacgcatg attatcttta   8400
acgtacgtca caatatgatt atctttctag ggttaaataa tagtttctaa ttttttttatt   8460
attcagcctg ctgtcgtgaa taccgtatat ctcaacgctg tctgtgagat tgtcgtattc   8520
tagcctttttt agtttttcgc tcatcgactt gatattgtcc gacacatttt cgtcgatttg   8580
cgttttgatc aaagacttga gcagagacac gttaatcaac tgttcaaatt gatccatatt   8640
aacgatatca acccgatgcg tatatggtgc gtaaaatata ttttttaacc ctcttatact   8700
ttgcactctg cgttaatacg cgttcgtgta cagacgtaat catgttttct tttttggata   8760
aaactcctac tgagtttgac ctcatattag accctcacaa gttgcaaaac gtggcatttt   8820
ttaccaatga agaatttaaa gttattttaa aaaatttcat cacagattta aagaagaacc   8880
aaaaattaaa ttatttcaac agtttaatcg accagttaat caacgtgtac acagacgcgt   8940
cggcaaaaaa cacgcagccc gacgtgttgg ctaaaattat taaatcaact tgtgttatag   9000
tcacggattt gccgtccaac gtgttcctca aaaagttgaa gaccaacaag tttacggaca   9060
ctattaatta tttgattttg ccccacttca ttttgtggga tcacaatttt gttatatttt   9120
aaacaaagct tggcactggc cgtcgtttta caacgtcgtg actgggaaaa ccctggcgtt   9180
acccaactta atcgccttgc agcacatccc cctttcgcca gctggcgtaa tagcgaagag   9240
gcccgcaccg atcgcccttc ccaacagttg cgcagcctga atggcgaatg gcgcctgatg   9300
cggtattttc tccttacgca tctgtgcggt atttcacacc gcatatggtg cactctcagt   9360
acaatctgct ctgatgccgc atagttaagc cagccccgac acccgccaac acccgctgac   9420
gcgccctgac gggcttgtct gctcccggca tccgcttaca gacaagctgt gaccgtctcc   9480
gggagctgca tgtgtcagag gttttcaccg tcatcaccga aacgcgcgag acgaaagggc   9540
ctcgtgatac gcctattttt ataggttaat gtcatgataa taatggtttc ttagacgtca   9600
ggtggcactt ttcggggaaa tgtgcgcgga acccctattt gtttattttt ctaaatacat   9660
tcaaatatgt atccgctcat gagacaataa ccctgataaa tgcttcaata atattgaaaa   9720
aggaagagta tgagtattca acatttccgt gtcgccctta ttcccttttt tgcggcattt   9780
tgccttcctg tttttgctca cccagaaacg ctggtgaaag taaaagatgc tgaagatcag   9840
ttgggtgcac gagtgggtta catcgaactg gatctcaaca gcggtaagat ccttgagagt   9900
tttcgccccg aagaacgttt tccaatgatg agcactttta aagttctgct atgtggcgcg   9960
gtattatccc gtattgacgc ccggcaagag caactcggtc gccgcataca ctattctcag  10020
```

```
aatgacttgg ttgagtactc accagtcaca gaaaagcatc ttacggatgg catgacagta  10080

agagaattat gcagtgctgc cataaccatg agtgataaca ctgcggccaa cttacttctg  10140

acaacgatcg gaggaccgaa ggagctaacc gctttttgc acaacatggg ggatcatgta  10200

actcgccttg atcgttggga accggagctg aatgaagcca taccaaacga cgagcgtgac  10260

accacgatgc ctgtagcaat ggcaacaacg ttgcgcaaac tattaactgg cgaactactt  10320

actctagctt cccggcaaca attaatagac tggatggagg cggataaagt tgcaggacca  10380

cttctgcgct cggcccttcc ggctggctgg tttattgctg ataaatctgg agccggtgag  10440

cgtgggtctc gcggtatcat tgcagcactg gggccagatg gtaagccctc ccgtatcgta  10500

gttatctaca cgacggggag tcaggcaact atggatgaac gaaatagaca gatcgctgag  10560

ataggtgcct cactgattaa gcattggtaa ctgtcagacc aagtttactc atatatactt  10620

tagattgatt taaaacttca tttttaattt aaaaggatct aggtgaagat cctttttgat  10680

aatctcatga ccaaaatccc ttaacgtgag ttttcgttcc actgagcgtc agaccccgta  10740

gaaaagatca aaggatcttc ttgagatcct ttttttctgc gcgtaatctg ctgcttgcaa  10800

acaaaaaaac caccgctacc agcggtggtt tgtttgccgg atcaagagct accaactctt  10860

tttccgaagg taactggctt cagcagagcg cagataccaa atactgtcct tctagtgtag  10920

ccgtagttag gccaccactt caagaactct gtagcaccgc ctacatacct cgctctgcta  10980

atcctgttac cagtggctgc tgccagtggc gataagtcgt gtcttaccgg gttggactca  11040

agacgatagt taccggataa ggcgcagcgg tcgggctgaa cggggggttc gtgcacacag  11100

cccagcttgg agcgaacgac ctacaccgaa ctgagatacc tacagcgtga gcattgagaa  11160

agcgccacgc ttcccgaagg gagaaaggcg gacaggtatc cggtaagcgg cagggtcgga  11220

acaggagagc gcacgaggga gcttccaggg ggaaacgcct ggtatcttta tagtcctgtc  11280

gggtttcgcc acctctgact tgagcgtcga tttttgtgat gctcgtcagg ggggcggagc  11340

ctatggaaaa acgccagcaa cgcggccttt ttacggttcc tggccttttg ctggcctttt  11400

gctcacatgt tctttcctgc gttatcccct gattctgtgg ataaccgtat taccgccttt  11460

gagtgagctg ataccgctcg ccgcagccga acgaccgagc gcagcgagtc agtgagcgag  11520

gaagcggaag agcgcccaat acgcaaaccg cctctccccg cgcgttggcc gattcattaa  11580

tgcagctggc acgacaggtt tcccgactgg aaagcgggca gtgagcgcaa cgcaattaat  11640

gtgagttagc tcactcatta ggcaccccag gctttacact ttatgcttcc ggctcgtatg  11700

ttgtgtggaa ttgtgagcgg ataacaattt cacacaggaa acagctatga ccatgattac  11760

gaatttcgac ctgcaggcat gcaagcttgc atgcctgcag gtcgacgctc gcgcgacttg  11820

gtttgccatt ctttagcgcg cgtcgcgtca cacagcttgg ccacaat              11867
```

<210> SEQ ID NO 23
<211> LENGTH: 10786
<212> TYPE: DNA
<213> ORGANISM: Artificial
<220> FEATURE:
<223> OTHER INFORMATION: pLA670

<400> SEQUENCE: 23

```
ggccgctcat ttaaatctgg ccggccgcaa ccattgtggg aaccgtgcga tcaaacaaac     60

gcgagatacc ggaagtactg aaaaacagtc gctccaggcc agtgggaaca tcgatgtttt    120

gttttgacgg accccttact ctcgtctcat ataaaccgaa gccagctaag atggtatact    180
```

-continued

```
tattatcatc ttgtgatgag gatgcttcta tcaacgaaag taccggtaaa ccgcaaatgg    240
ttatgtatta taatcaaact aaaggcggag tggacacgct agaccaaatg tgttctgtga    300
tgacctgcag taggaagacg aataggtggc ctatggcatt attgtacgga atgataaaca    360
ttgcctgcat aaattctttt attatataca gccataatgt cagtagcaag ggagaaaagg    420
tccaaagtcg caaaaaattt atgagaaacc tttacatgag cctgacgtca tcgtttatgc    480
gtaagcgttt agaagctcct actttgaaga gatatttgcg cgataaatatc tctaatattt   540
tgccaaatga agtgcctggt acatcagatg acagtactga agagccagta atgaaaaaac    600
gtacttactg tacttactgc ccctctaaaa taaggcgaaa ggcaaatgca tcgtgcaaaa    660
aatgcaaaaa agttatttgt cgagagcata atattgatat gtgccaaagt tgtttctgac    720
tgactaataa gtataatttg tttctattat gtataagtta agctaattac ttattttata    780
atacaacatg actgttttta aagtacaaaa taagtttatt tttgtaaaag agagaatgtt    840
taaaagtttt gttactttat agaagaaatt ttgagttttt gtttttttt aataaataaa    900
taaacataaa taaattgttt gttgaattta ttattagtat gtaagtgtaa atataataaa    960
acttaatatc tattcaaatt aataaataaa cctcgatata cagaccgata aaacacatgc   1020
gtcaatttta cgcatgatta tctttaacgt acgtcacaat atgattatct ttctagggtt   1080
aaataatagt ttctaatttt tttattattc agcctgctgt cgtgaatacc gtatatctca   1140
acgctgtctg tgagattgtc gtattctagc ctttttagtt tttcgctcat cgacttgata   1200
ttgtccgaca cattttcgtc gatttgcgtt ttgatcaaag acttgagcag agacacgtta   1260
atcaactgtt caaattgatc catattaacg atatcaaccc gatgcgtata tggtgcgtaa   1320
aatatatttt ttaaccctct tatactttgc actctgcgtt aatacgcgtt cgtgtacaga   1380
cgtaatcatg ttttcttttt tggataaaac tcctactgag tttgacctca tattagaccc   1440
tcacaagttg caaaacgtgg catttttttac caatgaagaa tttaaagtta ttttaaaaaa   1500
tttcatcaca gatttaaaga agaaccaaaa attaaattat ttcaacagtt taatcgacca   1560
gttaatcaac gtgtacacag acgcgtcggc aaaaaaacacg cagcccgacg tgttggctaa   1620
aattattaaa tcaacttgtg ttatagtcac ggatttgccg tccaacgtgt tcctcaaaaa   1680
gttgaagacc aacaagttta cggacactat taattatttg attttgcccc acttcatttt   1740
gtgggatcac aattttgtta tattttaaac aaagcttggc actggccgtc gttttacaac   1800
gtcgtgactg ggaaaaccct ggcgttaccc aacttaatcg ccttgcagca catccccctt   1860
tcgccagctg gcgtaatagc gaagaggccc gcaccgatcg cccttcccaa cagttgcgca   1920
gcctgaatgg cgaatggcgc ctgatgcggt attttctcct tacgcatctg tgcggtattt   1980
cacaccgcat atggtgcact ctcagtacaa tctgctctga tgccgcatag ttaagccagc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgagacga aagggcctcg tgatacgcct atttttatag gttaatgtca   2220
tgataataat ggtttcttag acgtcaggtg gcacttttcg gggaaatgtg cgcggaaccc   2280
ctatttgttt atttttctaa atacattcaa atatgtatcc gctcatgaga caataaccct   2340
gataaatgct tcaataatat tgaaaaagga agagtatgag tattcaacat ttccgtgtcg   2400
cccttattcc cttttttgcg gcattttgcc ttcctgtttt tgctcaccca gaaacgctgg   2460
tgaaagtaaa agatgctgaa gatcagttgg gtgcacgagt gggttacatc gaactggatc   2520
tcaacagcgg taagatcctt gagagttttc gccccgaaga acgttttcca atgatgagca   2580
```

-continued

```
cttttaaagt tctgctatgt ggcgcggtat tatcccgtat tgacgccggg caagagcaac   2640
tcggtcgccg catacactat tctcagaatg acttggttga gtactcacca gtcacagaaa   2700
agcatcttac ggatggcatg acagtaagag aattatgcag tgctgccata accatgagtg   2760
ataacactgc ggccaactta cttctgacaa cgatcggagg accgaaggag ctaaccgctt   2820
ttttgcacaa catgggggat catgtaactc gccttgatcg ttgggaaccg gagctgaatg   2880
aagccatacc aaacgacgag cgtgacacca cgatgcctgt agcaatggca acaacgttgc   2940
gcaaactatt aactggcgaa ctacttactc tagcttcccg gcaacaatta atagactgga   3000
tggaggcgga taaagttgca ggaccacttc tgcgctcggc ccttccggct ggctggttta   3060
ttgctgataa atctggagcc ggtgagcgtg ggtctcgcgg tatcattgca gcactggggc   3120
cagatggtaa gccctcccgt atcgtagtta tctacacgac ggggagtcag gcaactatgg   3180
atgaacgaaa tagacagatc gctgagatag gtgcctcact gattaagcat tggtaactgt   3240
cagaccaagt ttactcatat atactttaga ttgatttaaa acttcatttt taatttaaaa   3300
ggatctaggt gaagatcctt tttgataatc tcatgaccaa aatcccttaa cgtgagtttt   3360
cgttccactg agcgtcagac cccgtagaaa agatcaaagg atcttcttga gatccttttt   3420
ttctgcgcgt aatctgctgc ttgcaaacaa aaaaaccacc gctaccagcg gtggtttgtt   3480
tgccggatca agagctacca actctttttc cgaaggtaac tggcttcagc agagcgcaga   3540
taccaaatac tgtccttcta gtgtagccgt agttaggcca ccacttcaag aactctgtag   3600
caccgcctac atacctcgct ctgctaatcc tgttaccagt ggctgctgcc agtggcgata   3660
agtcgtgtct taccgggttg gactcaagac gatagttacc ggataaggcg cagcggtcgg   3720
gctgaacggg gggttcgtgc acacagccca gcttggagcg aacgacctac accgaactga   3780
gatacctaca gcgtgagcat tgagaaagcg ccacgcttcc cgaagggaga aaggcggaca   3840
ggtatccggt aagcggcagg gtcggaacag gagagcgcac gagggagctt ccagggggaa   3900
acgcctggta tctttatagt cctgtcgggt ttcgccacct ctgacttgag cgtcgatttt   3960
tgtgatgctc gtcagggggg cggagcctat ggaaaaacgc cagcaacgcg gcctttttac   4020
ggttcctggc cttttgctgg ccttttgctc acatgttctt tcctgcgtta tcccctgatt   4080
ctgtggataa ccgtattacc gcctttgagt gagctgatac cgctcgccgc agccgaacga   4140
ccgagcgcag cgagtcagtg agcgaggaag cggaagagcg cccaatacgc aaaccgcctc   4200
tccccgcgcg ttggccgatt cattaatgca gctggcacga caggtttccc gactggaaag   4260
cgggcagtga gcgcaacgca attaatgtga gttagctcac tcattaggca ccccaggctt   4320
tacactttat gcttccggct cgtatgttgt gtggaattgt gagcggataa caatttcaca   4380
caggaaacag ctatgaccat gattacgaat ttcgacctgc aggcatgcaa gcttgcatgc   4440
ctgcaggtcg acgctcgcgc gacttggttt gccattcttt agcgcgcgtc gcgtcacaca   4500
gcttggccac aatgtggttt ttgtcaaacg aagattctat gacgtgttta aagtttaggt   4560
cgagtaaagc gcaaatcttt tttaacccta gaaagatagt ctgcgtaaaa ttgacgcatg   4620
cattcttgaa atattgctct ctctttctaa atagcgcgaa tccgtcgctg tgcatttagg   4680
acatctcagt cgccgcttgg agctcccgtg aggcgtgctt gtcaatgcgg taagtgtcac   4740
tgattttgaa ctataacgac cgcgtgagtc aaaatgacgc atgattatct tttacgtgac   4800
ttttaagatt taactcatac gataattata ttgttatttc atgttctact tacgtgataa   4860
cttattatat atatattttc ttgttataga tatcgtgact aatatataat aaaatgggta   4920
```

-continued gttctttaga cgatgagcat atcctctctg ctcttctgca aagcgatgac gagcttgttg 4980
gtgaggattc tgacagtgaa atatcagatc acgtaagtga agatgacgtc cagagcgata 5040
cagaagaagc gtttatagat gaggtacatg aagtgcagcc aacgtcaagc ggtagtgaaa 5100
tattagacga acaaaatgtt attgaacaac caggttcttc attggcttct aacagaatct 5160
tgaccttgcc acagaggact attagaggta agaataaaca ttgttggtca acttcaaagt 5220
ccacgaggcg tagccgagtc tctgcactga acattgtcag atcggcccgg gcgccgtttt 5280
tcttgaaata ttgctctctc tttctaaata gcgcgaatcc gtcgctgtgc atttaggaca 5340
tctcagtcgc cgcttggagc tcccaaacgc gccagtggta gtacacagta ctgtgggtgt 5400
tcagtttgaa atcctcttgc ttctccattg tctcggttac ctttggtcaa atccatgggt 5460
tctattgcct atatactctt gcgattacca gtgattgcgc tattagctat tagatggatt 5520
gttggccaaa cttgtcgctt aagtggctgg gaattgtaac cgtaggcccg agtgtaatga 5580
tcccccataa aaagttttcg caatgccttt atttttgtt gcaaatctct ctttattctg 5640
cggtattctt cattattgcg gggatgggga aagtgtttat atagaagcaa cttacgattg 5700
aacccaaatg cacctgacaa gcaaggtcaa agggccagat ttttaaatat attatttagt 5760
cttaggactc tctatttgca attaaattac tttgctacct gagggttaaa tcttccccat 5820
tgataataat aattccacta tatgttcaat tgggtttcac cgcgcttagt tacatgacga 5880
gccctaatga gccgtcggtg gtctataaac tgtgccttac aaatacttgc aactcttctc 5940
gttttgaagt cagcagagtt attgctaatt gctaattgct aattgctttt aactgatttc 6000
ttcgaaattg gtgctatgtt tatggcgcta ttaacaagta tgaatgtcag gtttaaccag 6060
gggatgctta attgtgttct caacttcaaa ggcagaaatg tttactcttg accatgggtt 6120
taggtataat gttatcaagc tcctcgagtt aacgttacgt taacgttaac gttcgaggtc 6180
gactctagaa ctacccaccg tactcgtcaa ttccaagggc atcggtaaac atctgctcaa 6240
actcgaagtc ggccatatcc agagcgccgt agggggcgga gtcgtggggg gtaaatcccg 6300
gacccgggga atccccgtcc cccaacatgt ccagatcgaa atcgtctagc gcgtcggcat 6360
gcgccatcgc cacgtcctcg ccgtctaagt ggagctcgtc ccccaggctg acatcggtcg 6420 gggggccgt cgacagtctg cgcgtgtgtc ccgcggggag aaaggacagg cgcggagccg 6480
ccagccccgc ctcttcgggg gcgtcgtcgt ccgggagatc gagcaggccc tcgatggtag 6540
acccgtaatt gtttttcgta cgcgcgcggc tgtacgcggg gcccgagccc gactcgcatt 6600
tcagttgctt ttccaatccg cagataatca gctccaagcc gaacaggaat gccggctcgg 6660
ctccttgatg atcgaacagc tcgattgcct gacgcagcag tgggggcatc gaatcggttg 6720
ttggggtctc gcgctcctct tttgcgactt gatgctcttg gtcctccagc acgcagccca 6780
gggtaaagtg accgacggcg ctcagagcgt agagagcatt ttccaggctg aagccttgct 6840
ggcacaggaa cgcgagctgg ttctccagtg tctcgtattg cttttcggtc gggcgcgtgc 6900
cgagatggac tttggcaccg tctcggtggg acagcagagc gcagcggaac gacttggcgt 6960
tattgcggag gaagtcctgc caggactcgc cttccaacgg gcaaaaatgc gtgtggtggc 7020
ggtcgagcat ctcgatggcc agggcatcca gcagcgcccg cttattcttc acgtgccagt 7080
agagggtggg ctgctccacg cccagcttct gcgccaactt gcgggtcgtc agtccctcaa 7140
tgccaacttc gttcaacagc tccaacgcgg agttgatgac tttggactta tccaggcggc 7200
tgcccatggt ggtttctaaa ggtgttataa atcaaattag ttttgttttt tcttgaaaac 7260
tttgcgtttc ctttgatcaa cttaccgcca gggtaccgca gattgtttag cttgttcagc 7320

```
tgcgcttgtt tatttgctta gctttcgctt agcgacgtgt tcactttgct tgtttgaatt   7380
gaattgtcgc tccgtagacg aagcgcctct atttatactc cggcgctcgt tttcgagttt   7440
accactccct atcagtgata gagaaaagtg aaagtcgagt ttaccactcc ctatcagtga   7500
tagagaaaag tgaaagtcga gtttaccact ccctatcagt gatagagaaa agtgaaagtc   7560
gagtttacca ctccctatca gtgatagaga aaagtgaaag tcgagtttac cactccctat   7620
cagtgataga gaaaagtgaa agtcgagttt accactccct atcagtgata gagaaaagtg   7680
aaagtcgagt ttaccactcc ctatcagtga tagagaaaag tgaaagtcga aacctggcgc   7740
gcctcttaat taactcgcgt taagatacat tgatgagttt ggacaaacca caactagaat   7800
gcagtgaaaa aaatgcttta tttgtgaaat ttgtgatgct attgctttat ttgtaaccat   7860
tataagctgc aataaacaag ttaacaacaa caattgcatt cattttatgt ttcaggttca   7920
gggggaggtg tgggaggttt tttaaagcaa gtaaaacctc tacaaatgtg gtatggctga   7980
ttatgatcag ttatctagat ccggtggatc ttacgggtcc tccaccttcc gctttttctt   8040
gggtcgagat ctcaggaaca ggtggtggcg gccctcggtg cgctcgtact gctccacgat   8100
ggtgtagtcc tcgttgtggg aggtgatgtc cagcttggcg tccacgtagt agtagccggg   8160
cagctgcacg ggcttcttgg ccatgtagat ggacttgaac tccaccaggt agtggccgcc   8220
gtccttcagc ttcagggcct tgtgggtctc gcccttcagc acgccgtcgc gggggtacag   8280
gcgctcggtg gaggcctccc agcccatggt cttcttctgc atcacggggc cgtcggaggg   8340
gaagttcacg ccgatgaact tcaccttgta gatgaagcag ccgtcctgca gggaggagtc   8400
ctgggtcacg gtcgccacgc cgccgtcctc gaagttcatc acgcgctccc acttgaagcc   8460
ctcggggaag gacagcttct tgtagtcggg gatgtcggcg gggtgcttca cgtacacctt   8520
ggagccgtac tggaactggg gggacaggat gtcccaggcg aagggcaggg ggccgccctt   8580
ggtcaccttc agcttcacgg tgttgtggcc ctcgtagggg cggccctcgc cctcgccctc   8640
gatctcgaac tcgtggccgt tcacggtgcc ctccatgcgc accttgaagc gcatgaactc   8700
ggtgatgacg ttctcggagg aggccatggt ggcgaccggt ttgcgcttct tcttgggtgg   8760
ggtgggatcc ccgatctgca ttttggatta ttctgcgggt caaaatagag atgtggaaaa   8820
ttagtacgaa atcaaatgag tttcgttgaa attacaaaac tattgaaact aacttcctgg   8880
ctggggaata aaaatgggaa acttatttat cgacgccaac tttgttgaga aacccctatt   8940
aaccctctac gaatattgga acaaaggaaa gcgaagaaac aggaacaaag gtagttgaga   9000
aacctgttcc gttgctcgtc atcgttttca taatgcgagt gtgtgcatgt atatatacac   9060
agctgaaacg catgcataca cattattttg tgtgtatatg gtgacgtcac aactactaag   9120
caataagaaa ttttccagac gtggctttcg tttcaagcaa cctactctat ttcagctaaa   9180
aataagtgga tttcgttggt aaaatacttc aattaagcaa agaactaact aactaataac   9240
atgcacacaa atgctcgagt gcgttcgtga tttctcgaat tttcaaatgc gtcactgcga   9300
atttcacaat ttgccaataa atcttggcga aaatcaacac gcaagtttta tttatagatt   9360
tgtttgcgtt ttgatgccaa ttgattggga aaacaagatg cgtggctgcc aatttcttat   9420
tttgtaatta cgtagagcgt tgaataaaaa aaaaatggcc gaacaaagac cttgaaatgc   9480
agtttttctt gaaattactc aacgtcttgt tgctcttatt actaattggt aacagcgagt   9540
taaaaactta cgtttcttgt gactttcgag aatgttcttt taattgtact ttaatcacca   9600
acaattaagt ataaattttt cgctgattgc gctttacttt ctgcttgtac ttgctgctgc   9660
```

aaatgtcaat tggttttgaa ggcgaccgtt cgcgaacgct gtttatatac cttcggtgtc 9720
cgttgaaaat cactaaaaaa taccgtagtg ttcgtaacac tttagtacag agaaaaaaaa 9780
ttgtgccgaa atgtttttga tacgtacgaa taccttgtat taaaattttt tatgatttct 9840
gtgtatcact ttttttttgt gtttttcgtt taaactcacc acagtacaaa acaataaaat 9900
atttttaaga caatttcaaa ttgagacctt tctcgtactg acttgaccgg ctgaatgagg 9960
atttctacct agacgaccta cttcttacca tgacattgaa tgcaatgcca cctttgatct 10020
aaacttacaa aagtccaagg cttgttagga ttggtgttta tttagtttgc ttttgaaata 10080
gcactgtctt ctctaccggc tataattttg aaactcgcag cttgactgga aatttaaaaa 10140
gtaattctgt gtaggtaaag ggtgttttaa aagtgtgatg tgttgagcgt tgcggcaacg 10200
actgctattt atgtatatat tttcaaaact tattgttttt gaagtgtttt aaatggagct 10260
atctggcaac gctgcgcata atcttacaca agcttttctt aatccatttt taagtgaaat 10320
ttgtttttac tctttcggca aataattgtt aaatcgcttt aagtgggctt acatctggat 10380
aagtaatgaa aacctgcata ttataatatt aaaacatata atccactgtg ctttccccgt 10440
gtgtggccat atacctaaaa aagtttattt tcgcagagcc ccgcacggtc acactacggt 10500
tcggcgattt tcgattttgg acagtactga ttgcaagcgc accgaaagca aaatggagct 10560
ggagattttg aacgcgaaga acagcaagcc gtacggcaag gtgaaggtgc cctccggcgc 10620
cacgcccatc ggcgatctgc gcgccctaat tcacaagacc ctgaagcaga ccccacacgc 10680
gaatcgccag tcgcttcgtc tggaactgaa gggcaaaagc ctgaaagata cggacacatt 10740
ggaatctctg tcgctgcgtt ccggcgacaa gatcggggta ccatgc 10786

<210> SEQ ID NO 24
<211> LENGTH: 14720
<212> TYPE: DNA
<213> ORGANISM: Artificial
<220> FEATURE:
<223> OTHER INFORMATION: pLA1038

<400> SEQUENCE: 24
gggctatggc gcgccggacg cggcaagtct gcgagcttat atttacgtgg atctccggtg 60
tgtccatgat tcggcatcat atcataaacg acgaattcca ataaaaactt tgcttgttga 120
taacacctga tgttcagaga tgcccgataa aatcacagct gttctggttc acagtcacca 180
gaaataaaaa atattggaat tgagatgtac acaattaacg atatttataa atatcttccg 240
atagtctatc gtccggttaa tcaaaataaa gtgcgacgaa ttaacatatt ttcaaaatta 300
agacgctttg atagatgtat ttgtatagag atagaaatta aggttaaaat aacataaatg 360
ccaaagttta gagcactatt caataattct cttgatttca aattgaaata atacacaata 420
taacattttc taacactaca aagtcacgat attcttccac caaccgatag tatcgcacac 480
ttgccattcg cctcatcacg cacacgcccg cttcacaatt caaacgaacg gcattttatt 540
ttcacaggat cccgggagtc gtgaatgttt tacccaatat cgactttcat tgttaactga 600
ccaaaattgt aatctgttct gttagttgtc gagtgcctgt gccgcgatcg ctatgggcat 660
atgttgccaa actctaaacc aaatactcat tctgatgttt taaatgattt gccctcccat 720
atgtccttcc gagtgagaga cacaaaaaat tccaacacac tattgcaatg aaaataaatt 780
tcctttatta gccagaagtc agatgctcaa ggggcttcat gatgtcccca taatttttgg 840
cagagggaaa aagatctcag tggtatttgt gagccagggc attggccaca ccagccacca 900
ccttctgata ggcagcctgc acctgaggag tgaattcttt gccaaaatga tgagacagca 960

-continued

```
caacaaccag cacgttgccc aggagctgta ggaaagagaa gaaggcatga acatggttag   1020
cagaggggcc cggtttggac tcagagtatt ttatcctcat ctcaaacagt gtatatcatt   1080
gtaaccataa agagaaaggc aggatgatga ccagggtgta gttgtttcta ccaataagaa   1140
tatttccacg ccagccagaa tttatatgca gaaatattct accttatcat ttaattataa   1200
caattgttct ctaaaactgt gctgaagtac aatataatat accctgattg ccttgaaaaa   1260
aaagtgatta gagaaagtac ttacaatctg acaaataaac aaaagtgaat ttaaaaattc   1320
gttacaaatg caagctaaag tttaacgaaa aagttacaga aaatgaaaag aaaataagag   1380
gagacaatgg ttgtcaacag agtagaaagt gaaagaaaca aaattatcat gagggtccat   1440
ggtgatacaa gggacatctt cccattctaa acaacaccct gaaaactttg ccccctccat   1500
ataacatgaa ttttacaata gcgaaaaaga aagaacaatc aagggtcccc aaactcaccc   1560
tgaagttctc agctctagac gcgtttcact acccaccgta ctcgtcaatt ccaagggcat   1620
cggtaaacat ctgctcaaac tcgaagtcgg ccatatccag agcgccgtag gggcggagt   1680
cgtggggggt aaatcccgga cccggggaat ccccgtcccc caacatgtcc agatcgaaat   1740
cgtctagcgc gtcggcatgc gccatcgcca cgtcctcgcc gtctaagtgg agctcgtccc   1800
ccaggctgac atcggtcggg ggggccgtcg acagtctgcg cgtgtgtccc gcggggagaa   1860
aggacaggcg cggagccgcc agccccgcct cttcgggggc gtcgtcgtcc gggagatcga   1920
gcaggccctc gatggtagac ccgtaattgt ttttcgtacg cgcgcggctg tacgcggacc   1980
cactttcaca tttaagttgt ttttctaatc cgcatatgat caattcaagg ccgaataaga   2040
aggctggctc tgcaccttgg tgatcaaata attcgatagc ttgtcgtaat aatggcggca   2100
tactatcagt agtaggtgtt tccctttctt ctttagcgac ttgatgctct tgatcttcca   2160
atacgcaacc taaagtaaaa tgccccacag cgctgagtgc atataatgca ttctctagtg   2220
aaaaaccttg ttggcataaa aaggctaatt gattttcgag agtttcatac tgtttttctg   2280
taggccgtgt acctaaatgt acttttgctc catcgcgatg acttagtaaa gcacatctaa   2340
aacttttagc gttattacgt aaaaaatctt gccagctttc cccttctaaa gggcaaaagt   2400
gagtatggtg cctatctaac atctcaatgg ctaaggcgtc gagcaaagcc cgcttatttt   2460
ttacatgcca atacaatgta ggctgctcta cacctagctt ctgggcgagt ttacgggttg   2520
ttaaaccttc gattccgacc tcattaagca gctctaatgc gctgttaatc actttacttt   2580
tatctaatct caattccatg gtggcaacct gcaaggcgaa tgaataaaca agattgtggc   2640
gaacagtgta atgcgaagaa cccacctctg ctccaattcc caattcccta ttcagctcga   2700
gcggggatcc ccgggtaccg agctcgaatt cggggccgcg gaggctggat cggtcccggt   2760
gtcttctatg gaggtcaaaa cagcgtggat ggcgtctcca ggcgatctga cggttcacta   2820
aacgagctct gcttatatag gcctcccacc gtacacgcct acctcgaccc gggtaccgag   2880
ctcgactttc acttttctct atcactgata gggagtggta aactcgactt tcacttttct   2940
ctatcactga tagggagtgg taaactcgac tttcactttt ctctatcact gatagggagt   3000
ggtaaactcg actttcactt ttctctatca ctgataggga gtggtaaact cgactttcac   3060
ttttctctat cactgatagg gagtggtaaa ctcgactttc acttttctct atcactgata   3120
gggagtggta aactcgactt tcacttttct ctatcactga tagggagtgg taaactcgaa   3180
atgtcgacta tgcggaccga gcgccggagt ataaatagag gcgcttcgtc tacggagcga   3240
caattcaatt caaacaagca aagtgaacac gtcgctaagc gaaagctaag caaataaaca   3300
```

-continued

```
agcgcagctg aacaagctaa acaatctgcg ctagccacca tggttgttat taaacgtaga   3360
tttggtaatt ttaaaagcat atttttttct ttgaaattca taagttatca attatcgatg   3420
gaaatgtatt ctatggagaa cgttttaccc gatgaatggg tgcaaaaatt attttacctt   3480
caaatctaca atcaacacac gctaactttt gtgacttgat caactctcac ctggaaaagc   3540
aaccaactac aatcaacatt ctatgggata atcgacaagt gagtaaaatt atagccggac   3600
ctcttagtac agtgtattta aaaggggaat aatattctat caataggaat aaaaataagg   3660
tcagcagcca tgacttttcc atcattttga atatacctta tttgtttcgg gattaattgg   3720
gggtcggaaa tcctcttgaa ttcagaaacg ggaaccggag gaaggtgccg gtctttcaga   3780
aagctgtgaa aaataccaac atttctgctg ccaagagctc aataagaagt ttcaaaaatt   3840
gtcttggatg ttgcagctgt ggctgctaag taataagaca tctattagta tctagatttg   3900
ttagaccatt taacatagtg ttttaaacga tggggttaat agatgagggt taagaagcta   3960
gttatattac tgttgctgta acgccttcaa ttgtcggtta cagagcaaac attattgaat   4020
gttaatgtaa agagtttatt tgttttctag taaacatata gcgattggtt agtaatcact   4080
aatagaaatt tttcataagt atcaaaaaag taaacctctt tttcagtcta tgtaataagt   4140
aaaccaagga aagggaaaat atctacaatc aacaagccat tgttgcagca acaaagcaac   4200
tgaaactaca atcaacattc aataaacttg ggtaatttgg aatttaattc tctgggacac   4260
ctgtggatta caacaatcaa ctcgaaactt attatacaat gtaaataaaa attgatatgc   4320
atacatgaag atcaagtgaa attccattta gaatcaattt ttttcgaata ttaagtttct   4380
tgctttaatt tatctgaaag taaatagaca ttccaaattc aagttaacaa attaataatg   4440
aattgactag tgatttttaa gagaaaaaga taagatttaa aaaaggaaag cctttcttga   4500
taaattttttg aaccacttta tgccgtttca atcataaaaa cttttaagaa cacatgactg   4560
gtaaaattaa tttaaaacaa atttaaattt tcaacgtaac attcaacaaa aatggtgaaa   4620
actatcacgg aaattgttaa tattaatatg tcccaaaaat agcctttgta tgtatatgat   4680
actaatccat acatctatgg tatctatagg tgaaggctca aagcctctgg gcgctctcct   4740
gggcctgccc gaaagccaaa cggagcttga taatcttaca gaatacaaca cggcccacaa   4800
tcggcgcatc tcaatgctgg gcatcgatga tgataccaat atgcgaaagc aaaacgcctt   4860
gaaacaggga cggcgcactc gaaatgtcac atttaacgat gaggagattg tcatcaatcc   4920
tgaggatgtg gatcctaatg tgggacgctt caggaacttg gtacaaacca ctgtggtgcc   4980
cgccaagagg gctcgctgcg acgtcaacca ttagtgataa cgcgtctaga gctgagaact   5040
tcagggtgag tttggggacc cttgattgtt ctttcttttt cgctattgta aaattcatgt   5100
tatatggagg gggcaaagtt ttcagggtgt tgtttagaat gggaagatgt cccttgtatc   5160
accggtgatc ataatcagcc ataccacatt tgtagaggtt ttacttgctt taaaaaacct   5220
cccacacctc cccctgaacc tgaaacataa aatgaatgca attgttgttg ttaacttgtt   5280
tattgcagct tataatggtt acaaataaag caatagcatc acaaatttca caaataaagc   5340
atttttttca ctgcattcta gttgtggttt gtccaaactc atcaatgtat cttaacgcga   5400
gtttaaacgc gtccgcatac gtccgctcac gttaagttcc gcagagagaa gttgttgaaa   5460
acataaacag aatcacttgt tgcactcttt gagaaaactg gggctattgc ggaaaaaacc   5520
aactaaaaat attgcaggtt aggggtacta cgctcgattg gcgtacggcc accacttttg   5580
cgacttcact gttaaccgct accttcatag agacttttac ccgataaatg ttatgtagtt   5640
tgactttctc tgttaatcac aagaaaaaat attgtggaaa ttaaaattat ctcaaactca   5700
```

ataaggaaat aataatatat acacctatgt tttatagaag tcaacagtaa ataagttatt 5760
tggaaaacca ttgtagccgt ttaaataaat ctccttgagt gtgttttaaa taacggtcat 5820
taagtatatt acttggccct ctgaatttct tgaattacac catttttga aataaatcaa 5880
tccaaaagac tactttttgg tggcaaatga actgcataaa aagtaacaaa agaaatatgt 5940
ttttgaaata acagtatagc tgaagtgtat taaaaaatac cgtcatatga gcgacccgct 6000
gttaccgctt cgctgcgaat gacaaaacgg gctgagcaag aaaatggcgt agaaggcgac 6060
gaaaattcgt ttcactcgtg aagaaaacct cgataactga ggaatacagc tgggatttaa 6120
agagcatatt cgaactacaa gcagagatgt ttcctggtgg aaacggaaac gccgatttgg 6180
gctacaacaa gcatgcccac gtccatggac ttggacaaca tggccatggg cacaaccata 6240
atcacaatca gttcctgcgc agcccccacc accccccaca cattttcac tgccctccgg 6300
gggcggtcag ggcatggtga cgcccatggt agccgccggc ctgccgctcg ccatgcaggg 6360
tggcgttggc atcgattggc gcagctcgcc cagcaatgga ttaattaact cgcgttaaga 6420
tacattgatg agtttggaca aaccacaact agaatgcagt gaaaaaaatg ctttatttgt 6480
gaaatttgtg atgctattgc tttatttgta accattataa gctgcaataa acaagttaac 6540
aacaacaatt gcattcattt tatgtttcag gttcaggggg aggtgtggga ggttttttaa 6600
agcaagtaaa acctctacaa atgtggtatg gctgattatg atcagttatc tagatccggt 6660
ggatcttacg ggtcctccac cttccgcttt ttcttgggtc gagatctcag gaacaggtgg 6720
tggcggccct cggtgcgctc gtactgctcc acgatggtgt agtcctcgtt gtgggaggtg 6780
atgtccagct tggcgtccac gtagtagtag ccgggcagct gcacgggctt cttggccatg 6840
tagatggact tgaactccac caggtagtgg ccgccgtcct tcagcttcag ggccttgtgg 6900
gtctcgccct tcagcacgcc gtcgcggggg tacaggcgct cggtggaggc ctcccagccc 6960
atggtcttct tctgcatcac ggggccgtcg gaggggaagt tcacgccgat gaacttcacc 7020
ttgtagatga agcagccgtc ctgcagggag gagtcctggg tcacggtcgc cacgccgccg 7080
tcctcgaagt tcatcacgcg ctcccacttg aagccctcgg ggaaggacag cttcttgtag 7140
tcggggatgt cggcggggtg cttcacgtac accttggagc cgtactggaa ctggggggac 7200
aggatgtccc aggcgaaggg cagggggccg cccttggtca ccttcagctt cacggtgttg 7260
tggccctcgt aggggcggcc ctcgccctcg ccctcgatct cgaactcgtg gccgttcacg 7320
gtgccctcca tgcgcacctt gaagcgcatg aactcggtga tgacgttctc ggaggaggcc 7380
atggtggcga ccggtttgcg cttcttcttg ggtggggtgg gatccccgat ctgcattttg 7440
gattattctg cgggtcaaaa tagagatgtg gaaaattagt acgaaatcaa atgagtttcg 7500
ttgaaattac aaaactattg aaactaactt cctggctggg gaataaaaat gggaaactta 7560
tttatcgacg ccaactttgt tgagaaaccc ctattaaccc tctacgaata ttggaacaaa 7620
ggaaagcgaa gaaacaggaa caaaggtagt tgagaaacct gttccgttgc tcgtcatcgt 7680
tttcataatg cgagtgtgtg catgtatata tacacagctg aaacgcatgc atacacatta 7740
ttttgtgtgt atatggtgac gtcacaacta ctaagcaata agaaattttc cagacgtggc 7800
tttcgtttca agcaacctac tctatttcag ctaaaaataa gtggatttcg ttggtaaaat 7860
acttcaatta agcaaagaac taactaacta ataacatgca cacaaatgct cgagtgcgtt 7920
cgtgatttct cgaattttca aatgcgtcac tgcgaatttc acaatttgcc aataaatctt 7980
ggcgaaaatc aacacgcaag ttttatttat agatttgttt gcgttttgat gccaattgat 8040

-continued

```
tgggaaaaca agatgcgtgg ctgccaattt cttattttgt aattacgtag agcgttgaat   8100
aaaaaaaaaa tggccgaaca aagaccttga aatgcagttt ttcttgaaat tactcaacgt   8160
cttgttgctc ttattactaa ttggtaacag cgagttaaaa acttacgttt cttgtgactt   8220
tcgagaatgt tcttttaatt gtactttaat caccaacaat taagtataaa tttttcgctg   8280
attgcgcttt actttctgct tgtacttgct gctgcaaatg tcaattggtt ttgaaggcga   8340
ccgttcgcga acgctgttta tataccttcg gtgtccgttg aaaatcacta aaaaataccg   8400
tagtgttcgt aacactttag tacagagaaa aaaaattgtg ccgaaatgtt tttgatacgt   8460
acgaatacct tgtattaaaa ttttttatga tttctgtgta tcactttttt tttgtgtttt   8520
tcgtttaaac tcaccacagt acaaaacaat aaaatatttt taagacaatt tcaaattgag   8580
acctttctcg tactgacttg accggctgaa tgaggatttc tacctagacg acctacttct   8640
taccatgaca ttgaatgcaa tgccaccttt gatctaaact tacaaaagtc caaggcttgt   8700
taggattggt gtttatttag tttgcttttg aaatagcact gtcttctcta ccggctataa   8760
ttttgaaact cgcagcttga ctggaaattt aaaaagtaat tctgtgtagg taaagggtgt   8820
tttaaaagtg tgatgtgttg agcgttgcgg caacgactgc tatttatgta tatattttca   8880
aaacttattg tttttgaagt gttttaaatg gagctatctg gcaacgctgc gcataatctt   8940
acacaagctt ttcttaatcc atttttaagt gaaatttgtt tttactcttt cggcaaataa   9000
ttgttaaatc gctttaagtg ggcttacatc tggataagta atgaaaacct gcatattata   9060
atattaaaac atataatcca ctgtgctttc cccgtgtgtg gccatatacc taaaaaagtt   9120
tattttcgca gagccccgca cggtcacact acggttcggc gattttcgat tttggacagt   9180
actgattgca agcgcaccga aagcaaaatg gagctggaga ttttgaacgc gaagaacagc   9240
aagccgtacg gcaaggtgaa ggtgccctcc ggcgccacgc ccatcggcga tctgcgcgcc   9300
ctaattcaca agaccctgaa gcagacccca cacgcgaatc gccagtcgct tcgtctggaa   9360
ctgaagggca aaagcctgaa agatacggac acattggaat ctctgtcgct gcgttccggc   9420
gacaagatcg gggtaccatg cggccgctca tttaaatctg gccggcctgg ccgatctgac   9480
aatgttcagt gcagagactc ggctacgcct cgtggacttt gaagttgacc aacaatgttt   9540
attcttacct ctaatagtcc tctgtggcaa ggtcaagatt ctgttagaag ccaatgaaga   9600
acctggttgt tcaataacat tttgttcgtc taatatttca ctaccgcttg acgttggctg   9660
cacttcatgt acctcatcta taaacgcttc ttctgtatcg ctctggacgt catcttcact   9720
tacgtgatct gatatttcac tgtcagaatc ctcaccaaca agctcgtcat cgctttgcag   9780
aagagcagag aggatatgct catcgtctaa agaactaccc attttattat atattagtca   9840
cgatatctat aacaagaaaa tatatatata ataagttatc acgtaagtag aacatgaaat   9900
aacaatataa ttatcgtatg agttaaatct taaaagtcac gtaaaagata atcatgcgtc   9960
attttgactc acgcggtcgt tatagttcaa aatcagtgac acttaccgca ttgacaagca  10020
cgcctcacgg gagctccaag cggcgactga gatgtcctaa atgcacagcg acggattcgc  10080
gctatttaga aagagagagc aatatttcaa gaatgcatgc gtcaatttta cgcagactat  10140
ctttctaggg ttaaaaaaga tttgcgcttt actcgaccta aactttaaac acgtcataga  10200
atcttcgttt gacaaaaacc acattgtggc caagctgtgt gacgcgacgc gcgctaaaga  10260
atggcaaacc aagtcgcgcg agcgtcgacc tgcaggcatg caagcttgca tgcctgcagg  10320
tcgaaattcg taatcatggt catagctgtt tcctgtgtga aattgttatc cgctcacaat  10380
tccacacaac atacgagccg gaagcataaa gtgtaaagcc tggggtgcct aatgagtgag  10440
```

-continued

```
ctaactcaca ttaattgcgt tgcgctcact gcccgctttc cagtcgggaa acctgtcgtg  10500
ccagctgcat taatgaatcg gccaacgcgc ggggagaggc ggtttgcgta ttgggcgctc  10560
ttccgcttcc tcgctcactg actcgctgcg ctcggtcgtt cggctgcggc gagcggtatc  10620
agctcactca aaggcggtaa tacggttatc cacagaatca ggggataacg caggaaagaa  10680
catgtgagca aaaggccagc aaaaggccag gaaccgtaaa aaggccgcgt tgctggcgtt  10740
tttccatagg ctccgccccc ctgacgagca tcacaaaaat cgacgctcaa gtcagaggtg  10800
gcgaaacccg acaggactat aaagatacca ggcgtttccc cctggaagct ccctcgtgcg  10860
ctctcctgtt ccgaccctgc cgcttaccgg atacctgtcc gcctttctcc cttcgggaag  10920
cgtggcgctt tctcaatgct cacgctgtag gtatctcagt tcggtgtagg tcgttcgctc  10980
caagctgggc tgtgtgcacg aaccccccgt tcagcccgac cgctgcgcct tatccggtaa  11040
ctatcgtctt gagtccaacc cggtaagaca cgacttatcg ccactggcag cagccactgg  11100
taacaggatt agcagagcga ggtatgtagg cggtgctaca gagttcttga agtggtggcc  11160
taactacggc tacactagaa ggacagtatt tggtatctgc gctctgctga agccagttac  11220
cttcggaaaa agagttggta gctcttgatc cggcaaacaa accaccgctg gtagcggtgg  11280
tttttttgtt tgcaagcagc agattacgcg cagaaaaaaa ggatctcaag aagatccttt  11340
gatcttttct acggggtctg acgctcagtg gaacgaaaac tcacgttaag ggattttggt  11400
catgagatta tcaaaaagga tcttcaccta gatcctttta aattaaaaat gaagttttaa  11460
atcaatctaa agtatatatg agtaaacttg gtctgacagt taccaatgct taatcagtga  11520
ggcacctatc tcagcgatct gtctatttcg ttcatccata gttgcctgac tccccgtcgt  11580
gtagataact acgatacggg agggcttacc atctggcccc agtgctgcaa tgataccgcg  11640
agacccacgc tcaccggctc cagatttatc agcaataaac cagccagccg gaagggccga  11700
gcgcagaagt ggtcctgcaa ctttatccgc ctccatccag tctattaatt gttgccggga  11760
agctagagta agtagttcgc cagttaatag tttgcgcaac gttgttgcca ttgctacagg  11820
catcgtggtg tcacgctcgt cgtttggtat ggcttcattc agctccggtt cccaacgatc  11880
aaggcgagtt acatgatccc ccatgttgtg caaaaaagcg gttagctcct tcggtcctcc  11940
gatcgttgtc agaagtaagt tggccgcagt gttatcactc atggttatgg cagcactgca  12000
taattctctt actgtcatgc catccgtaag atgcttttct gtgactggtg agtactcaac  12060
caagtcattc tgagaatagt gtatgcggcg accgagttgc tcttgcccgg cgtcaatacg  12120
ggataatacc gcgccacata gcagaacttt aaaagtgctc atcattggaa aacgttcttc  12180
ggggcgaaaa ctctcaagga tcttaccgct gttgagatcc agttcgatgt aacccactcg  12240
tgcacccaac tgatcttcag catcttttac tttcaccagc gtttctgggt gagcaaaaac  12300
aggaaggcaa aatgccgcaa aaaagggaat aagggcgaca cggaaatgtt gaatactcat  12360
actcttcctt tttcaatatt attgaagcat ttatcagggt tattgtctca tgagcggata  12420
catatttgaa tgtatttaga aaaataaaca aataggggtt ccgcgcacat ttccccgaaa  12480
agtgccacct gacgtctaag aaaccattat tatcatgaca ttaacctata aaaataggcg  12540
tatcacgagg ccctttcgtc tcgcgcgttt cggtgatgac ggtgaaaacc tctgacacat  12600
gcagctcccg gagacggtca cagcttgtct gtaagcggat gccgggagca gacaagcccg  12660
tcagggcgcg tcagcgggtg ttggcgggtg tcggggctgg cttaactatg cggcatcaga  12720
gcagattgta ctgagagtgc accatatatg cggtgtgaaa taccgcacag atgcgtaagg  12780
```

-continued

```
agaaaatacc gcatcaggcg ccattcgcca ttcaggctgc gcaactgttg ggaagggcga  12840
tcggtgcggg cctcttcgct attacgccag ctggcgaaag ggggatgtgc tgcaaggcga  12900
ttaagttggg taacgccagg gttttcccag tcacgacgtt gtaaaacgac ggccagtgcc  12960
aagctttgtt taaaatataa caaaattgtg atcccacaaa atgaagtggg gcaaaatcaa  13020
ataattaata gtgtccgtaa acttgttggt cttcaacttt ttgaggaaca cgttggacgg  13080
caaatccgtg actataacac aagttgattt aataatttta gccaacacgt cgggctgcgt  13140
gtttttgcc gacgcgtctg tgtacacgtt gattaactgg tcgattaaac tgttgaaata  13200
atttaatttt tggttcttct ttaaatctgt gatgaaattt tttaaaataa ctttaaattc  13260
ttcattggta aaaaatgcca cgttttgcaa cttgtgaggg tctaatatga ggtcaaactc  13320
agtaggagtt ttatccaaaa aagaaaacat gattacgtct gtacacgaac gcgtattaac  13380
gcagagtgca aagtataaga gggttaaaaa atatatttta cgcaccatat acgcatcggg  13440
ttgatatcgt taatatggat caatttgaac agttgattaa cgtgtctctg ctcaagtctt  13500
tgatcaaaac gcaaatcgac gaaaatgtgt cggacaatat caagtcgatg agcgaaaaac  13560
taaaaaggct agaatacgac aatctcacag acagcgttga gatatacggt attcacgaca  13620
gcaggctgaa taataaaaaa attagaaact attatttaac cctagaaaga taatcatatt  13680
gtgacgtacg ttaaagataa tcatgcgtaa aattgacgca tgtgttttat cggtctgtat  13740
atcgaggttt atttattaat ttgaatagat attaagtttt attatattta cacttacata  13800
ctaataataa attcaacaaa caatttattt atgtttattt atttattaaa aaaaaacaaa  13860
aactcaaaat ttcttctata aagtaacaaa acttttaaac attctctctt ttacaaaaat  13920
aaacttattt tgtactttaa aaacagtcat gttgtattat aaaataagta attagcttaa  13980
cttatacata atagaaacaa attatactta ttagtcagtc agaaacaact ttggcacata  14040
tcaatattat gctctcgaca aataactttt ttgcattttt tgcacgatgc atttgccttt  14100
cgccttattt tagaggggca gtaagtacag taagtacgtt ttttcattac tggctcttca  14160
gtactgtcat ctgatgtacc aggcacttca tttggcaaaa tattagagat attatcgcgc  14220
aaatatctct tcaaagtagg agcttctaaa cgcttacgca taaacgatga cgtcaggctc  14280
atgtaaaggt ttctcataaa ttttttgcga ctttggacct tttctccctt gctactgaca  14340
ttatggctgt atataataaa agaatttatg caggcaatgt ttatcattcc gtacaataat  14400
gccataggcc acctattcgt cttcctactg caggtcatca cagaacacat ttggtctagc  14460
gtgtccactc cgcctttagt ttgattataa tacataacca tttgcggttt accggtactt  14520
tcgttgatag aagcatcctc atcacaagat gataataagt ataccatctt agctggcttc  14580
ggtttatatg agacgagagt aaggggtccg tcaaaacaaa acatcgatgt tcccactggc  14640
ctggagcgac tgtttttcag tacttccggt atctcgcgtt tgtttgatcg cacggttccc  14700
acaatggttg cggccagccc                                              14720
```

<210> SEQ ID NO 25
<211> LENGTH: 23
<212> TYPE: DNA
<213> ORGANISM: Artificial
<220> FEATURE:
<223> OTHER INFORMATION: PCR Primer

<400> SEQUENCE: 25

```
catcgatgcc cagcattgag atg                                          23
```

<210> SEQ ID NO 26
<211> LENGTH: 34
<212> TYPE: DNA
<213> ORGANISM: Artificial
<220> FEATURE:
<223> OTHER INFORMATION: PCR Primer

<400> SEQUENCE: 26
caagcaaagt gaacacgtcg ctaagcgaaa gcta 34

<210> SEQ ID NO 27
<211> LENGTH: 28
<212> TYPE: DNA
<213> ORGANISM: Artificial
<220> FEATURE:
<223> OTHER INFORMATION: PCR Primer

<400> SEQUENCE: 27
gccatccacg ctgttttgac ctccatag 28

<210> SEQ ID NO 28
<211> LENGTH: 27
<212> TYPE: DNA
<213> ORGANISM: Artificial
<220> FEATURE:
<223> OTHER INFORMATION: PCR Primer

<400> SEQUENCE: 28
gccaatacaa tgtaggctgc tctacac 27

<210> SEQ ID NO 29
<211> LENGTH: 1005
<212> TYPE: DNA
<213> ORGANISM: Artificial
<220> FEATURE:
<223> OTHER INFORMATION: coding region of tTA from pUHD15-1

<400> SEQUENCE: 29
atgtctagat tagataaaag taaagtgatt aacagcgcat tagagctgct taatgaggtc 60
ggaatcgaag gtttaacaac ccgtaaactc gcccagaagc taggtgtaga gcagcctaca 120
ttgtattggc atgtaaaaaa taagcgggct ttgctcgacg ccttagccat tgagatgtta 180
gataggcacc atactcactt ttgccctttta gaaggggaaa gctggcaaga tttttacgt 240 aataacgcta aaagttttag atgtgcttta ctaagtcatc gcgatggagc aaaagtacat 300
ttaggtacac ggcctacaga aaaacagtat gaaactctcg aaaatcaatt agcctttta 360 tgccaacaag gtttttcact agagaatgca ttatatgcac tcagcgctgt ggggcatttt 420
actttaggtt gcgtattgga agatcaagag catcaagtcg ctaaagaaga aagggaaaca 480
cctactactg atagtatgcc gccattatta cgacaagcta tcgaattatt tgatcaccaa 540
ggtgcagagc cagccttctt attcggcctt gaattgatca tatgcggatt agaaaaacaa 600
cttaaatgtg aaagtgggtc cgcgtacagc cgcgcgcgta cgaaaaacaa ttacgggtct 660
accatcgagg gcctgctcga tctcccggac gacgacgccc ccgaagaggc ggggctggcg 720
gctccgcgcc tgtcctttct ccccgcggga cacacgcgca gactgtcgac ggcccccccg 780
accgatgtca gcctggggga cgagctccac ttagacggcg aggacgtggc gatggcgcat 840
gccgacgcgc tagacgattt cgatctggac atgttggggg acggggattc cccgggtccg 900
ggatttaccc cccacgactc cgccccctac ggcgctctgg atatggccga cttcgagttt 960
gagcagatgt ttaccgatgc ccttggaatt gacgagtacg gtggg 1005

<210> SEQ ID NO 30
<211> LENGTH: 336
<212> TYPE: PRT
<213> ORGANISM: Artificial
<220> FEATURE:
<223> OTHER INFORMATION: tTA

<400> SEQUENCE: 30

```
Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Ala Tyr Ser Arg Ala Arg Thr Lys Asn Asn Tyr Gly Ser Thr Ile Glu
    210                 215                 220

Gly Leu Leu Asp Leu Pro Asp Asp Asp Ala Pro Glu Glu Ala Gly Leu
225                 230                 235                 240

Ala Ala Pro Arg Leu Ser Phe Leu Pro Ala Gly His Thr Arg Arg Leu
                245                 250                 255

Ser Thr Ala Pro Pro Thr Asp Val Ser Leu Gly Asp Glu Leu His Leu
            260                 265                 270

Asp Gly Glu Asp Val Ala Met Ala His Ala Asp Ala Leu Asp Asp Phe
        275                 280                 285

Asp Leu Asp Met Leu Gly Asp Gly Asp Ser Pro Gly Pro Gly Phe Thr
    290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335
```

<210> SEQ ID NO 31
<211> LENGTH: 1017
<212> TYPE: DNA
<213> ORGANISM: Artificial
<220> FEATURE:

<223> OTHER INFORMATION: tTAV

<400> SEQUENCE: 31

```
atgggcagcc gcctggataa gtccaaagtc atcaactccg cgttggagct gttgaacgaa      60
gttggcattg agggactgac gacccgcaag ttggcgcaga agctgggcgt ggagcagccc     120
accctctact ggcacgtgaa gaataagcgg gcgctgctgg atgccctggc catcgagatg     180
ctcgaccgcc accacacgca tttttgcccg ttggaaggcg agtcctggca ggacttcctc     240
cgcaataacg ccaagtcgtt ccgctgcgct ctgctgtccc accgagacgg tgccaaagtc     300
catctcggca cgcgcccgac cgaaaagcaa tacgagacac tggagaacca gctcgcgttc     360
ctgtgccagc aaggcttcag cctggaaaat gctctctacg ctctgagcgc cgtcggtcac     420
tttaccctgg gctgcgtgct ggaggaccaa gagcatcaag tcgcaaaaga ggagcgcgag     480
accccaacaa ccgattcgat gcccccactg ctgcgtcagg caatcgagct gttcgatcat     540
caaggagccg agccggcatt cctgttcggc ttggagctga ttatctgcgg attggaaaag     600
caactgaaat gcgagtcggg ctcgggcccc gcgtacagcc gcgcgcgtac gaaaaacaat     660
tacgggtcta ccatcgaggg cctgctcgat ctcccggacg acgacgcccc cgaagaggcg     720
gggctggcgg ctccgcgcct gtcctttctc cccgcgggac acacgcgcag actgtcgacg     780
gcccccccga ccgatgtcag cctgggggac gagctccact tagacggcga ggacgtggcg     840
atggcgcatg ccgacgcgct agacgatttc gatctggaca tgttggggga cggggattcc     900
ccgggtccgg gatttacccc ccacgactcc gccccctacg gcgctctgga tatggccgac     960
ttcgagtttg agcagatgtt taccgatgcc cttggaattg acgagtacgg tgggtag       1017
```

<210> SEQ ID NO 32
<211> LENGTH: 338
<212> TYPE: PRT
<213> ORGANISM: Artificial
<220> FEATURE:
<223> OTHER INFORMATION: tTAV

<400> SEQUENCE: 32

```
Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
```

-continued

```
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220

Ile Glu Gly Leu Leu Asp Leu Pro Asp Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly


<210> SEQ ID NO 33
<211> LENGTH: 4455
<212> TYPE: DNA
<213> ORGANISM: Artificial
<220> FEATURE:
<223> OTHER INFORMATION: pUHD15-1

<400> SEQUENCE: 33

ctcgaggagc ttggcccatt gcatacgttg tatccatatc ataatatgta catttatatt      60

ggctcatgtc caacattacc gccatgttga cattgattat tgactagtta ttaatagtaa     120

tcaattacgg ggtcattagt tcatagccca tatatggagt tccgcgttac ataacttacg     180

gtaaatggcc cgcctggctg accgcccaac gacccccgcc cattgacgtc aataatgacg     240

tatgttccca tagtaacgcc aatagggact ttccattgac gtcaatgggt ggagtattta     300

cgctaaactg cccacttggc agtacatcaa gtgtatcata tgccaagtac gccccctatt     360

gacgtcaatg acggtaaatg gcccgcctgg cattatgccc agtacatgac cttatgggac     420

tttcctactt ggcagtacat ctacgtatta gtcatcgcta ttaccatggt gatgcggttt     480

tggcagtaca tcaatgggcg tggatagcgg tttgactcac ggggatttcc aagtctccac     540

cccattgacg tcaatgggag tttgttttgg caccaaaatc aacgggactt tccaaaatgt     600

cgtaacaact ccgccccatt gacgcaaatg ggcggtaggc gtgtacggtg ggaggtctat     660

ataagcagag ctcgtttagt gaaccgtcag atcgcctgga gacgccatcc acgctgtttt     720

gacctccata gaagacaccg ggaccgatcc agcctccgcg gccccgaatt catatgtcta     780

gattagataa aagtaaagtg attaacagcg cattagagct gcttaatgag gtcggaatcg     840

aaggtttaac aacccgtaaa ctcgcccaga agctaggtgt agagcagcct acattgtatt     900

ggcatgtaaa aaataagcgg gctttgctcg acgccttagc cattgagatg ttagataggc     960

accatactca cttttgccct ttagaagggg aaagctggca agatttttta cgtaataacg    1020

ctaaaagttt tagatgtgct ttactaagtc atcgcgatgg agcaaaagta catttaggta    1080
```

-continued cacggcctac agaaaaacag tatgaaactc tcgaaaatca attagccttt ttatgccaac 1140
aaggtttttc actagagaat gcattatatg cactcagcgc tgtggggcat tttactttag 1200
gttgcgtatt ggaagatcaa gagcatcaag tcgctaaaga agaaagggaa acacctacta 1260
ctgatagtat gccgccatta ttacgacaag ctatcgaatt atttgatcac caaggtgcag 1320
agccagcctt cttattcggc cttgaattga tcatatgcgg attagaaaaa caacttaaat 1380
gtgaaagtgg gtccgcgtac agccgcgcgc gtacgaaaaa caattacggg tctaccatcg 1440
agggcctgct cgatctcccg gacgacgacg cccccgaaga ggcggggctg gcggctccgc 1500
gcctgtcctt tctccccgcg ggacacacgc gcagactgtc gacggccccc ccgaccgatg 1560
tcagcctggg ggacgagctc cacttagacg gcgaggacgt ggcgatggcg catgccgacg 1620
cgctagacga tttcgatctg gacatgttgg gggacgggga ttccccgggt ccgggattta 1680
ccccccacga ctccgccccc tacggcgctc tggatatggc cgacttcgag tttgagcaga 1740
tgtttaccga tgcccttgga attgacgagt acggtgggta gggggcgcga ggatccagac 1800
atgataagat acattgatga gtttggacaa accacaacta gaatgcagtg aaaaaaatgc 1860
tttatttgtg aaatttgtga tgctattgct ttatttgtaa ccattataag ctgcaataaa 1920
caagttaaca acaacaattg cattcatttt atgtttcagg ttcaggggga ggtgtgggag 1980
gttttttaaa gcaagtaaaa cctctacaaa tgtggtatgg ctgattatga tcctgcaagc 2040
ctcgtcgtct ggccggacca cgctatctgt gcaaggtccc cggacgcgcg ctccatgagc 2100
agagcgcccg ccgccgaggc aagactcggg cggcgccctg cccgtcccac caggtcaaca 2160
ggcggtaacc ggcctcttca tcgggaatgc gcgcgacctt cagcatcgcc ggcatgtccc 2220
ctggcggacg ggaagtatca gctcgaccaa gcttggcgag attttcagga gctaaggaag 2280
ctaaaatgga gaaaaaaatc actggatata ccaccgttga tatatcccaa tggcatcgta 2340
aagaacattt tgaggcattt cagtcagttg ctcaatgtac ctataaccag accgttcagc 2400
tgcattaatg aatcggccaa cgcgcgggga gaggcggttt gcgtattggg cgctcttccg 2460
cttcctcgct cactgactcg ctgcgctcgg tcgttcggct gcggcgagcg gtatcagctc 2520
actcaaaggc ggtaatacgg ttatccacag aatcagggga taacgcagga aagaacatgt 2580
gagcaaaagg ccagcaaaag gccaggaacc gtaaaaaggc cgcgttgctg gcgtttttcc 2640
ataggctccg cccccctgac gagcatcaca aaaatcgacg ctcaagtcag aggtggcgaa 2700
acccgacagg actataaaga taccaggcgt ttccccctgg aagctccctc gtgcgctctc 2760
ctgttccgac cctgccgctt accggatacc tgtccgcctt tctcccttcg ggaagcgtgg 2820
cgctttctca atgctcacgc tgtaggtatc tcagttcggt gtaggtcgtt cgctccaagc 2880
tgggctgtgt gcacgaaccc cccgttcagc ccgaccgctg cgccttatcc ggtaactatc 2940
gtcttgagtc caacccggta agacacgact tatcgccact ggcagcagcc actggtaaca 3000
ggattagcag agcgaggtat gtaggcggtg ctacagagtt cttgaagtgg tggcctaact 3060
acggctacac tagaaggaca gtatttggta tctgcgctct gctgaagcca gttaccttcg 3120
gaaaaagagt tggtagctct tgatccggca aacaaaccac cgctggtagc ggtggttttt 3180
ttgtttgcaa gcagcagatt acgcgcagaa aaaaaggatc tcaagaagat cctttgatct 3240
tttctacggg gtctgacgct cagtggaacg aaaactcacg ttaagggatt ttggtcatga 3300
gattatcaaa aaggatcttc acctagatcc ttttaaatta aaaatgaagt tttaaatcaa 3360
tctaaagtat atatgagtaa acttggtctg acagttacca atgcttaatc agtgaggcac 3420

-continued

```
ctatctcagc gatctgtcta tttcgttcat ccatagttgc ctgactcccc gtcgtgtaga   3480

taactacgat acgggagggc ttaccatctg gccccagtgc tgcaatgata ccgcgagacc   3540

cacgctcacc ggctccagat ttatcagcaa taaaccagcc agccggaagg gccgagcgca   3600

gaagtggtcc tgcaacttta tccgcctcca tccagtctat taattgttgc cgggaagcta   3660

gagtaagtag ttcgccagtt aatagtttgc gcaacgttgt tgccattgct acaggcatcg   3720

tggtgtcacg ctcgtcgttt ggtatggctt cattcagctc cggttcccaa cgatcaaggc   3780

gagttacatg atcccccatg ttgtgcaaaa aagcggttag ctccttcggt cctccgatcg   3840

ttgtcagaag taagttggcc gcagtgttat cactcatggt tatggcagca ctgcataatt   3900

ctcttactgt catgccatcc gtaagatgct tttctgtgac tggtgagtac tcaaccaagt   3960

cattctgaga atagtgtatg cggcgaccga gttgctcttg cccggcgtca atacgggata   4020

ataccgcgcc acatagcaga actttaaaag tgctcatcat tggaaaacgt tcttcggggc   4080

gaaaactctc aaggatctta ccgctgttga gatccagttc gatgtaaccc actcgtgcac   4140

ccaactgatc ttcagcatct tttactttca ccagcgtttc tgggtgagca aaaacaggaa   4200

ggcaaaatgc cgcaaaaaag ggaataaggg cgacacggaa atgttgaata ctcatactct   4260

tcctttttca atattattga agcatttatc agggttattg tctcatgagc ggatacatat   4320

ttgaatgtat ttagaaaaat aaacaaatag gggttccgcg cacatttccc cgaaaagtgc   4380

cacctgacgt ctaagaaacc attattatca tgacattaac ctataaaaat aggcgtatca   4440

cgaggccctt tcgtc                                                    4455
```

EXPRESSION SYSTEM FOR INSECT PEST CONTROL

CROSS REFERENCE TO RELATED APPLICATIONS

This application is a National Stage of International Application No. PCT/GB2004/003263, filed Jul. 28, 2004, which claims priority to GB 0317656.7, filed Jul. 28, 2003.

The present invention relates to insect expression systems comprising a promoter.

The genetic manipulation of insect species other than *Drosophila melanogaster*, by recombinant DNA methods, is in its infancy (Alphey, 2002; Alphey and Andreasen, 2002; Alphey et al, 2002; Benedict and Robinson, 2003; Berghammer et al., 1999; Catteruccia et al, 2000; Coates et al, 1998; Handler, 2002; Horn et al, 2002; Jasinskiene et al, 1998; Lobo et al., 2002; Lozovsky et al., 2002; McCombs and Saul, 1995; Moreira et al., 2004; Peloquin et al, 2000; Perera et al., 2002; Scott et al., 2004), and very few transgenic lines of non-*Drosophila* insects have been made, using heterologous promoters.

Insect transformation is a low-efficiency system requiring the identification of rare transformants, in a background of larger numbers of non-transformed individuals. It is, therefore, important that the transformants have an easily scored marker. The current favourites are the fluorescent proteins, such as GFP, DsRed and their mutant derivatives. These require transcriptional control elements, including a promoter, for their function. The best known of these are from the *Drosophila* Actin5C (Act5C) and ubi-p63E (Pub) genes. A silk moth homologue of Act5C, BmA3, has also been used, as well as a couple of tissue-specific promoters (3×P3, a synthetic eye-specific promoter, and Act88F, specific to the indirect flight muscles).

However, none of these promoters is entirely satisfactory. Act5C has been used to transform various mosquitoes, as well as *Drosophila*, but its expression pattern in mosquitoes is far from ubiquitous (Catteruccia et al, 2000; Pinkerton et al., 2000). Efforts to use it as part of a transformation marker in medfly (*Ceratitis capitata*) have failed, where equivalent experiments with Pub have achieved good success. Pub has similar limitations: the expression pattern seen in medfly transformants is highly variable, suggesting that the expression pattern is at least highly sensitive to position effect. In addition, none of these promoters can be regulated in the sense of being turned on and off as desired.

Fussenegger et al, (1998a; 1998b) illustrate positive feedback driving multi-cistronic transcripts, using a selection marker, in one instance. Experiments were restricted to mammalian systems. pTRIDENT is described as a tricistronic artificial mammalian operon. Expression or transient expression of cell cycle arresting genes is described for "metabolic engineering", i.e. regulating expression of desirable proteins, and it is mentioned that a transcriptional "squelching" effect by the VP16 transactivator domain may be lethal for the host cell, even at moderate expression levels (Berger et al., 1990; Damke et al, 1995; Gill and Ptashne, 1988; Gossen and Bujard, 1992; Salghetti et al., 2001). The benefits of autoregulatory mono- or poly-cistronic systems are discussed, including one-step, auto-regulated and auto-selective multicistronic mammalian expression systems which included the tTA in a multicistronic, pTRIDENT-based or quattrocistronic configuration (pQuattro-tTA; Fussenegger et al, (1998b); FIG. 2). Since the tTA gene is encoded on the multicistronic expression unit itself, little or no tTA is expressed under repressive conditions. This positive feedback regulation system showed no signs of squelching. Experiments with a monocistronic positive feedback configuration in transgenic animals also showed no detrimental effects (Shockett et al., 1995).

Very few promoters or other control elements have been characterised, and there remains a pressing need for such elements. It would be desirable to provide a universal promoter active in all or most cells of a wide range of insects, or to enable wider usage of an existing promoter. It is a further aim to regulate the activity of insect promoters, especially in a life stage—and/or sex-specific manner. It is also an aim to selectively reduce or eliminate the promoter activity in particular cells or tissues. The present invention provides such systems.

Surprisingly, it has now been found that it is possible to employ a positive feedback mechanism both to enhance the effect of an insect promoter, as well as to control its expression.

Thus, in a first aspect, the present invention provides an insect gene expression system, comprising at least one gene to be expressed and at least one promoter therefor, wherein a product of a gene to be expressed serves as a positive transcriptional control factor for the at least one promoter, and whereby the product, or the expression of the product, is controllable.

As used herein, the term "gene" refers to any DNA sequence that may transcribed or translated into a product, at least one such having activity or function in vivo. Such a gene will normally have at least a transcription promoter and a terminator operably associated therewith.

The product capable of positive transcriptional control may act in any suitable manner. In particular, the product may bind to an enhancer located in proximity to the promoter or promoters, thereby serving to enhance polymerase binding at the promoter, for example. Other mechanisms may be employed, such as repressor countering mechanisms, such as the blocking of an inhibitor of transcription or translation. Transcription inhibitors may be blocked, for example, by the use of hairpin RNA's or ribozymes to block translation of the mRNA encoding the inhibitor, for example, or the product may bind the inhibitor directly, thereby preventing inhibition of transcription or translation.

More preferably, the mechanism is a positive feedback mechanism, wherein the product, which may either be RNA or the translation product thereof, acts at a transcription enhancer site, normally by binding the site, thereby enhancing promoter activity. Enhancement of the promoter activity then serves to increase transcription of the gene for the product which, in turn, further serves to either lift inhibition or enhance promotion, thereby leading to a positive feedback loop.

Control of the product may be by any suitable means, and may be effective at any level. In particular, it is preferred that the control be effective either to block transcription of the control factor gene or to block translation of the RNA product thereof, or to prevent or inhibit action of the translation product of the gene.

For example, the gene product of tTA (tetracycline-repressible transcription activator) acts at the tetO operator sequence (Baron and Bujard, 2000; Gossen et al., 1994; Gossen and Bujard, 1992). Upstream of a promoter, in either orientation, tetO is capable of enhancing levels of transcription from a promoter in close proximity thereto, when bound by the product of the tTA gene. If the tTA gene is part of the cassette comprising the tetO operator together with the promoter, then positive feedback occurs when the tTA gene product is expressed.

Control of this system is readily achieved by exposure to tetracycline, which binds to the gene product and prevents transactivation at tetO.

The tTA system also has the advantage of providing stage-specific toxicity in a number of species. In particular, "squelching" is observed in the development phases of many insects, the precise phase of susceptible insects being species-dependent. Some insects may reach pupation before the larva dies, while others die early on. Susceptibility ranges from 100% fatality to a small reduction in survival rates. In general, though, adult insects appear to be immune to the squelching effect of tTA, so that it is possible to raise insects comprising a tTA positive feedback system in the presence of tetracycline, and then to release the adult insects into the wild. These insects are at little or no competitive disadvantage to the wild type, and will breed with the wild type insects, but larvae carrying the tTA positive feedback cassette will die before reaching maturity.

It is relatively straightforward to modify the tTA sequence to enhance compatibility with the desired insect species, and this has been demonstrated, in the accompanying Examples, with tTAV, which has an additional two amino acids to provide a protease site, but which is encoded by a sequence substantially changed from that of tTA in order to more closely follow *Drosophila* usage.

Accordingly, in a preferred aspect, the present invention provides a system as described, wherein at least one gene is tTA, or is a gene encoding a similar product to tTA effective to up-regulate the tetO promoter.

Thus, the present invention is useful in combination with a dominant lethal gene, allowing selective expression of the dominant lethal gene, or stage specific expression, as desired, of the lethal gene or the lethal phenotype. It will be appreciated that the dominant lethal gene does not need to be an integral part of the positive feedback mechanism, but may be part of a bicistronic cassette, for example. Use of the present invention in association with RIDL (Release of Insects carrying a Dominant Lethal) is particularly preferred.

Control of the feedback mechanism, in the case of tTA or an analogue thereof, is simply effected by the presence or absence of tetracycline, or by modulating tetracycline concentration, when the tTA gene product is used. In the case of another preferred positive feedback system, GAL4, this may be controlled by temperature, for example, thereby suppressing the effective gene, preferably a dominant lethal gene, until release of the insect.

Other mechanisms may also be employed, such as ribozymes or antisense or partially self-complementary RNA molecules, such as hairpin RNA, to inhibit or prevent expression of an activating peptide, or blocking agents that prevent binding of the activator to the enhancer site.

Such blocking agents may be expressed by the insect itself under selective conditions, or may be administered as part of the culture medium, for example.

Where the blocking, or controlling agents are produced by the insect, then it is preferred that their expression be selective, such as being sex specific. Administration of the blocking agent in the culture medium, for example, will enable suppression of the positive feedback cassette under all circumstances until release of the insect, after which stage- or sex-specific selection will occur, preferably in a succeeding generation, particularly preferably the following generation.

More preferably, the cassette comprising the positive feedback mechanism is associated with stage- or sex-specificity. For example, sex specific splicing is observed with the transformer and doublesex mechanisms seen in most insects, and can be employed to limit expression of the feedback system to a particular sex, either by employing sex specific splicing to delete all or part of the effector gene, or to incorporate a frameshift or stop codon, or to modulate RNA stability or mRNA translational efficiency, for example, or otherwise to affect expression so as to differentiate between the sexes. Targeting the females of pest species is particularly preferred.

Although it is possible to provide the effector gene in a separate location and even on a separate chromosome, it is generally preferable to link the effector gene with the feedback gene. This may be achieved either by placing the two genes in tandem, including the possibility of providing the two as a fusion product, or for example by providing each gene with its own promoter in opposite orientations but in juxtaposition to the enhancer site.

An effector gene is the gene whose expression it is desired to enhance. Where a positive feedback product is also effective as a stage-specific lethal, such as tTA in many species, then the effector and the feedback gene may be one and the same, and this is a preferred embodiment.

The effector gene will often be a lethal gene, and it is envisaged that the system of the present invention will most frequently be employed in the control of insect pest populations, particularly in combination with the RIDL technique or related method, as described hereinunder.

It is preferred to include a marker with the systems of the invention, such as DsRed, green fluorescent protein, and variants thereon, as transformation success rates in insects are extremely low, so that it is useful to be able to select in some way.

The promoter may be a large or complex promoter, but these often suffer the disadvantage of being poorly or patchily utilised when introduced into non-host insects. Accordingly, it is preferred to employ minimal promoters, such as the Hsp70 promoter which, while having a naturally somewhat low level of activity, can be substantially enhanced by a positive feedback scenario, such as by the use of tTA and tetO.

A promoter is a DNA sequence, generally directly upstream to the coding sequence, required for basal and/or regulated transcription of a gene. In particular, a promoter has sufficient information to allow initiation of transcription, generally having a transcription initiation start site and a binding site for the polymerase complex. A minimal promoter will generally have sufficient additional sequence to permit these two to be effective. Other sequence information, such as that which determines tissue specificity, for example, is usually lacking, and preferred minimal promoters are, normally as a direct result of this deficiency, substantially inactive in the absence of an active enhancer. Thus, a cistron, or system, the two terms preferably being generally interchangeable herein, of the invention will generally be inactive when the or each promoter is a minimal promoter, until a suitable enhancer or other regulatory element is de-repressed or activated, typically the gene product.

Thus, it will be appreciated that minimal promoters may be obtained directly from known sources of promoters, or derived from larger naturally occurring, or otherwise known, promoters. Suitable minimal promoters and how to obtain them will be readily apparent to those skilled in the art. For example, suitable minimal promoters include a minimal promoter derived from hsp70, a P minimal promoter (exemplified hereinunder as WTP-tTA), a CMV minimal promoter (exemplified hereinunder as JY2004-tTA), an Act5C-based minimal promoter, a BmA3 promoter fragment, and an Adh core promoter (Bieschke, E., Wheeler, J., and Tower, J. (1998). Doxycycline-induced transgene expression during

*Drosophila* development and aging. Mol Gen Genet 258, 571-579). Act5C responds to tTA in transgenic *Aedes*, for example, and the invention.

Not all minimal promoters will necessarily work in all species of insect, but it is readily apparent to those skilled in the art as to how to ensure that the promoter is active. For example, a plasmid, or other vector, comprising a cistron of the invention with the minimal promoter to be tested further comprises a marker, such a gene encoding a fluorescent protein, under the control of a promoter known to work in that species, the method further comprising assaying putative transgenic individuals for expression of the marker, and wherein individuals expressing the marker are then assayed for expression of the gene under the control of the minimal promoter, such as by assaying transcribed RNA. Presence of the RNA above background levels under induced or de-repressed conditions is indicative that the minimal promoter is active in the species under investigation; absence or presence at low levels only of such RNA in non-induced or repressed conditions is indicative that the minimal promoter has low intrinsic basal activity.

We have used the following marker promoters, by way of example, only, but many more are useful and apparent to those skilled in the art:

mini-white (white promoter): WTP2-tTA, JY2004-tTA

Act5C promoter: LA513 and LA517 ubi-p63E promoter: LA656 and LA1038

BmA3 promoter: LA710 hr enhancer and ie1 promoter: LA928, LA1124 and LA1188 and all of these are useful as, or in the preparation of, minimal promoters.

It will be appreciated that a cistron or system of the invention may comprise two or more cistrons. A system may further comprise non-linked elements, such as where a second gene to be expressed is remote from the positive feedback cistron.

Thus, in a preferred aspect, the present invention provides positive feedback constructs of the general form shown in accompanying FIG. 1. In this scenario, the tetracycline-repressible transcription activator (tTA) protein, when expressed, binds to the tetO operator sequence and drives expression from a nearby minimal promoter. In the configuration shown, this then drives expression of tTA, which then binds to tetO, and so on, creating a positive feedback system. This system is inhibited by tetracycline, which binds to tTA and prevents it binding tetO.

Expression is controllable, and this may be achieved by operably linking the promoter to a controllable transcription factor. As illustrated above, this may be tTA (tetracycline-repressible or tetracycline-inducible), or any other factor controllable system, such as GAL4 (which is somewhat cold-sensitive, and can be further controlled by use of GAL80 or mutants thereof), or the streptogrammin regulated expression system, for example. It will be appreciated that other binding sites for the appropriate transcription factor will depend on the transcription factor concerned, such as $UAS_{GAL4}$ (upstream activation sequence) for GAL4, for example.

Preferred systems of the present invention have high levels of induced expression, preferably available at several induced levels, with a low basal level of expression of the regulated gene but also of any other component, and preferably across a range of species. Basal levels are preferably low or substantially non-existent where expression is strongly deleterious, but acceptable levels will depend on the effect of the product. Maximum levels will not generally be an issue, as the positive feedback condition will often provide fatal levels of expression and, even where the expression product is not fatal, or associated with fatal consequences, it is likely to be expressed in far higher concentrations than most gene products.

Where a basal level of expression is desired, then a promoter sequence that does not need the presence of the enhancer may be employed, although there will then, generally, be feedback. Unless there is a cut-off level of feedback, below which the feedback product will not work, then it will be appreciated that it is preferred to keep to a minimum feedback gene expression Different constructs of the invention (described in the accompanying Examples) have varying activity, according to the components of the constructs. For example, in *Drosophila:*

WTP-tTA gives a low level of induced (non-repressed) expression

JY2004-tTA gives strong expression when not repressed, approximately equivalent to Act5C-tTA LA513 is lethal when not repressed.

The first two appear to give constitutive expression, as judged by use of a reporter gene (tRE-EGFP), this is difficult to assess for the lethal LA513, although at 10 μg/ml tet, just sufficient for good survival, LA513 in *Drosophila* drives expression of a $tetO_7$-EGFP reporter gene in both the male and female germline in adults, as well as in somatic cells. This distinguishes it from Act5C, commonly used as a "ubiquitous, constitutive" promoter, which does not, in fact, express well in these cells.

The properties of these constructs are shown in Table 1, below.

TABLE 1

| | Max expression | Minimal promoter | Intron | Optimised coding region? | 3'UTR and polyA |
|---|---|---|---|---|---|
| WTP-tTA | Low | P | PP1α96A | No | fs(1)K10 |
| JY2004-tTA | High | CMV | Rabbit β-globin | No | Rabbit β-globin |
| LA513 | V. high (lethal) | Hsp70 | Adh | Yes | fs(1)K10 |

Accordingly, it will be appreciated that the induced or non-repressed expression level can be modified in a useful and predictable way by adjusting the sequence of the positive feedback system. Toxicity and/or activity of the tTA protein can be modified independently of the transcriptional and translational control signals by several approaches, e.g. use of a nuclear localisation signal, modification of the activation domain, etc. (see Fussenegger, 2001 for more examples).

The lethality of LA513 is useful, for the reasons given above, and more particularly because:

a) It provides a compact, highly effective repressible lethal gene system;

b) As it uses only simple control elements from *Drosophila* (hsp70 minimal promoter, a small intron and a terminator from fs(1)K10), it, or its expression cassette, functions across a wide phylogenetic range;

c) It has very little, if any, deleterious effect on adults, even in the absence of tetracycline. This is a highly desirable and surprising property for field use, for example in a RIDL-based control programme, as the released adults must be competitive and long-lived for full efficacy of the programme. It will be appreciated that the effect of the system of the invention could be further modified by the incorporation of an adult-effective lethal, for example in the "positive feedback—bi-directional expression" configuration described herein; and d) By its nature, "cross-talk" between various elements is minimised. This is because: (i) the core of the construct is only a single composite element, rather than the normal two in bipartite expression systems; (ii) the principal enhancer of the autoregulatory component, the tTA binding sites, is substantially active only in the absence of tetracycline and (iii) modest expression of tTA under the influence of a nearby enhancer, whether in another part of the construct or in nearby chromatin, is unlikely to be significantly deleterious.

JY2004-tTA is also useful, in the present invention.

Without being bound by theory, the mechanism by which LA513 kills embryos and early larvae, but not adults, appears to be an inherent property of its toxicity. tTA toxicity is believed to derive from "transcriptional squelching", in which high level expression of the transcriptional activator domain (in the case of tTA this is VP16 or a fragment thereof) binds elements of the transcriptional machinery and titrates them, leading to a general effect on transcription, although it may also act to saturate the ubiquitin degradation pathway. Transcriptional squelching is the effect which is thought to lead to deleterious effects in mammalian cell lines expressing tTA at high levels; in the optimised expression context of LA513 positive feedback drives tTA expression to lethal levels. However, developing stages may be more sensitive to disruption of transcription than adults: they have to express genes in a highly coordinated fashion to allow proper development, while adults may be more tolerant of disruption.

The development of LA513 heterozygotes on media with an intermediate level of tet (3 or 10 μg/ml), just sufficient for survival, showed a significant delay, relative to their wild type siblings. Parallel experiments using higher concentrations of tetracycline, e.g. 100 μg/ml, did not show any developmental delay, thereby suggesting that sub-lethal expression of tTA can adversely affect the normal development of the insects.

It is preferred that a positive feedback system show a higher on:off ratio and switch from on to off over a narrower concentration range than a conventional system, thereby allowing the use of a wider range of effector molecules. Lower-toxicity (lower specific activity) effector molecules can be used, as they can be expressed at a high level under active conditions without leading to problems of toxicity at basal levels. Conversely, more toxic (higher specific activity) ones can be used as the necessary low basal level does not preclude high levels of expression when de-repressed or induced. Since basal level of expression is only partly determined by the level of tTA, this advantage is particularly clear in the case of lower-toxicity molecules. tTA is a preferred example of a low specific activity effector molecule that can be used as a lethal in the positive feedback context of LA513, for example. The advantage of switching from on to off over a narrow concentration range is that a modest concentration of repressor can be used without risk of residual (not fully repressed) expression leading to adverse effects and potentially selecting for resistance. Conversely, for an inducible system, modest concentrations of the activator can give full expression.

Activated or de-repressed drivers are useful for expressing effector molecules. Examples of effector molecules include functional RNA's, such as hairpin RNA's, ribozymes etc., and one or more encoded proteins. It will be appreciated that, for different applications, different levels of expression are appropriate. Since the sequence-specific transcription factors used to drive the positive feedback system can also be used to express other genes in a bipartite expression system, this may be achieved by making two separate constructs, one with the driver (normally a promoter-transcription factor construct, here the positive feedback construct), the other with the gene or molecule of interest under the control of a composite promoter (binding site+minimal promoter) responsive to the transcription factor (Bello et al, 1998; Brand et al, 1994). This is also appropriate for these positive feedback drivers. Alternatively, the two elements may be combined on the same construct. This embodiment has significant advantages for most field applications, as it very substantially reduces the risk that the two functional elements can be separated by recombination. Further, the complete expression system can be introduced with only a single transformation event, as well as meaning that insects homozygous for the system are homozygous at only one locus rather than two, which makes them easier to construct by breeding, and tends to reduce the fitness cost due to insertional mutagenesis.

It is also possible to condense such an expression system into a more compact form, such as is illustrated in accompanying FIG. 2.

This exploits the bi-directional nature of enhancers, in this case the tetO binding site in the presence of tTA. This arrangement further allows, or facilitates, the use of insulator elements to reduce the effect of enhancers or suppressors in the adjacent chromatin: in this arrangement the entire expression cassette can be flanked by insulators. This arrangement also removes the need to duplicate the transcription factor binding sites within the construct. Such duplication is preferably avoided, as it can lead to instability through homologous recombination. For similar reasons, it is generally preferred that non-identical insulators, such as scs and scs' are used, rather than using the same one twice.

It is further possible to condense the system to provide a single transcript, either bicistronic or expressing a single polypeptide, which may potentially be further processed into more than one protein, for example by use of the ubiquitin fusion technique (Varshavsky, 2000). Bach of these approaches (bi-directional expression, bicistronic expression, fusion protein with transactivator) tends to reduce the size of the construct, which in turn will tend to increase the transformation frequency and reduce the mutagenic target. Such condensation can be achieved in several ways, as shown, diagrammatically, in accompanying FIG. 3. Appropriate extensions to and variations of the arrangements shown diagrammatically will be apparent to those skilled in the art.

As an example of the utility of such a system, a general transformation marker might be constructed by using a transactivator system known to function over a wide phylogenetic range, for example those based on tetR, GAL4, lexA or AcNPV ie-1. Such a transactivator, functionally linked to a coding region for a fluorescent protein by any of the above methods (bi-directional expression, bicistronic expression, fusion protein with transactivator), would provide a genetic marker expressed in a wide range of tissues and developmental stages across a broad phylogenetic range. Such a marker would be useful not only for detecting transgenics in transformation and other lab experiments, but also for distinguishing, for example, transgenic flies from wild type flies in the field, or those caught in the field.

Another example is expression of a transposase. Integrated into the chromosomes, this would be a "jump-starter" construct, for example piggyBac transposase integrated into an insect chromosome using mariner/mos1. Such constructs are useful to remobilise piggyBac elements. A widely-applicable jump-starter should be expressed at a significant level across a wide phylogenetic range. The expression system of this invention provides this. Furthermore, such a construct (piggyBac transposase under the control of a positive feedback system of one of the above structures) would also be useful in insect transformation via transient expression (co-expression of a "helper" plasmid, the most widely-used method for insect transformation), and again would be useful and functional across a wide phylogenetic range.

It is advantageous to regulate the action of an expression system at stage-, sex- or other levels, in addition to being able to regulate the expression level by changing environmental conditions. Suitable examples are as follows:

1. Expression of a Repressor Protein.

Repressor proteins are known or can be constructed for the main expression systems, e.g. GAL80 or its mutant derivatives for the GAL4 system, tetR fused to inhibitory proteins for the tet system, etc. Another alternative is gene silencing of the transcription factor using a hairpin RNA directed against part of the expression cassette. Basal expression from the positive feedback system is rather low, therefore it can readily be suppressed by expression of such an inhibitor.

Expression of a suitable inhibitor under suitable control will tend to inhibit expression from the positive feedback expression cassette where the inhibitor is expressed. Female-specific expression, for example, can therefore be achieved by expressing an inhibitor in males.

2. Integrating Specificity into the Positive Feedback System.

Specificity can be integrated into the positive feedback system by using components that are themselves specific. For example, the hsp70 minimal promoter+SV40 intron and polyA signal combination of pUAST is known not to be expressed in the female germline of *Drosophila*, while the P minimal promoter+P intron+fs(1)K10 polyA signal of pUASp is so expressed (Rorth, 1998). Positive feedback expression systems can, therefore, be constructed which specifically do or do not express in this tissue, depending on the use of appropriate regulatory elements.

In another embodiment, sex-specificity can be integrated into the system by use of sex-specific splicing. The sex-specific splicing of doublesex and its homologues is a conserved regulatory mechanism and, therefore, available for use in this way across a wide phylogenetic range. Sex-specific splicing of transformer and its homologues is another alternative. The use of sex-specific splicing to integrate specificity into a positive feedback expression system can be achieved in several ways, as shown, diagrammatically, in accompanying FIG. 4. Appropriate extensions to and variations of the arrangements shown diagrammatically will be apparent to those skilled in the art.

In another configuration, a specific splice site can be inserted into the transactivator coding region so that two (or more) alternative proteins are produced in different conditions, e.g. in different cell types or in different sexes. This can be arranged so that a transcriptional activator is produced in one cell type but a transcriptional repressor is produced in another cell type. This arrangement has the advantage that it is relatively robust to inefficient (imperfect) splicing—production of a relatively low proportion of transcriptional activator in the inappropriate cell type, e.g. in male cells, will be less likely to produce the positive feedback amplification as these cells are also producing a larger amount of repressor. Discrimination in output (ratio of levels of transcriptional activator in the two cell types, or ratio of expression of a reporter or other RNA or protein functionally linked to the expression of the transcriptional activator) between the two cell types is thereby enhanced.

It will be readily apparent to those skilled in the art that any of these specific transactivator arrangements can readily be combined with any of the arrangements disclosed herein for expression of an additional protein or RNA, e.g. bi-directional expression, bi- or multi-cistronic expression, expression of a fusion protein, or combined with one or more separate expression cassettes dependent on, or partly dependent on, expression of the transactivator, either combined on the same construct or elsewhere in the genome or cell.

3. Using a Specific Effector Molecule

Specificity in phenotypic consequence can also be introduced by use of a specific effector molecule. Where a molecule, e.g. RNA or protein, expressed under the control of any of the expression systems described herein, has a specific effect only in particular cells, tissues, or sex, etc, then phenotypic specificity can be obtained with broader or less specific expression of the transactivator. For example, in the context of a RIDL-type mass-release insect population control programme, using the system to express a molecule only toxic, or preferentially toxic, to pre-adult stages, results in adults which are fully, or reasonably competitive, relative to wild type. This is desirable as the effectiveness of the programme depends on the competitiveness and longevity of the adult forms, when released into the wild. Since their internal repressor (e.g. tetracycline) concentration is likely to decline in the wild, it would be advantageous to ensure that induction (de-repression) of the expression system, as and when it occurs in adults, has a minimal negative effect on them.

As another example, sex separation, or sex-specific effects, can be achieved by expression in both males and females of a molecule with differential effects in males and females. For example, expression of the Transformer protein in male *Drosophila* will tend to transform them into females, but have no effect on females. Similarly, expression of Male specific lethal-2 (Ms1-2) protein in *Drosophila* will tend to kill females, but not males (Gebauer et al, 1998; Kelley et al, 1995; Matsuo et al., 1997; Thomas et al, 2000). Conversely, expression of a partially self-complementary RNA molecule with substantial homology in its self-complementary or double-strand-forming region to ("hairpin RNA against") transformer will tend to transform genetic females into phenotypic males, while not affecting genetic males, and expression of hairpin RNA against msl-2 will tend to be lethal to males but not to females. Expression of hairpin RNA against the male- or female-specific exons of doublesex will tend to affect those sexes only, and simultaneous expression of RNA encoding the other form of doublesex (i.e. $Dsx^M$ in females or $Dsx^F$ in males) will tend to modify or enhance this effect. This simultaneous expression of a protein and a hairpin RNA molecule can readily be accomplished by combining the bicistronic or fusion protein approach described above with expression of a hairpin RNA using the bi-directional expression system also described above. Sex-, stage- or other specificity can be further added to such a system by incorporation of appropriate specific splicing or other transcriptional, translational or other post-translational control signals to either part of the system as will be apparent to the person skilled in the art.

Multi-functional hairpin RNA molecules may be constructed and are envisaged. For example, RNAi against transformer in the Mediterranean fruit fly *Ceratitis capitata* Wiedmann (medfly) will tend to transform genetic females into fertile males. For an area-wide population control program based on mass-release of such insects, it is preferable to sterilise the released flies. This can be accomplished by using a composite RNA molecule that simultaneously disrupts expression of both transformer and a gene required for spermatogenesis or embryonic or larval viability. Many such genes are known in *Drosophila* with homologues in mosquitoes or other animals. With medfly, a suitable homologue can readily be isolated, using techniques known to those skilled in the art. We prefer the use of a gene which allows the production of seminal fluid, and preferably also of sperm, to reduce the tendency of the female to re-mate after insemination by the affected male. We particularly prefer to direct this second part of the hairpin RNAi molecule against a paternal effect lethal, so that no viable progeny can be produced, or against a zygotically expressed gene required for embryonic or larval viability or development, so that progeny inheriting the construct will be affected. Other configurations are envisioned and will be readily apparent to those skilled in the art: for example expression of a female-specific lethal protein by bicistronic expression and a hairpin RNA leading to paternal-effect lethality by bi-directional expression. In common with the composite hairpin RNA against a suitable sex-determination gene and a paternal effect lethal, this allows the generation of a single-sex (male-only) population of insects, all of whose progeny die through the action of the paternal-effect lethal, irrespective of whether their progeny or mates feed on tetracycline. Thus, the present invention provides a controlled promoter, as defined, wherein the promoter is operably linked with DNA encoding an RNAi causing lethality or sterility. In this case, lethality may correspond to low fitness, such as flightless, rather than outright lethality, provided that the likelihood of breeding on is substantially reduced.

4. Using Site-Specific Recombinase(s)

Specificity can also be introduced into the positive feedback system by inserting a "stuffer" fragment which inactivates it. If this "stuffer" fragment is flanked by target sites for a suitable site-specific recombinase, then it will tend to be excised in the presence of active recombinase. Any system for selective expression of active recombinase, for example, expression of the recombinase under the control of a female-specific promoter, will therefore tend to lead to selective expression of the positive feedback system, in this case in females only. If the recombinase is expressed in somatic cells only, for example by using the method described above, then the version transmitted to the next generation includes the stuffer fragment, which can again be daughters but not sons. Conversely, if the recombinase is expressed in the genome only, provision of active recombinase will lead to offspring in which the expression system is active, from parents in which it is inactive. This can be used, for example, to generate gametes containing an active dominant lethal or sterile gene system (e.g. female-specific or non-sex-specific) for use in an insect population control strategy.

In a preferred embodiment, the stuffer fragment encodes the recombinase. This embodiment is particularly compact. In another preferred embodiment, the stuffer fragment encodes a transcriptional repressor which tends to inactivate the positive feedback expression system—this embodiment tends to reduce the basal expression of the system in the presence of the stuffer fragment.

Conversely, the system can be specifically inactivated in certain cells, or clones of cells, by introducing target sites for a suitable site-specific recombinase at suitable positions, and then expressing or introducing the appropriate active recombinase in appropriate cells, such that one or more key functional elements of the expression system are removed or disrupted by recombination between the target sites for the recombinase.

Suitable recombinase systems include cre/lox and Flp/FRT.

The present invention is illustrated by the following, non-limiting, Examples. In the following Examples, the Figures are as follows.

EXAMPLES

A series of constructs was made with tTA in a positive feedback configuration, i.e. with tTA expression regulated by tTA binding to tetO. Transgenic insects carrying these constructs were obtained and their properties analysed.

tTAV

In some cases, the intention was to obtain very high levels of expression of tTA in the absence of tetracycline. In various exemplified constructs described hereinbelow, tTA expression was so high as to be lethal. As part of the process of obtaining strong expression of tTA, part of the tTA open reading frame was redesigned to express a similar protein, but with codon usage closer to the norm for *Drosophila melanogaster*, and lacking some potential cryptic splice sites present in the original nucleotide sequence. This variant tTA sequence was named tTAV (SEQ ID NO. 31, protein sequence SEQ ID NO. 32).

Example 1

WTP-tTA and JY2004-tTA in *Drosophila melanogaster*

The tTA coding region (SEQ ID NO. 29, tTA protein sequence SEQ ID NO. 30) from pUHD15-1 (SEQ ID NO. 33, Gossen et al., 1994; Gossen and Bujard, 1992) was placed under tetO control, in a positive feedback configuration, by inserting it into pWTP2 (Bello et al, 1998) or pJY2004, a version of pJY2000 that lacks insulators (Stebbins and Yin, 2001). These constructs were named pWTP-tTA and pJY2004-tTA, respectively. A diagram of $tetO_7$-tTA region of pJY2004 is provided as accompanying FIG. 5, and is SEQ ID NO. 14.

Figure 1:
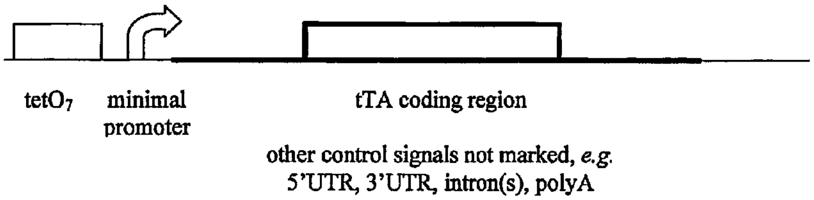
FIG. 1 shows a tetracycline-repressible transcription activator scenario.
Figure 2:
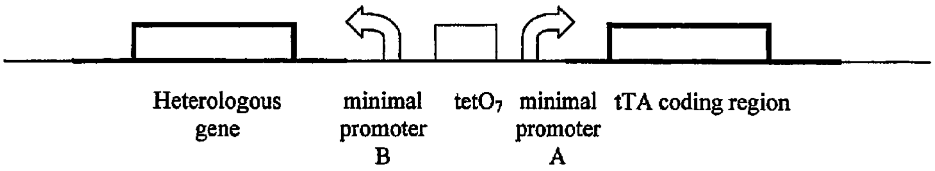
FIG. 2 shows a system of the invention using a bi-directional enhancer.
Figure 3:
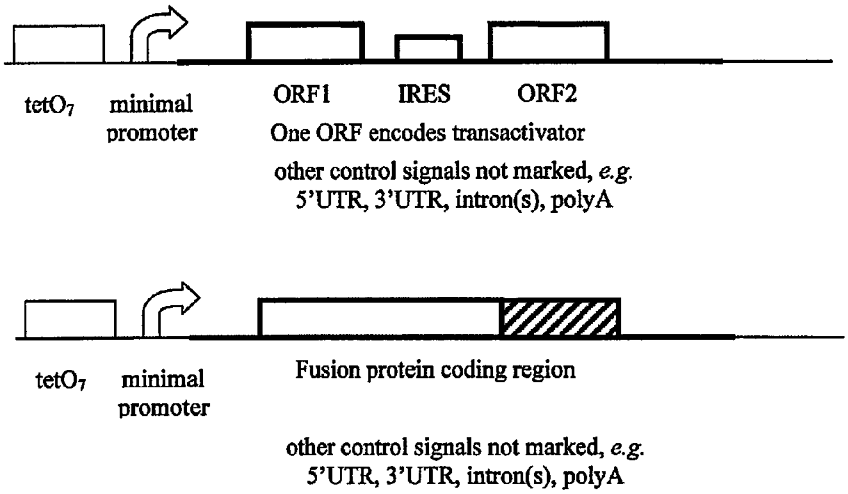
FIG. 3 shows a sex-specific system.
Figure 4:
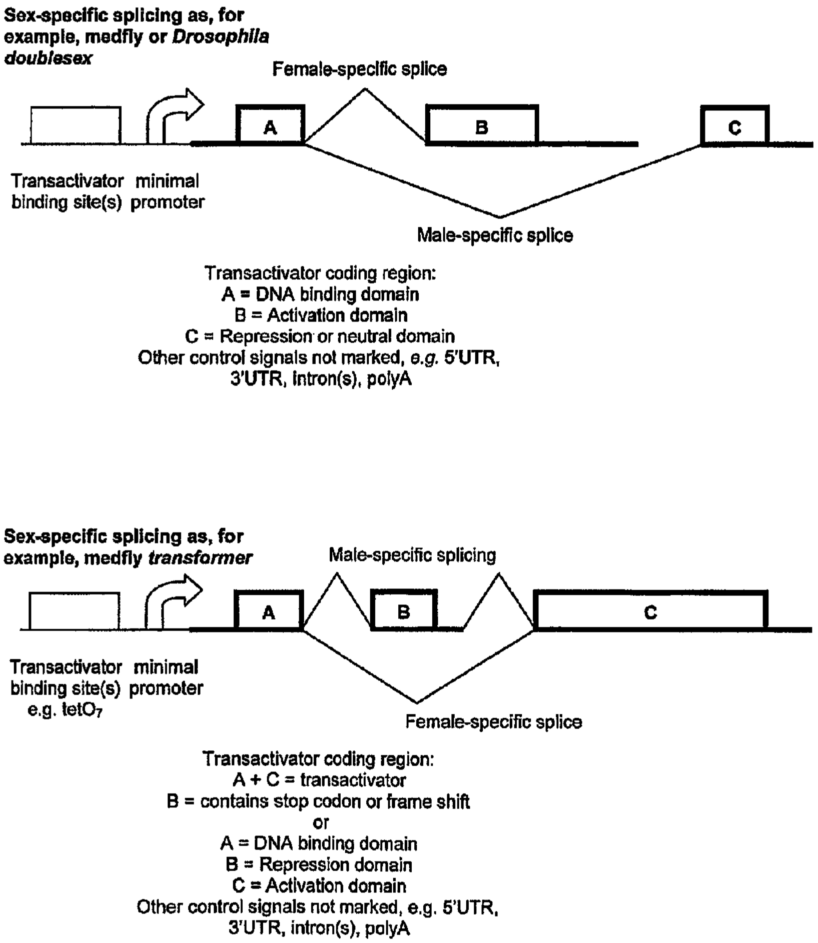
FIG. 4 shows another sex-specific system.
Figure 5:
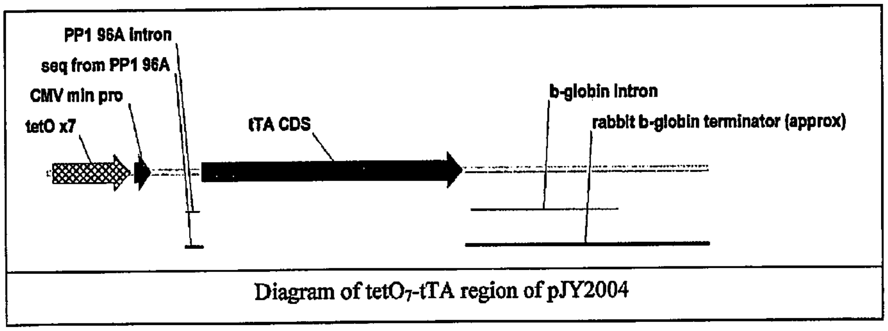
FIG. 5 is a diagram of the $tetO_7$-tTA region of pJY2004.

In pWTP-tTA, the $tetO_7$ binding sites are followed by a minimal promoter from the P element, a leader sequence from *Drosophila* hsp70, a short intron from the *Drosophila* PP1α96A gene, the tTA coding region and a transcription terminator from *Drosophila* hsp70. In pJY2004-tTA, the minimal promoter and leader sequences are from CMV, followed by the tTA coding region and a transcription terminator from rabbit β-globin, as shown in FIG. 5.

Transgenic *Drosophila melanogaster* carrying either of these constructs were fully viable, even without dietary tetracycline. Insects doubly heterozygous for WTP-EGFP and either of these constructs were examined for green fluorescence characteristic of EGFP expression. Insects with WTP-tTA and WTP-EGFP showed very weak fluorescence only slightly above background autofluorescence. In contrast, insects with JY2004-tTA and WTP-EGFP showed strong fluorescence, similar to that seen in insects carrying EGFP under the control of the Actin5C promoter, which is widely used as a strong, constitutive promoter in *Drosophila* (e.g. Reichhart and Ferrandon, 1998). Expression of EGFP was repressed to undetectable levels when the insects were raised on diet supplemented with tetracycline to 100 μg/ml. Control insects heterozygous for either WTP-EGFP, JY2004-tTA or WTP-tTA showed no fluorescence above background whether or not they were raised on a diet containing tetracycline.

We placed tTA under the control of the Actin5C promoter, in plasmid pP [Casper-Act5C-tTA]. Transgenic flies carrying this construct and WTP-EGFP, raised on a diet lacking tetracycline, showed green fluorescence at a comparable intensity to that observed in equivalent flies with JY2004-tTA and WTP-EGFP.

These results show that positive feedback constructs can be used to give strong (JY2004-tTA) or weak (WTP-tTA), tetracycline-repressible expression from a suitable construct (here WTP-EGFP).

EGFP is widely used as a neutral reporter. We further tested JY2004-tTA flies by crossing them to flies with constructs capable of expressing proteins known or predicted to be deleterious. We inserted the central domain of Nipp1Dm (Bennett et al, 2003; Parker et al, 2002) ("nipper"), into pJY2004, to make pJY2004-nipper, and transformed *Drosophila* with this construct. We also used flies carrying tetO-hid (Heinrich and Scott, 2000). In each case, crossing to JY2004-tTA flies gave tetracycline-repressible lethality. Data from two example crosses are presented in Table 2, below.

TABLE 2

Use of positive feedback constructs to drive expression of lethal genes in *Drosophila*.

| JY2004-tTA | CyO | [tetracycline] (μg/ml) |
|---|---|---|
| Male JY2004-tTA/CyO x Female tetO-hid/tetO-hid | | |
| 0 | 15 | 0 |
| 9 | 10 | 100 |
| Male JY2004-tTA/CyO x Female JY2004-nipper/JY2004-nipper | | |
| 0 | 20 | 0 |
| 16 | 13 | 100 |

Example 2

LA513 in *Drosophila melanogaster*

Figure 6:
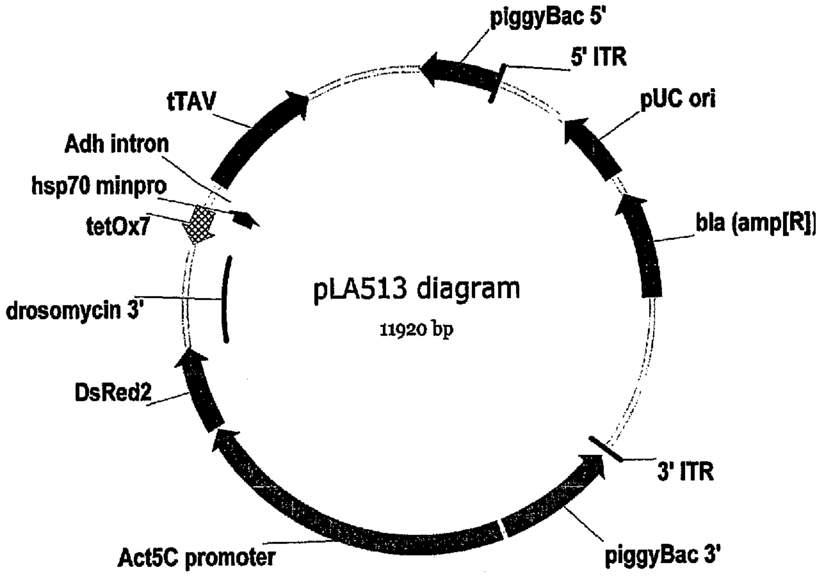
FIG. 6 is a schematic diagram of pLA513.
Figure 7:
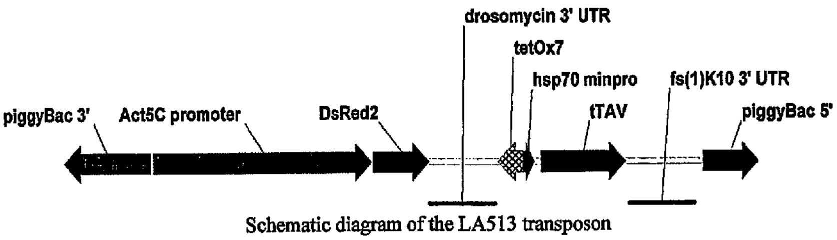
FIG. 7 is a schematic diagram of the LA513 transposon.

We made construct pLA513 (SEQ ID NO. 16, schematic diagram shown in FIG. 6), containing a non-autonomous piggyBac transposon. We generated transgenic *Drosophila melanogaster* carrying this construct by co-injection with a helper plasmid into a white-eyed strain (Handler, 2002; Handler and James, 2000). Potential transgenics were screened for fluorescence characteristic of DsRed2. 5 transgenic lines were recovered, and were designated O513, M8, M13, F23 and F24. A schematic diagram of the LA513 transposon is shown in accompanying FIG. 7.

*Drosophila melanogaster* stocks were maintained at 25° C. on yeast/sugar/maize/tetracycline medium (tetracycline (Sigma) at 100 μg/ml final concentration), unless stated otherwise. All experiments were performed at 25° C.

Survival of LA513/+ Transgenics With and Without Tetracycline

Heterozygous transgenics were crossed in at least triplicate to wild type on media with or without Tc (tetracycline). In the absence of any lethality, it would be expected that approximately half the progeny of such a cross would be transgenic. Progeny were scored as young adults for DsRed marker fluorescence [Matz et al, 1999] using an Olympus SZX12 microscope with fluorescence capability, and the ratio of fluorescent (transgenic) to total flies was calculated. The results are shown in Table 3, below. In these experiments, all 5 transgenic lines showed 100% lethality, in the absence of tetracycline, and good survival (i.e. fluorescent:non-fluorescent ratio ~1:1), in the presence of 100 μg/ml tetracycline. Inspection of the vials showed few or no large fluorescent larvae in the absence of Tc, although many very small fluorescent larvae were present, at a time when non-fluorescent (wild type for LA513) larvae were visible at all sizes. This suggests that, in the absence of tetracycline, LA513 causes lethality at an early (embryonic and/or early larval) developmental stage.

TABLE 3

LA513 insertions are tetracycline-repressible dominant lethals

| | 0 μg/ml tetracycline | | 100 μg/ml tetracycline | | |
|---|---|---|---|---|---|
| LA513 line | # Flies | # Fluorescent | # Flies | # Fluorescent | Ratio |
| O513 | 490 | 0 | 1963 | 937 | 0.48 |
| M8 | 74 | 0 | 66 | 25 | 0.38 |
| M13 | 657 | 0 | 1838 | 892 | 0.49 |
| F23 | 473 | 0 | 1914 | 845 | 0.44 |
| F24 | 61 | 0 | 114 | 60 | 0.53 |
| Total | 1755 | 0 | 5895 | 2759 | 0.47 |

Dominant lethality could have several causes. Without being restricted by theory, it seems likely that, in the absence of tetracycline, tTAV accumulates to a relatively high concentration and that this is lethal, possibly due to transcriptional squelching, or interference with protein degradation. An alternative is that, in the absence of tetracycline, tTAV binds to tetO and acts as a long-range enhancer, perturbing the expression of genes near to the LA513 insertion. This appears unlikely, as all 5 transgenic lines gave similar results. Each of these lines was derived from a different G0 injection survivor, and these lines are, therefore, likely to carry LA513 integrated at different genomic sites. We verified this by inverse PCR. Table 4, below, shows the integration sites for 3 of the lines; in each case the LA513 insertion was at a TTAA sequence, as expected from the known insertion site preference of the piggyBac transposon. As expected, the 3 insertions were indeed at 3 different sites in the *Drosophila* genome.

TABLE 4

| Insertion sites of LA513 in *Drosophila* genome | | | | |
|---|---|---|---|---|
| Line | Sequence Amplified or at Site of Integration | Predicted chromosome arm | Predicted *Drosophila* cytology | Nearest predicted gene |
| 0513 | Cacagcgcatgatgagcaca**TTAA**caaaatgtagtaaaatagga (SEQ ID NO. 1) | 2L | 25F4-25F5 | CG9171 |
| M8 | Gtttcgataaatattgctat**TTAA**aatgcttattttcaatgcta (SEQ ID NO. 2) | 2L | 36F6-36F6 | CG15160 |
| F24 | Tttgttttctaacgttaaag**TTAA**agagagtccagccacatttt (SEQ ID NO. 3) | 2L | 21C4-21C5 | CG13691 |

Flanking sequence is shown with the TTAA insertion site capitalised. Predicted chromosome locations, and the nearest predicted gene, are also shown; these are based on the published *Drosophila* genome sequence.

Example 3

Reducing the Toxicity of tTAV

Figure 8:
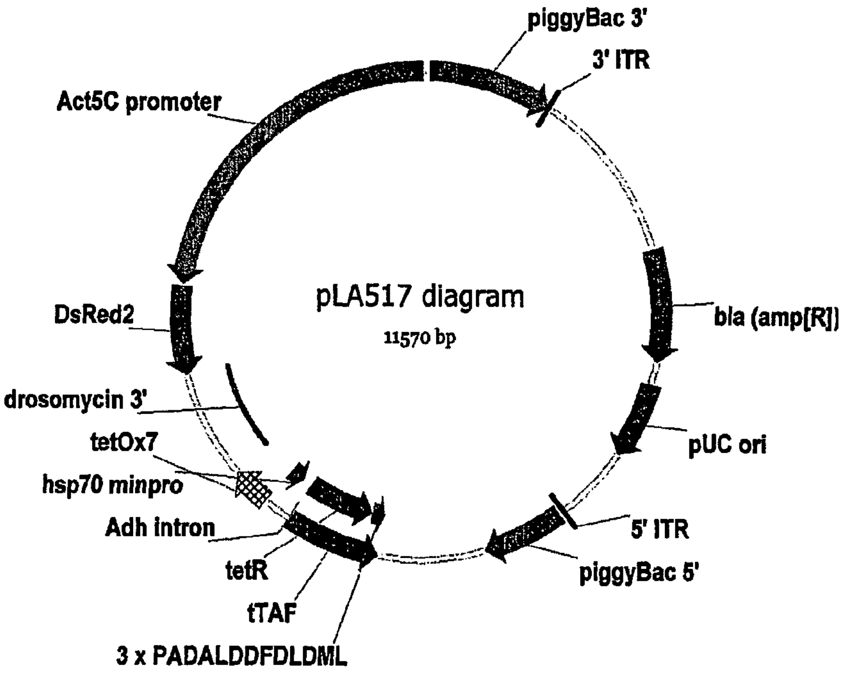
FIG. 8 is a schematic diagram of pLA517.

The toxic effect of high level expression of tTAV is thought to be due to transcriptional squelching and/or interference with ubiquitin-dependent proteolysis, via the VP16-derived section (Gossen and Bujard, 1992; Salghetti et al., 2001). We, therefore, modified tTAV by removing the VP16 section and replacing it with a synthetic sequence which encodes 3 copies of a peptide (PADALDDFDLDML) derived from VP16 (Baron and Bujard, 2000; Baron et al., 1997). This derivative was named tTAF; the resulting plasmid was named pLA517, and is SEQ ID NO. 17, and is shown, diagrammatically, in accompanying FIG. 8.

*Drosophila melanogaster* were transformed with this construct, and one transgenic line was obtained. LA513 heterozygous males were crossed to wild type (for LA513) females and the progeny scored for fluorescence (as adults). If all progeny are equally likely to survive, the expected proportion of the total progeny that are fluorescent is 50%. In the absence of tetracycline, this proportion was 32%, only a modest reduction compared with 48% when parents and progeny were raised on diet supplemented with tetracycline to 100 μg/ml. The results are shown in Table 5, below. We tested whether supplying tetracycline in the diet of the parents but not of the progeny could reduce this lethality. In this case, we observed an intermediate proportion of 0.37, indicating that maternally contributed tetracycline has a modest beneficial effect.

TABLE 5

| Effect of tetracycline on the survival of LA517/+ *Drosophila* and their +/+ siblings | | | |
|---|---|---|---|
| LA517 Parent [Tc] μg/ml | Progeny [Tc] μg/ml | Non-Fluorescent | Fluorescent |
| 0 | 0 | 165 | 78 |
| 100 | 100 | 524 | 482 |
| 100 | 0 | 502 | 297 |

Since LA517, alone, had little impact on viability, unlike the closely related construct LA513, we tested whether it was capable of driving expression of a heterologous gene under tetO control. For this we used tetO-hid (Heinrich and Scott, 2000). Flies homozygous for tetO-hid were crossed with flies heterozygous for LA517. In the absence of tetracycline, only 3.4% of the adult progeny carried LA517. In the presence of 100 μg/ml tetracycline, this proportion was 42%. LA517 is, therefore, capable of driving effective expression of a heterologous gene.

TABLE 6

| Effect of tetracycline on the survival of LA517/+, +/tetO-hid *Drosophila* and their +/+, +/tetO-hid siblings TetO-Hid × LA517/+ | | |
|---|---|---|
| [Tc] | Non-Fluorescent | Fluorescent |
| 0 | 636 | 23 |
| 100 | 174 | 127 |

Example 4

Use of Analogues of Tetracycline

Line F23 was used to determine whether chemical analogues of tetracycline could be used in place of tetracycline to suppress the lethality of LA513. For this purpose we tested 3 analogues at a range of concentrations from 0 to 100 μg/ml (suppliers: tetracycline and doxycycline, Sigma; 4-epi-oxytetracycline, Acros Organics; chlortetracycline Fuzhou Antibiotic Group Corp.). We calculated the concentrations required for half-maximal survival. These are shown in Table 7, below.

TABLE 7

| Efficacy of Tc analogues | | |
|---|---|---|
| Line | Tc/Analogue | Concentration for half-maximal survival, μg/ml |
| F23 | Tetracycline | 5.0 |
| F23 | Doxycycline | 3.9 |
| F23 | 7-chlortetracycline | 1.7 |
| F23 | 4-epi-oxytetracycline | 42.0 |

Example 5

Longevity of LA513/+ Adults in the Absence of Tetracycline

LA513 clearly confers dominant lethality, active at an embryonic and/or early larval stage. Larvae were raised on a diet supplemented with 100 μg/ml tetracycline. After eclosion, adults were transferred to a diet lacking tetracycline. The lifespan of these adults was measured, and also of comparable $w^{1118}$ non-transgenic adults. As shown in Table 8, below, the transgenic lines showed good adult survival relative to the non-transgenic control. This suggests that stage-specificity can be obtained in this way—here LA513 is a larval/embryonic lethal, but not an adult lethal.

TABLE 8

Mean adult lifespan of LA513/+ transgenic *Drosophila*.

| Line | Mean post-eclosion survival time, days | Standard deviation | Number of Flies |
|---|---|---|---|
| O513 | 40.3 | 12.3 | 66 |
| M8 | 26.1 | 2.5 | 9 |
| M13 | 29.5 | 9.9 | 47 |
| F23 | 29.6 | 11.3 | 83 |
| F24 | 19.9 | 10.0 | 9 |
| $w^{1118}$ | 22.2 | 8.6 | 88 |

It is possible to explain these longevity data by postulating that larvae accumulate tetracycline by feeding, and retain this tetracycline into adulthood, so that they survive even in the absence of dietary tetracycline as adults. To examine this, flies heterozygous for LA513/+ (M13 line) were raised as larvae on various concentrations of tetracycline. After eclosion, adults were transferred to diet lacking tetracycline and the lifespan of these adults was measured, as above. As shown in Table 9, below, the concentration of dietary tetracycline as larvae had no obvious effect on subsequent adult longevity in the absence of tetracycline, implying that adult survival is not primarily due to retention of tetracycline from larval feeding. At a concentration of 1 μg/ml, no transgenics survived to adulthood, and at 3 μg/ml only about half of the expected number survived to adulthood, so that this concentration is close to the minimum for larval survival.

TABLE 9

Effect of larval tetracycline on adult longevity

| Larval tetracycline μg/ml | Mean post-eclosion survival time, days | Standard deviation | Number of Flies |
|---|---|---|---|
| 1 | — | — | — |
| 3 | 33.5 | 13.2 | 9 |
| 10 | 28.4 | 9.6 | 17 |
| 30 | 26.3 | 11.3 | 23 |
| 100 | 29.5 | 9.9 | 47 |

Another possible explanation for the survival of LA513/+ adults is that tTAV is inactive in adults, so that the positive feedback cycle does not work, and tTAV does not accumulate. We examined this by measuring the amount of tTAV mRNA by quantitative PCR following a reverse transcriptase reaction (quantitative rt-PCR, or qPCR). We used Taqman chemistry and reagents (ABI), and an ABI Prism 7000 qPCR instrument. Each sample was assayed in triplicate; data are the mean of these three assays. The 18S primers anneal to *Drosophila melanogaster, Ceratitis capitata* and *Aedes aegypti* 18S RNA, so these primers were used for all three species.

Priners Used:

| | | SEQ ID NO. |
|---|---|---|
| 18S RNA | | |
| Forward Primer: | ACGCGAGAGGTGAAATTCTTG | 4 |
| Reverse Primer: | GAAAACATCTTTGGCAAATGGTT | 5 |
| TaqMan MGB Probe: | 6-Fam-CCGTCGTAAGACTAAC-MGB | 6 |
| tTAV | | |
| Forward Primer: | CATGCCGACGCGCTAGA | 7 |
| Reverse Primer: | GTAAACATCTGCTCAAACTCGAAGTC | 8 |
| TaqMan MGB Probe: | VIC-TCGATCTGGACATGTTGG-MGB | 9 |

We found that O513 raised on 100 μg/ml tetracycline had a tTA:18S ratio of 0.00016 (larvae) and 0.00013 (adult). Adults raised as larvae on 100 μg/ml tetracycline, but then transferred to non-tetracycline diet as adults had ratios of 0.0061, 0.0047, 0.0087 and 0.011 after 1, 2, 4 and 8 days without tetracycline, respectively. This 28- to 64-fold increase in expression relative to the tetracycline-fed control indicates that the tTAV-based positive feedback expression system is functional in adults.

Example 6

LA513 in *Aedes aegypti*

*Aedes aegypti* (the yellow fever mosquito, also the major vector of urban dengue fever) were transformed with LA513. Two independent insertion lines, LA513A and LA513B, were obtained.

Males heterozygous for LA513A (reared as larvae on 30 μg/ml tetracycline) were allowed to mate with wild type females. Eggs were collected and the resulting larvae raised in normal media, or in media supplemented with tetracycline (Tc) to 30 μg/ml. The number of transgenic and non-transgenic adults resulting from these eggs was determined. Data are the sum of at least 5 experiments. Larvae were reared at a density of ≤250 individuals per litre; all the eggs in "no tetracycline" experiments were washed twice before submergence to avoid transferring tetracycline. For the "with tetracycline" experiments, the parental blood and sugar-water was supplemented with tetracycline to 30 μg/ml; for the "no tetracycline" experiments it was not. $\chi^2$ test for differentiation in ratio of the transgene and wild types for survival to adult: "with tetracycline", either orientation: P>0.05; "without tetracycline, either orientation P<0.001 (null hypothesis: genotype with respect to LA513 has no effect on survival).

LA513A is, therefore, a repressible dominant lethal, with a penetrance in these experiments of 95-97%. LA513B is also a repressible dominant lethal, with a penetrance in these experiments of 100%. The results are shown in Table 10, below.

TABLE 10

Effect of tetracycline on the survival of LA513/+ *Aedes aegypti* and their +/+ siblings.

| Parents | | | | Progeny | | | | | | |
|---|---|---|---|---|---|---|---|---|---|---|
| Male | Female | Egg | Tc as larvae | Genotype | 1st instar larvae | 2nd | 3rd | 4th | Pupae | Adults |
| LA513A/+ | +/+ | 1000 | Yes | LA513A/+ | 489 | 468 | 446 | 442 | 437 | 434 |
| | | | | Wild type | 444 | 431 | 403 | 400 | 396 | 392 |
| +/+ | LA513A/+ | 1000 | Yes | LA513A/+ | 442 | 420 | 404 | 399 | 393 | 383 |
| | | | | Wild type | 466 | 444 | 428 | 417 | 412 | 404 |
| LA513A/+ | +/+ | 540 | No | LA513A/+ | 274 | 265 | 235 | 208 | 155 | 7 |
| | | | | Wild type | 233 | 225 | 214 | 212 | 209 | 206 |
| +/+ | LA513A/+ | 497 | No | LA513A/+ | 216 | 205 | 181 | 168 | 131 | 9 |
| | | | | Wild type | 241 | 225 | 216 | 214 | 211 | 207 |
| LA513B/+ | +/+ | 377 | Yes | LA513B/+ | 161 | 153 | 147 | 141 | 139 | 131 |
| | | | | Wild type | 178 | 171 | 165 | 160 | 157 | 153 |
| +/+ | LA513B/+ | 442 | Yes | LA513B/+ | 189 | 181 | 170 | 166 | 161 | 153 |
| | | | | Wild type | 203 | 198 | 185 | 182 | 180 | 176 |
| LA513B/+ | +/+ | 188 | No | LA513B/+ | 69 | 19 | 0 | 0 | 0 | 0 |
| | | | | Wild type | 85 | 84 | 83 | 83 | 82 | 81 |
| +/+ | LA513B/+ | 240 | No | LA513B/+ | 91 | 60 | 0 | 0 | 0 | 0 |
| | | | | Wild type | 107 | 104 | 99 | 98 | 95 | 93 |

We examined the survival of LA513A/+ males that had been raised on tetracycline (30 μg/ml), as larvae, but not given tetracycline as adults. We found that all males tested survived for three weeks, irrespective of genotype (LA513A/LA513A, LA513A/+ or +/+) or the presence or absence of tetracycline in their diet (n≥40 for each genotype).

We examined the survival of LA513A/+ males that had been raised on tetracycline (30 μg/ml), as larvae, but not given tetracycline as adults. We found that all males tested survived for three weeks, irrespective of genotype (LA513A/LA513A, LA513A/+ or +/+) or the presence or absence of tetracycline in their diet (n≥40 for each genotype).

We investigated the induction kinetics of tTAV in adult LA513B/+ mosquitoes after withdrawal of tetracycline, using qPCR. As shown in Table 11, below, tTAV increased in males and females following withdrawal of tetracycline. Induction of tTA expression is fairly rapid after removal of Tc, as with *Drosophila*. In each case, shifting between diets containing different levels of tetracycline provides a level of control over the expression level of genes controlled by tTA (here exemplified by tTA itself), using such a positive feedback system.

TABLE 11

Induction of tTA expression in LA513B/+ males following withdrawal of tetracycline

| Sex | Time (days) without tetracycline | tTA:18S expression ratio | tTA:18S expression relative to male with tetracycline |
|---|---|---|---|
| Male | 0 | 0.00036 | 1 |
| Female | 0 | 0.00060 | 1.7 |
| Male | 3 | 0.0043 | 12 |
| Female | 3 | 0.014 | 38 |
| Male | 4 | 0.054 | 150 |
| Female | 4 | 0.019 | 530 |
| Male | 8 | 0.012 | 34 |
| Female | 8 | 0.52 | 1500 |
| Male | 16 | 0.10 | 280 |
| Female | 16 | 0.032 | 88 |

Example 7

Tetracycline-Repressible Enhancement of a Nearby Promoter by tTAV in a Positive Feedback Configuration We observed that the fluorescent marker in LA513A and LA513B transgenic mosquitoes showed a different pattern of fluorescence in the absence of tetracycline, compared with the pattern in the presence of tetracycline. Fluorescence in the presence of tetracycline was typical of Actin5C-driven expression in mosquitoes (Catteruccia et al, 2000; Pinkerton et al., 2000), and limited largely to the swollen part of the thorax. In contrast, in the absence of tetracycline, expression was much stronger and evident substantially throughout the body of transgenic individuals. In each case, assessment of fluorescence intensity and expression pattern was made by visual observation using fluorescence microscopy.

Elevated expression of tTAV in this positive feedback situation appears, therefore, to be stimulating expression from the nearby Actin5C promoter. This is illustrated, diagrammatically, in FIG. 9. We also found that intermediate concentrations of tetracycline, just sufficient substantially to suppress the lethality of LA513, did not suppress this broader expression pattern of fluorescence. At these intermediate concentrations of tetracycline, tTAV accumulates to an intermediate level—sub-lethal, but higher than in 30 μg/ml tetracycline, and which still influences the expression of DsRed2. This again exemplifies the additional control available by modulating tetracycline concentration.

Figure 9:
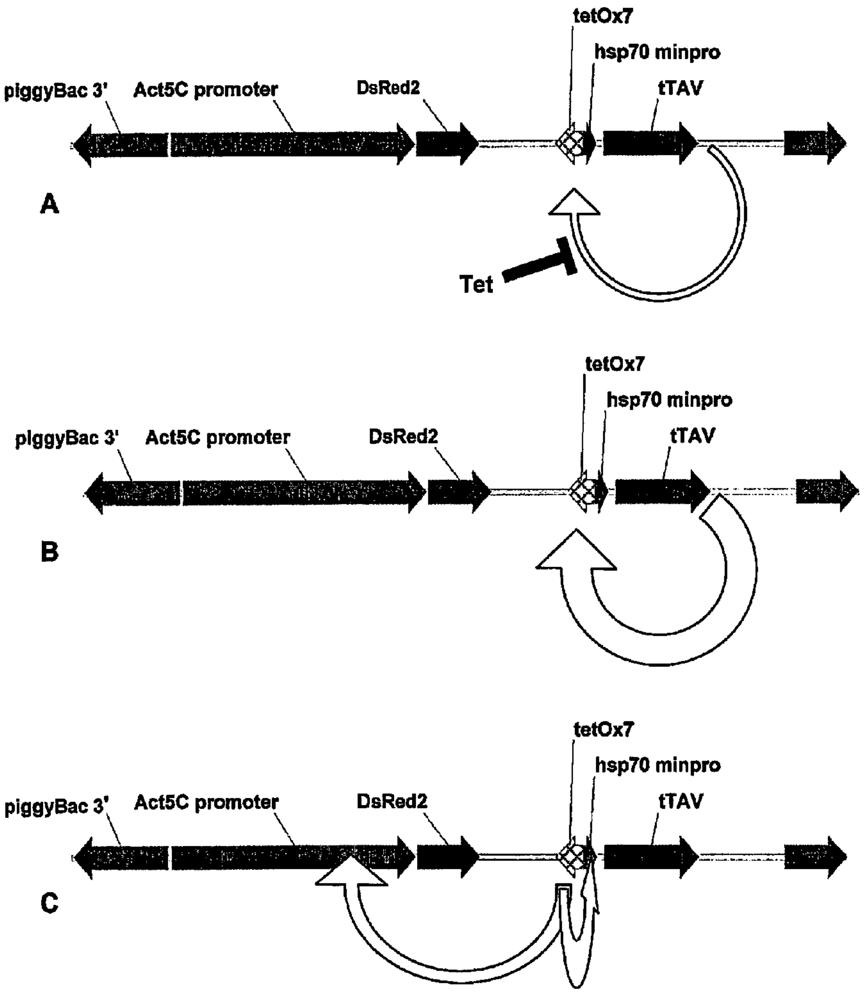
FIG. 9 illustrates the bidirectional action of $tetO_7$ in 513A and 513B mosquitoes.

FIG. 9 illustrates the bidirectional action of $tetO_7$ in 513A and 513B mosquitoes. In 513, DsRed2 is under the transcriptional control of the *Drosophila* Actin5C promoter.

(A) In the presence of tetracycline, relatively little tTAV is produced, this binds tetracycline and has little or no effect on DsRed2 expression. DsRed2 is seen in a pattern typical of Actin5C expression in mosquitoes.

(B) In the absence of tetracycline, tTAV stimulates its own expression in a positive feedback loop.

(C) tTAV binding to the tetO sites enhances expression of both the hsp70 minimal promoter, and hence tTAV, but also the Actin5C promoter, and hence DsRed2.

Example 8

LA656, LA928 and LA1124 in *Ceratitis capitata*

Figure 10:
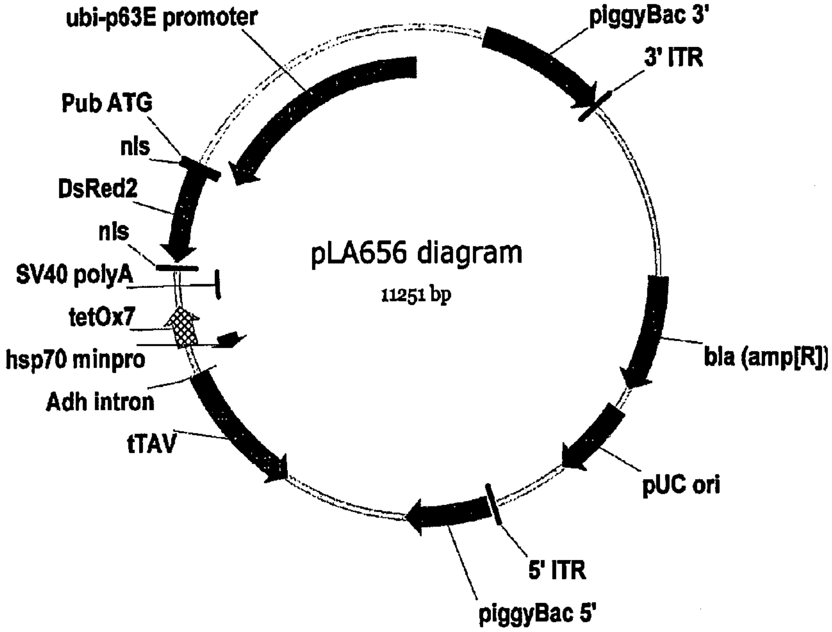
FIG. 10 is a schematic diagram of pLA656.
Figure 11:
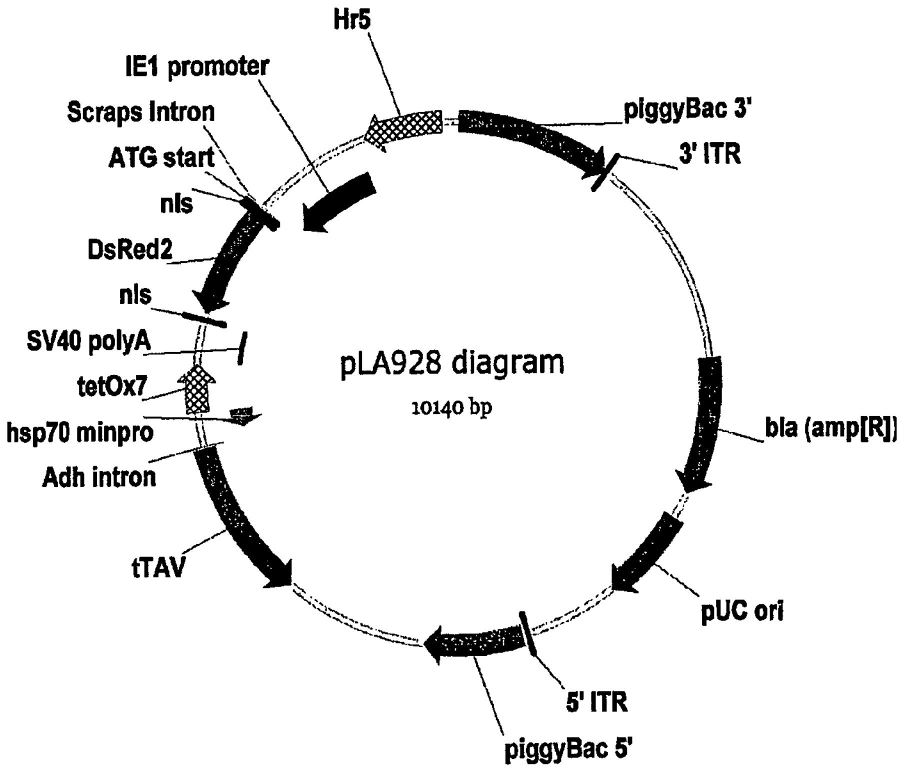
FIG. 11 is a schematic diagram of pLA928.
Figure 12:
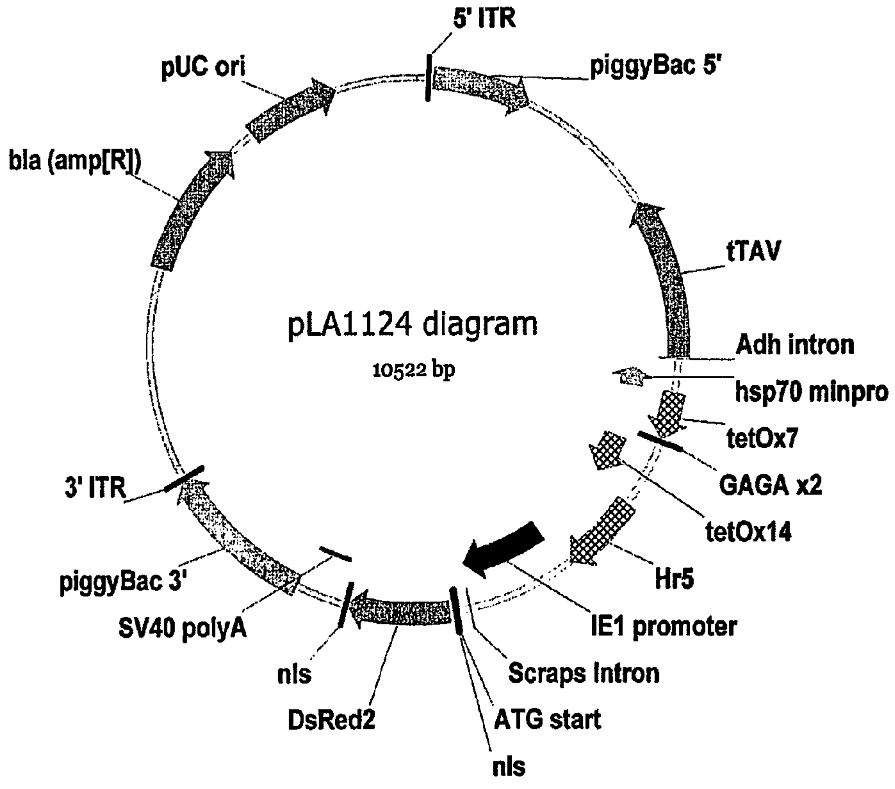
FIG. 12 is a schematic diagram of pLA1124.

No transgenic lines of the Mediterranean fruit fly (medfly, *Ceratitis capitata* Wiedmann) were obtained, using pLA513, probably indicating that the Actin5C-based marker of pLA513 is inappropriate for use in medfly. This emphasises the desirability of expression constructs with a wide species range. We, therefore, modified the construct to include a polyubiquitin (ubi-p63E)-based marker instead of the Actin5C-based one of pLA513. One such construct is pLA656. We also made two additional constructs, pLA928 and pLA1124 (SEQ ID NO's 18, 20 and 21, respectively, and shown, diagrammatically, in FIGS. 10, 11 and 12), using a marker based on the hr5 enhancer and ie1 promoter from a baculovirus (*Autographica californica* nuclear polyhedrosis virus, AcMNPV). These differ in the orientation of the marker with respect to the tetO-tTAV cassette. The hr enhancer is closer to the tetO-tTAV cassette in pLA1124 than in pLA928. Furthermore, pLA1124 has 21, rather than 7, copies of tetO and additionally has a putative GAGA-factor binding region related to that of pUASp (Rorth, 1998).

One transgenic line was obtained from pLA656, three for pLA928, and three for pLA1124. These lines are assumed to have independent insertions, as they were derived from different G0 injection survivors.

Males heterozygous for each line were crossed to wild type females. The progeny were raised on standard yeast/sugar/wheatgerm or yeast/sugar/maize *Drosophila* diet, supplemented with tetracycline as appropriate. The parents were raised on the same diet, supplemented with tetracycline to 100 μg/ml in the case of the transgenic males. The wild type females to which these males were mated were raised without tetracycline, to eliminate any potential maternal contribution of tetracycline. The number of transgenic and non-transgenic pupae and adults obtained from each cross was determined by scoring for DsRed2 by fluorescence microscopy.

The results of these crosses are shown in Table 12, below. In each case, in the absence of tetracycline, survival of the heterozygous transgenics was less than 2% relative to their wild type shifting between diets containing different levels of tetracycline, modifying the construct, and using position effect, are discussed elsewhere herein.

TABLE 12

Effect of tetracycline on the survival of transgenic medfly heterozygous for various constructs, and their +/+ siblings

| | Progeny [Tc] (μg/ml) | F/NF pupae | Pupal survival ratio (%) | F male | F female | NF male | NF female | Adult survival ratio (%) |
|---|---|---|---|---|---|---|---|---|
| LA656 | 0 | 84/1161 | 7 | 6 | 2 | 530 | 551 | 0.7 |
| | 0.1 | 16/423 | 4 | 0 | 0 | 205 | 177 | 0 |
| | 1 | 124/384 | 32 | 34 | 12 | 155 | 174 | 14 |
| | 3 | 258/370 | 70 | 84 | 53 | 165 | 133 | 46 |
| | 10 | 249/252 | 99 | 91 | 98 | 107 | 127 | 81 |
| | 100 | 330/307 | 107 | 151 | 150 | 134 | 148 | 107 |
| LA928m1 | 0 | 28/1499 | 1.87 | 5 | 1 | 661 | 639 | 0.46 |
| | 0.1 | 0/765 | 0 | 0 | 0 | 347 | 246 | 0 |
| | 1 | 190/256 | 74 | 62 | 59 | 119 | 101 | 55 |
| | 3 | 290/302 | 96 | 133 | 98 | 143 | 107 | 92 |
| | 10 | nd | nd | nd | nd | nd | nd | nd |
| | 100 | 222/286 | 77 | 117 | 84 | 146 | 126 | 74 |
| LA928m3 | 0 | 68/1026 | 6.6 | 13 | 4 | 489 | 449 | 1.8 |
| | 0.1 | 0/265 | 0 | 0 | 0 | 117 | 91 | 0 |
| | 1 | 358/446 | 80 | 154 | 100 | 228 | 164 | 65 |
| | 3 | 105/105 | 100 | 39 | 35 | 42 | 38 | 93 |
| | 10 | nd | nd | nd | nd | nd | nd | nd |
| | 100 | 245/245 | 100 | 109 | 121 | 117 | 108 | 100 |
| LA928f1 | 0 | 17/1331 | 1.3 | 2 | 0 | 639 | 599 | 0.16 |
| | 0.1 | 2/254 | 0.8 | 0 | 0 | 100 | 84 | 0 |
| | 1 | 461/567 | 81 | 218 | 146 | 244 | 181 | 85 |
| | 3 | 520/527 | 99 | 214 | 182 | 249 | 202 | 88 |
| | 10 | 350/399 | 91 | 139 | 112 | 131 | 159 | 87 |
| | 100 | 126/117 | 108 | 63 | 57 | 57 | 49 | 113 |
| LA1124f1 | 0 | 104/213 | 51 | 0 | 3 | 95 | 62 | 1.9 |
| | 100 | 478/536 | 89 | 218 | 208 | 205 | 203 | 104 |
| LA1124m1 | 0 | 337/437 | 77 | 2 | 1 | 176 | 207 | 0.78 |
| | 100 | 84/90 | 93 | 35 | 31 | 30 | 26 | 118 |
| LA1124m2 | 0 | 104/145 | 72 | 0 | 1 | 46 | 34 | 1.3 |
| | 100 | 77/77 | 100 | 24 | 14 | 19 | 13 | 119 |

F: fluorescent;
NF: non-fluorescent.

Pupae were collected and scored for fluorescence (column 3), then allowed to eclose. Surviving adults were scored for sex and fluorescence (columns 5-8). From these data on adults, the ratio of fluorescent to non-fluorescent survivors was calculated, presented in column 9 as the percentage of fluorescent adults observed relative to non-fluorescent. It is to be expected that these crosses give, on average, equal numbers of transgenic and non-transgenic individuals; if an equal proportion of transgenic and non-transgenic individuals were to survive to adulthood, then this would give an "adult survival ratio" of 100%.

We further investigated the expression of tTA in these transgenic lines by quantitative (real-time) rt-PCR (qPCR). The results are given in Table 13, below.

TABLE 13

Expression levels of tTA in wild type and transgenic medfly

| Sample | tTA/18S ratio | NT/T ratio |
|---|---|---|
| Larvae | | |
| WT tet | 3.13E−06 | |
| WT NT | 2.81E−06 | |
| 656 tet | 5.80E−06 | 1.00 |
| 656 NT | 2.06E−04 | 36 |
| 670A tet | 2.71E−06 | 1.00 |
| 670A NT | 1.10E−04 | 41 |
| 670e tet | 9.70E−06 | 1.00 |
| 670e NT | 8.40E−05 | 8.7 |
| Adults | | |
| WT female | 2.83E−06 | |
| WT male | 2.16E−07 | |
| Heterozygous | | |
| 656 tet M 0 d | 5.52E−06 | 1.00 |
| 656 tet M 8 d | 1.12E−05 | 2.0 |
| 656 NT M 0 d | 4.49E−05 | 8.1 |
| 656 NT M 2 d | 2.77E−04 | 50 |
| 656 NT M 4 d | 2.22E−04 | 40 |
| 656 NT M 8 d | 9.71E−05 | 18 |
| 656 NT M 16 d | 1.49E−04 | 27 |
| 670 M tet | 4.21E−06 | 1.00 |
| 670 F tet | 2.86E−06 | 0.68 |
| 670 M NT S | 6.93E−05 | 16.45 |
| 670 F NT S | 1.92E−04 | 45.57 |
| 928Am1 F tet | 7.17E−06 | 1.00 |
| 928Am1 M tet | 8.56E−06 | 1.19 |
| 928Am1 M NT 2 d | 1.71E−04 | 23.81 |
| 928Am1 M NT 4 d | 5.36E−04 | 74.72 |
| 928Am1 M NT 8 d | 1.91E−04 | 26.66 |
| 928Am1 M NT 16 d | 1.01E−05 | 1.41 |
| 928Am1 M tet 8 d | 1.11E−06 | 0.16 |
| 928Am1 M NT S | 2.22E−04 | 31.02 |
| 928Am1 M NT S | 1.51E−04 | 21.11 |
| 928Am3 F tet | 9.09E−07 | 1.00 |
| 928Am3 M tet | 9.09E−07 | 1.00 |
| 928Am3 F NT S | 3.62E−05 | 39.85 |
| 928Am3 F NT S | 8.74E−04 | 962.07 |
| 928Am3 F NT S | 2.99E−04 | 329.32 |
| 928Am3 M NT S | 5.53E−05 | 60.83 |
| 928Am3 M NT S | 9.18E−04 | 1009.90 |
| 1124f1 F tet | 2.86E−05 | 1.00 |
| 1124f1 F NT 7 d | 4.11E−04 | 14.35 |
| 1124m1 M tet | 1.62E−05 | 1.00 |
| 1124m1 F NT S | 9.30E−04 | 57.55 |
| 1124m2 F tet | 8.98E−05 | 1.00 |
| 1124m2 F NT 7 d | 7.90E−04 | 8.79 |
| homozygous | | |
| 656 tet 8 d | 1.49E−05 | 1.00 |
| 656 NT 0 d | 9.23E−05 | 6.2 |
| 656 NT 2 d | 3.90E−03 | 262 |
| 656 NT 4 d | 1.92E−03 | 129 |
| 656 NT 8 d | 4.70E−03 | 316 |
| 656 NT 16 d | 8.58E−04 | 58 |

M: male;
F: female;
tet: raised on diet supplemented with tetracycline to 100 μg/ml;
NT S: raised on standard diet (0 μg/ml tetracycline);
d: days post-eclosion;
NT (n)d: raised on tet diet, then held as adults on non-tet (NT) diet for n days, as indicated;
tet (n)d: raised on tet diet, then held as adults on tet diet for n days, as indicated.

Example 9

LA670 in *Ceratitis capitata*

Figure 13:
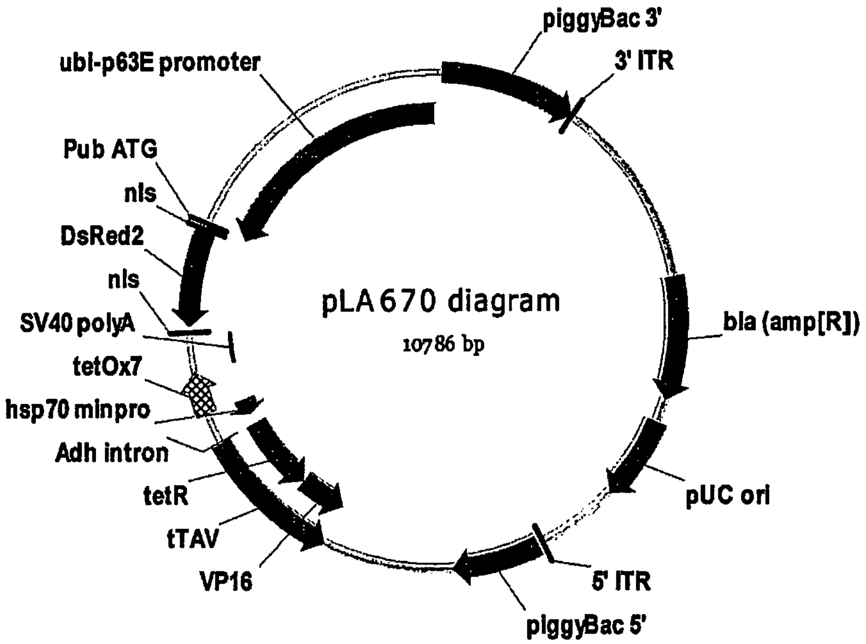
FIG. 13 is a schematic diagram of pLA670.

We obtained a single transgenic line of medfly by transformation with pLA670, a construct which closely resembles pLA656. This plasmid is illustrated in accompanying FIG. 13, and is SEQ ID NO. 23.

However, this transgenic line gave a significant number of adult transgenic progeny, even when raised as larvae on diet lacking tetracycline (Table 14). However, this LA670 insertion line does produce a readily detectable amount of tTAV mRNA in the absence of tetracycline, and this is substantially reduced by dietary tetracycline (assessed by qPCR, results shown in Table 13, above). LA670, therefore, represents a useful regulatable source of tTAV with which to drive the expression of tTAV-responsive genes. The difference in phenotype between LA656 and LA670, which are extremely similar in structure, is probably due to position effect, which is the variation in expression of transgenes depending on where they have inserted in the genome. Such variation is also shown by the variation in phenotype and tTAV expression levels between different transgenic lines with the same construct, as shown in Table 13, above. A simple method for obtaining transgenic lines carrying positive feedback constructs with different expression levels and phenotypic consequences is therefore provided, comprising generating a panel of insertion lines and screening for suitable basal and de-repressed expression levels and patterns.

TABLE 14

Effect of tetracycline on the survival of transgenic medfly heterozygous for LA670, and their +/+ siblings

| | Progeny [Tc] (μg/ml) | F/NF pupae | Pupal survival ratio (%) | F male | F female | NF male | NF female | Adult survival ratio (%) |
|---|---|---|---|---|---|---|---|---|
| LA670 | 0 | 182/220 | 83 | 72 | 35 | 102 | 103 | 52 |
| | 100 | 10/8 | 125 | 5 | 3 | 5 | 3 | 100 |

F: fluorescent;
NF: non-fluorescent.

Pupae were collected and scored for fluorescence (column 3), then allowed to eclose. Surviving adults were scored for sex and fluorescence (columns 5-8). From these data on adults, the ratio of fluorescent to non-fluorescent survivors was calculated, presented in column 9 as the percentage of fluorescent adults observed relative to non-fluorescent. It is to be expected that these crosses give, on average, equal numbers of transgenic and non-transgenic individuals; if an equal proportion of transgenic and non-transgenic individuals survived to adulthood, this would give an "adult survival ratio" of 100%.

Figure 14:
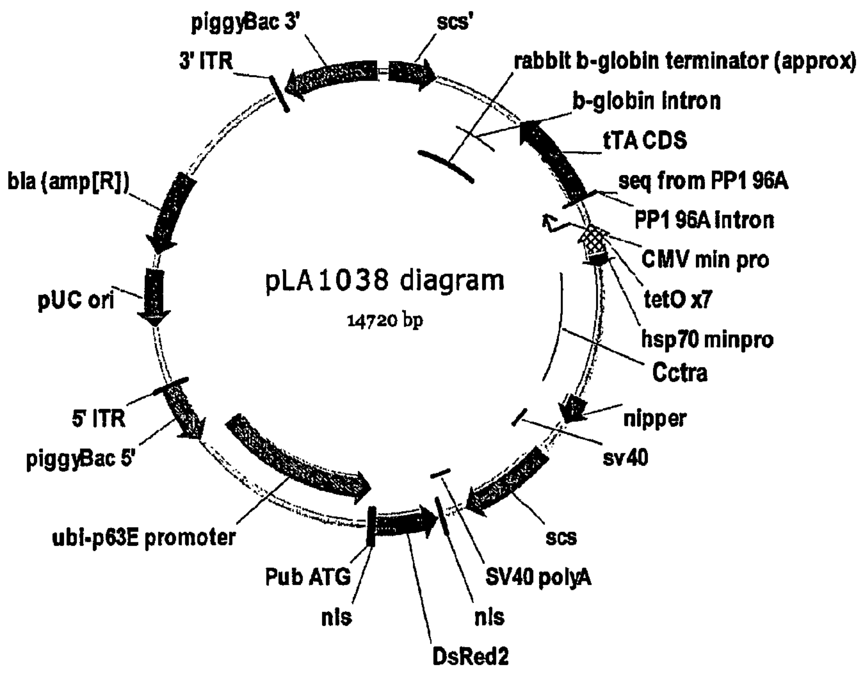
FIG. 14 is a schematic diagram of pLA1038.

We tested the ability of LA670 to drive expression of sequences placed under the transcriptional control of tetO. We analysed the expression of two potential mRNAs from pLA1038 (FIG. 14, SEQ ID NO. 24), which contains two potential tTA-responsive transcription units, divergently transcribed. These are CMV-tTA and hsp70-Cctra-nipper. PCR analysis, with controls, was performed on the expression of these transcription units in the presence and absence of pLA670. Both transcription units are expressed in the presence of pLA670. CMV-tTA is expressed at a lower, but detectable, level in LA1038/+ transgenics in the absence of LA670. hsp70-Cctra-nipper is not detectably expressed in the absence of pLA670, showing that expression is indeed driven by, and dependent on, tTAV supplied by pLA670.

Example 10

LA710 in *Pectinophora gossypiella*

Figure 15:
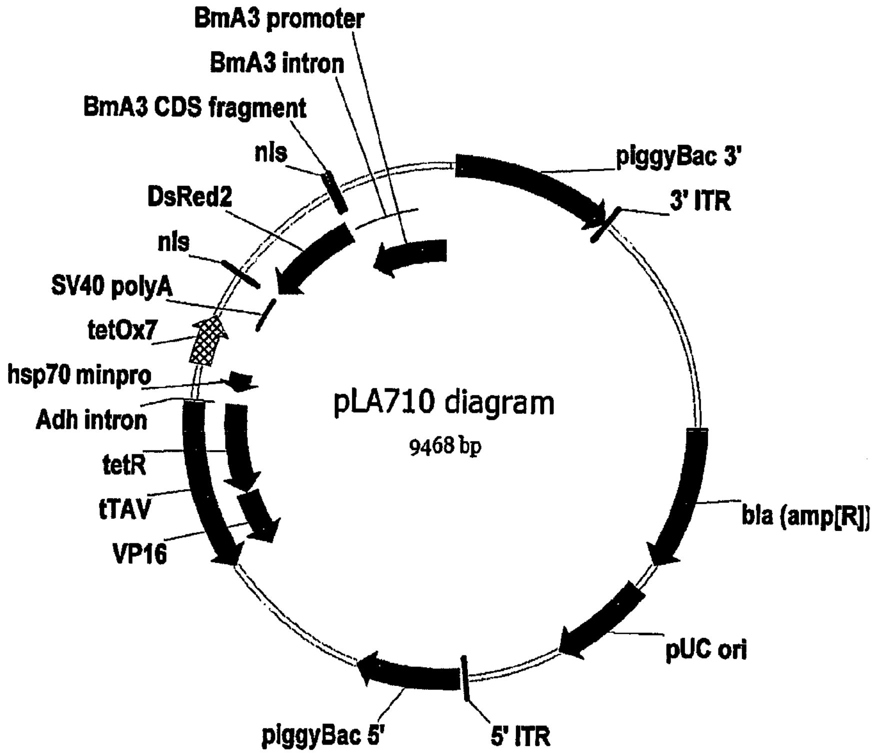
FIG. 15 is a schematic diagram of pLA710.

*Pectinophora gossypiella* (pink bollworm, a lepidopteran) was transformed with LA710 (FIG. 15, SEQ ID NO. 19) by standard methods (Peloquin et al., 2000). Four transgenic lines were recovered. Males of these lines were crossed with females wild type for LA710. Newly hatched larvae were placed in individual 1.7 ml vials with diet, either with or without 7-chlortetracycline (40 μg/ml), and scored for fluorescence. No significant difference was observed in the numbers of transgenics surviving to adulthood relative to numbers of their wild type siblings, either with or without chlortetracycline. We conclude that LA710 does not typically lead to the accumulation of lethal levels of tTAV, even in the absence of dietary chlortetracycline.

We examined the expression of tTAV mRNA in LA710 transgenics by PCR following a reverse transcriptase reaction (rt-PCR). We found that tTAV mRNA was not detectable in chlortetracycline-fed larvae, but was detectable in larvae which had not received chlortetracycline (data not shown). This positive feedback construct LA710, therefore, provides, in these moths, a source of tTAV that can be regulated by supplying dietary chlortetracycline, and for which de-repressed expression, though readily detectable, is non-lethal. We also observed significant variation in the intensity of the band corresponding to tTAV mRNA in samples from different lines.

Example 11

LA1124 in *Pectinophora gossypiella*

*Pectinophora gossypiella* (pink bollworm, a lepidopteran) was transformed with LA1124 (FIG. 12, SEQ ID NO. 21) by standard methods (Peloquin et al., 2000). A single transgenic line was recovered. Males of this line were crossed with females wild type for LA1124. Newly hatched larvae were placed in individual 1.7 ml vials with diet, either with or without 7-chlortetracycline (40 μg/ml), and scored for fluorescence. These larvae were screened again when they had had time to develop to a late larval stage. All larvae survived, except for the fluorescent (LA1124/+) larvae on diet lacking chlortetracycline, as shown in Table 15, below.

TABLE 15

Pink bollworm: survival from early to late larval stage of LA1124/+ or their wild type siblings, on diet with or without chlortetracycline

| 100 μg/ml chlortetracycline | | 0 μg/ml chlortetracycline | |
|---|---|---|---|
| LA1124/+ | Wild-type | LA1124/+ | Wild-type |
| 3 (0 dead) | 11 (0 dead) | 8 (8 dead) | 7 (0 dead) |

We examined the expression of tTAV mRNA in LA1124 pink bollworm by PCR following a reverse transcriptase reaction (rt-PCR). We found that tTAV mRNA was readily detectable in chlortetracycline-fed larvae, but considerably elevated in larvae which had not received chlortetracycline (data not shown). The significant basal expression of tTAV mRNA in this construct is probably due to the inclusion in LA1124 of the hr enhancer, which was included for this reason. Comparison of the structure and function of LA1124 with that of LA710 clearly illustrates that basal and maximum levels of the gene product can readily be selected by appropriate modification of the expression construct, this principle being demonstrated, here, by regulating levels of expression of a tTAV-dependent RNA (in this case the tTAV mRNA).

Example 12

Sex-specific Expression Using Positive Feedback

It is preferred to control, by design, the expression of tTAV from a positive feedback construct, so that it can be differentially expressed in different tissues, or different developmental stages, or different sexes, for example. One application for this is in genetic sexing, in which a sexual dimorphism is induced between the two sexes and this is used as a basis for separating the two sexes. In the context of the Sterile Insect Technique, e.g. for medfly, this preferably means killing the females, most preferably at an early stage in their development. No early-acting female-specific promoters are known for medfly, which limits the potential of the two-component repressible dominant lethal system exemplified for *Drosophila* using promoters or enhancers from yolk protein genes (Heinrich and Scott, 2000; Thomas et al., 2000). It would clearly be advantageous to be able to combine the beneficial characteristics of a conditional positive feedback system with a mechanism conferring female specificity.

Figure 16:
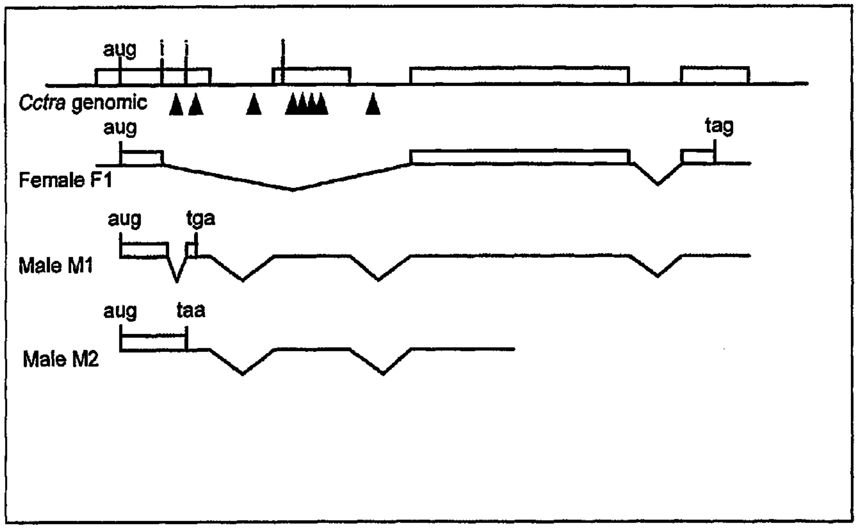
FIG. 16 illustrates the sex-specific splicing of Cctra in medfly.

We, therefore, modified a non-sex-specific positive feedback construct by inserting a sex-specific intronic region from Cctra, the medfly homologue of the *Drosophila melanogaster* gene transformer (Pane et al, 2002). The sex-specific splicing of Cctra is illustrated diagrammatically in FIG. 16, which is adapted from (Pane et al, 2002) supra. FIG. 16 shows the genomic organisation of the medfly tra gene. The top line represents the genomic Cctra locus. Exons are shown as blocks; aug marks the shared start codon. The alternate splice junctions are marked i. Putative tra/tra-2 binding sites are marked with arrowheads. Transcript F1, the only one to encode functional Cctra protein, is specific to females. Transcripts M1 and M2 are found in both males and females.

Three main transcripts are produced: M1, M2 and F1. Transcript F1 is found only in females, and is the only one to encode full-length, functional Cctra protein. Transcripts M1 and M2 are found in both males and females, and include additional exonic sequence, which inserts one or more stop codons relative to transcript F1, leading to truncation of the open reading frame.

Figure 17:
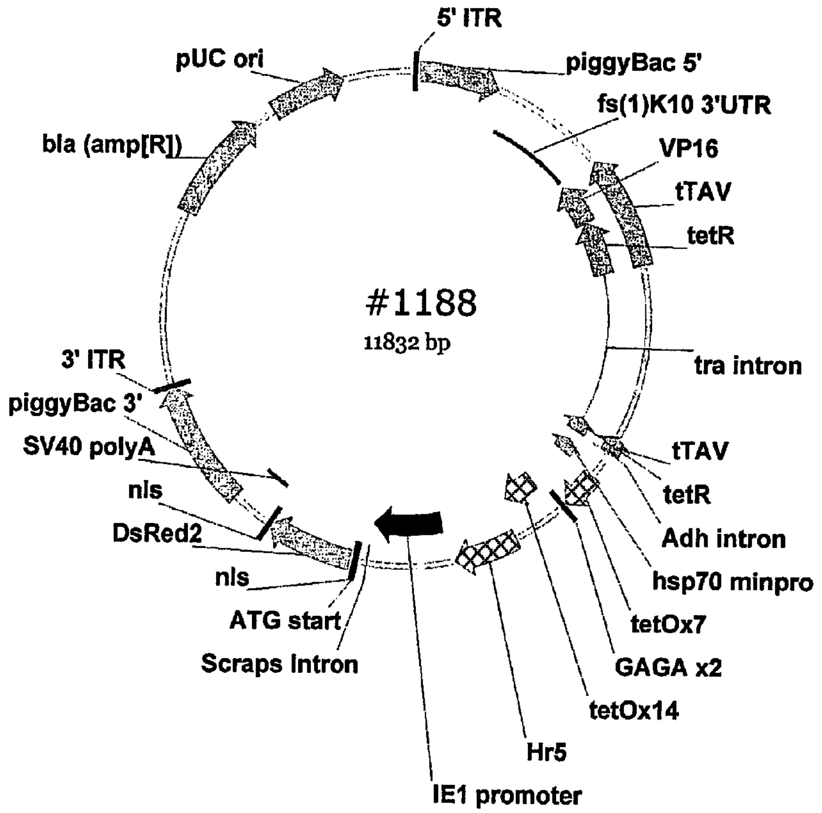
FIG. 17 is a schematic diagram of pLA1188.

We inserted the Cctra intron into the open reading frame of tTAV, so that excision by splicing of the complete intron, in the manner of transcript F1, would reconstitute an intact tTAV coding region, but splicing in the manner of either M1 or M2 would result in a truncated protein incapable of acting as a transcriptional enhancer. The resulting plasmid, pLA1188 (FIG. 17, SEQ ID NO. 22), was injected into medfly embryos. Surviving larvae were recovered, and extracts from these larvae were analysed by rt-PCR to determine the splicing pattern of the tTAV transcript.

Figure 18:
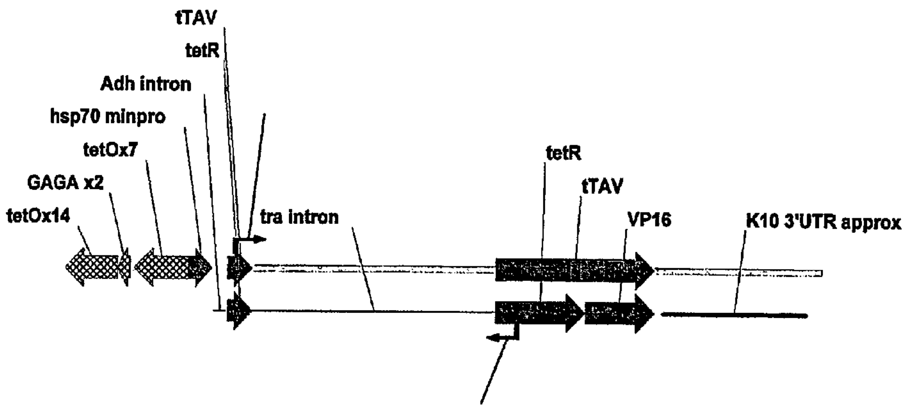
FIG. 18 illustrates sex-specific splicing in medfly.

Female larvae yielded PCR products corresponding to the expected sizes that would result from splicing in the pattern of the endogenous Cctra gene, in other words corresponding to splicing in the M1, M2 and F1 patterns. These data indicate that the Cctra intron can splice correctly in a heterologous context and, therefore, provides a suitable method for introducing sex-specificity into a positive feedback construct. Furthermore, since tra function is conserved across a wide phylogenetic range (Saccone et al., 2002), and other sex-specific introns are known, e.g. in the *Drosophila melanogaster* gene double-sex (dsx), which is also well conserved, this provides a general method for manipulating the expression of genes. It will be apparent to the person skilled in the art that such manipulations can alternatively, or additionally, be applied to other genes responsive to a transcriptional activator, so that sex-specific expression of a target gene can be achieved by combining non-sex-specific expression of a transcriptional activator with sex-specific expression, e.g. through splicing, of a functional RNA under the transcriptional control of the transcriptional activator. Furthermore, it will also be apparent that this provides a simple mechanism for differential expression of two, or more, different target genes, or gene products, such that one, or one group, is expressed in both sexes and the other, or other group, in only one sex. This is illustrated for medfly in FIG. 18.

The primers used were:

```
                              (SEQ ID NO. 12)
Tra(tTAV)Seq+: 5'-CCTGCCAGGACTCGCCTTCC

                              (SEQ ID NO. 13)
Tra(tTAV)Seq-: 5'-GTCATCAACTCCGCGTTGGAGC
```

RT-PCR products of ~600 and ~200 bp were produced when cDNA derived from female medflies 1 and 2 was used as a template, representing "male" (M1 and M2) and female-specific (F1) spliced forms of mRNA respectively (data not shown). The ~200 bp product could have been produced due to contamination with tTAV DNA—the female spliced form completely removes the Cctra intron an so leads to a PCR product that is identical to that which would be obtained from any of several tTAV-containing plasmids or samples handled in the same laboratory. The ~600 bp band, in contrast, retains ~400bp of Cctra sequence and is diagnostic of correct splicing of the construct.

In another experiment (data not shown), expression of transcripts from LA1038 in response to tTAV from LA670 was analysed by gel chromatography (data not shown), using:

A: rt-PCR for expression of CMV-tTA from LA1038 in extracts from LA1038/+, LA670/+ double heterozygotes;

B: rt-PCR for expression of hsp70-Cctra-nipper in extracts from LA1038/+, LA670/+ double heterozygotes; and C: rt-PCR for expression of CMV-tTA from LA1038 in extracts from LA1038/+ heterozygotes without LA670.

All flies were raised in the absence of dietary tetracycline. In A and C, two bands were present between 200 bp and 400 bp and represent cDNA from spliced mRNA (lower molecular weight band) and genomic DNA or cDNA from unspliced message (higher molecular weight band) respectively. In B, a band at approximately 200 bp represents cDNA from mRNA spliced in the pattern of the Cctra female-specific F1 transcript, an upper band of approximately 1500 bp representing genomic DNA or cDNA from unspliced message, and bands of intermediate size representing cDNA spliced in the pattern of the Cctra non-sex-specific M1 and M2 transcripts, or non-specific bands.

Primer Sequences Used Were:

```
hsp70-Cetra-nipper:
NIP: 5'-CATCGATGCCCAGCATTGAGATG
and

HSP: 5'-CAAGCAAAGTGAACACGTCGCTAAGCGAAAGCTA;

CMV-tTA:
CMV: 5'-GCCATCCACGCTGTTTTGACCTCCATAG
and

TTA: 5'-GCCAATACAATGTAGGCTGCTCTACAC
```

These data (not shown) demonstrate that the hsp-Cctra-nipper section of LA1038 is shown to be correctly spliced in the female form in 6/6 females, and in the male form in 6/6 males.

REFERENCE SEQUENCES

JY2004-tTA (SEQ ID NO. 14)—sequence of the $tetO_7$-tTA region only
pP[Casper-Act5C-tTA] (SEQ ID NO. 15)
pLA513 (SEQ ID NO. 16)
pLA517 (SEQ ID NO. 17)
pLA656 (SEQ ID NO. 18)
pLA670 (SEQ ID NO. 23)
pLA710 (SEQ ID NO. 19)
pLA928 (SEQ ID NO. 20)
pLA1038 (SEQ ID NO. 24)
pLA1124 (SEQ ID NO. 21)
pLA1188 (SEQ ID NO. 22)

REFERENCES

Alphey, L. (2002). Re-engineering the Sterile Insect Technique. Insect Biochem Mol Biol 32, 1243-1247.

Alphey, L., and Andreasen, M. H. (2002). Dominant lethality and insect population control. Mol Biochem Parasitol 121, 173-178.

Alphey, L., Beard, B., Billingsley, P., Coetzee, M., Crisanti, A., Curtis, C. F., Eggleston, P., Godfray, C., Hemingway, J., Jacobs-Lorena, M., et al. (2002). Malaria control with genetically modified vectors. Science 298, 119-121.

Baron, U., and Bujard, H. (2000). Tet repressor-based system for regulated gene expression in eukaryotic cells: principles and advances. Meth Enzymol 327.

Baron, U., Gossen, M., and Bujard, H. (1997). Tetracycline-controlled transcription in eukaryotes: novel transactivators with graded transactivation potential. Nucl Acids Res 25, 2723-2729.

Bello, B., Resendez-Perez, D., and Gehring, W. (1998). Spatial and temporal targeting of gene expression in *Drosophila* by means of a tetracycline-dependent transactivator system.

Development 125, 2193-2202.
Benedict, M., and Robinson, A. (2003). The first releases of transgenic mosquitoes: an argument for the sterile insect technique. Trends Parasitol 19, 349-355.
Bennett, D., Szoor, B., Gross, S., Vereshchagina, N., and Alphey, L. (2003). Ectopic expression of inhibitors of Protein Phosphatase type 1 (PP1) can be used to analyse roles of PP1 in *Drosophila* development. Genetics 164, 235-245.
Berger, S. L., Cress, W. D., Cress, A., Triezenberg, S. J., and Guarente, L. (1990). Selective inhibition of activated but not basal transcription by the acidic activation domain of VP16: evidence for transcriptional adaptors. Cell 61, 1199-1208.
Berghammer, A. J., Klingler, M., and Wimmer, E. A. (1999). A universal marker for transgenic insects. Nature 402, 370-371.
Brand, A., Manoukian, A., and Perrimon, N. (1994). Ectopic expression in *Drosophila*. Meth Cell Biol 44, 635-654.
Catteruccia, F., Nolan, T., Loukeris, T., Blass, C., Savakis, C., Kafatos, F., and Crisanti, A. (2000). Stable germline transformation of the malaria mosquito *Anopheles stephensi*. Nature 405, 959-962.
Coates, C., Jasinskiene, N., Miyashiro, L., and James, A. (1998). Mariner transposition and transformation of the yellow fever mosquito, *Aedes aegypti*. Proc Natl Acad Sci USA 95, 3748-3751.
Damke, H., Gossen, M., Freundlieb, S., Bujard, H., and Schmid, S. (1995). Tightly regulated and inducible expression of dominant interfering dynamin mutant in stably transformed HeLa cells. Meth Enz 257, 209-220.
Fussenegger, M. (2001). The impact of mammalian gene regulation concepts on functional genomic research, metabolic engineering, and advanced gene therapies. Biotechnol Prog 17, 1-51.
Fussenegger, M., Mazur, X., and Bailey, J. (1998a). pTRIDENT, a novel vector family for tricistronic expression in mammalian cells. Biotech Bioeng 57, 1-10.
Fussenegger, M., Moser, S., and Bailey, J. (1998b). pQuattro vectors allow one-step transfection and auto-selection of quattrocistronic artificial mammalian operons. Cytotechnology 28, 229-235.
Gebauer, F., Merendino, L., Hentze, M. W., and Valcarcel, J. (1998). The *Drosophila* splicing regulator sex-lethal directly inhibits translation of male-specific-lethal 2 mRNA. RNA 4, 142-150.
Gill, G., and Ptashne, M. (1988). Negative effect of the transcriptional activator GAL4. Nature 334, 721-724.
Gossen, M., Bonin, A., Freundlieb, S., and Bujard, H. (1994). Inducible gene expression systems for higher eukaryotic cells. Curr Opin Biotechnol 5, 516-520.
Gossen, M., and Bujard, H. (1992). Tight control of gene expression in mammalian cells by tetracycline-responsive promoters. Proc Natl Acad Sci USA 89, 5547-5551.
Handler, A. (2002). Use of the piggyBac transposon for germline transformation of insects. Insect Biochem Mol Biol 32, 1211-1220.
Handler, A., and James, A. (2000). Insect transgenesis: methods and applications (Boca Raton, CRC Press).
Heinrich, J., and Scott, M. (2000). A repressible female-specific lethal genetic system for making transgenic insect strains suitable for a sterile-release program. Proc Nat'l Acad Sci (USA) 97, 8229-8232.
Hom, C., Schmid, B., Pogoda, F., and Wimmer, E. (2002). Fluorescent transformation markers for insect transgenesis. Insect Biochem Mol Biol 32, 1221-1235.
Jasinskiene, N., Coates, C., Benedict, M., Cornel, A., Rafferty, C., James, A., and Collins, F. (1998). Stable transformation of the yellow fever mosquito, *Aedes aegypti*, with the Hermes element from the housefly. Proc Natl Acad Sci USA 95, 3743-3747.
Kelley, R. L., Solovyeva, I., Lyman, L. M., Richman, R., Solovyev, V., and Kuroda, M. I. (1995). Expression of msl-2 causes assembly of dosage compensation regulators on the X chromosomes and female lethality in *Drosophila*. Cell 81, 867-877.
Lobo, N., Hua-Van, A., Li, X., Nolen, B., and Fraser, M. (2002). Germ line transformation of the yellow fever mosquito, *Aedes aegypti*, mediated by transpositional insertion of a piggyBac vector. Insect Molecular Biology 11, 133-139.
Lozovsky, E., Nurminsky, D., Wimmer, E., and Hartl, D. (2002). Unexpected stability of mariner transgenes in *Drosophila*. Genetics 160, 527-535.
Matsuo, T., Takahashi, K., Kondo, S., Kaibuchi, K., and Yamamoto, D. (1997). Regulation of cone cell formation by Canoe and Ras in the developing *Drosophila* eye. Development 124, 2671-2680.
McCombs, S., and Saul, S. (1995). Translocation-based genetic sexing system for the oriental fruit-fly (Diptera, Tephritidae) based on pupal color dimorphism. Ann Ent Soc Am 88, 695-698.
Moreira, L., Wang, J., Collins, F., and Jacobs-Lorena, M. (2004). Fitness of anopheline mosquitoes expressing transgenes that inhibit Plasmodium development. Genetics 166, 1337-1341.
Pane, A., Salvemini, M., Delli Bovi, P., Polito, C., and Saccone, G. (2002). The transformer gene in *Ceratitis capitata* provides a genetic basis for selecting and remembering the sexual fate. Development 129, 3715-3725.
Parker, L., Gross, S., Beullens, M., Bollen, M., Bennett, D., and Alphey, L. (2002). Functional interaction between NIPP1 and PP1 in *Drosophila:* lethality of over-expression of NIPP1 in flies and rescue by the over-expression of PP1. Biochem J 368, 789-797.
Peloquin, J. J., Thibault, S. T., Staten, R., and Miller, T. A. (2000). Germ-line transformation of pink bollworm (Lepidoptera: gelechiidae) mediated by the piggyBac transposable element. Insect Mol Biol 9, 323-333.
Perera, O., Harrell, R., and Handler, A. (2002). Germ-line transformation of the South American malaria vector, *Anopheles albimanus*, with a piggyBac-EGFP tranposon vector is routine and highly efficient. Insect Molecular Biology 11, 291-297.
Pinkerton, A., Michel, K., O'Brochta, D., and Atkinson, P. (2000). Green fluorescent protein as a genetic marker in transgenic *Aedes aegypti*. Insect Molecular Biology 9, 1-10.
Reichhart, J., and Ferrandon, D. (1998). Green balancers. *Drosophila* Information Service 81, 201-202.
Rorth, P. (1998). Gal4 in the *Drosophila* female germline. Mech Dev 78, 113-118.
Saccone, G., Pane, A., and Polito, C. (2002). Sex determination in flies, fruitfles and butterflies. Genetica 116, 15-23.
Salghetti, S., Caudy, A., Chenoweth, J., and Tansey, W. (2001). Regulation of transcriptional activation domain function by ubiquitin. Science 293, 1651-1653.
Scott, M., Heinrich, J., and Li, X. (2004). Progress towards the development of a transgenic strain of the Australian sheep blowfly (*Lucilia cuprina*) suitable for a male-only sterile release program. Insect Biochem Mol Biol 34, 185-192.
Shockett, P., Difilippantonio, M., Hellman, N., and Schatz, D. (1995). A modified tetracycline-regulated system provides autoregulatory, inducible gene expression in cultured cells and transgenic mice. Proc Nat'l Acad Sci (USA) 92, 6522-6526.

Stebbins, M., and Yin, J. (2001). Adaptable doxycycline-regulated gene expression systems for *Drosophila*. Gene 270, 103-111.

Thomas, D., Donnelly, C., Wood, R., and Alphey, L. (2000). Insect population control using a dominant, repressible, lethal genetic system. Science 287, 2474-2476.

Varshavsky, A. (2000). Ubiquitin fusion technique and its descendants. Meth Enz 327.

The invention claimed is:

1. A repressible insect gene expression system, said system comprising:

(i) a lethal gene encoding a transcriptional control factor, which is a tTA gene product or a repressible variant thereof, wherein the lethal gene is modified to at least partially follow optimized codon usage in an insect for which the system is used; and (ii) a promoter operably linked to the lethal gene, wherein the transcriptional control factor positively controls transcription from said promoter, which is substantially inactive in the absence of the transcriptional control factor, wherein the positive control is repressible, wherein the lethal gene is substantially capable of reducing viability of an insect comprising the system when de-repressed, and wherein the insect is selected from the group consisting of mosquito, bollworm and medfly.

2. The system according to claim 1, wherein an enhancer is operably linked with the promoter.

3. The system according to claim 2, wherein the enhancer comprises one or more tetO operator units operably linked with the promoter.

4. The system according to claim 3, wherein the transcriptional control factor is a tTAV or tTAF.

5. The system according to claim 1, wherein the promoter is a minimal promoter.

6. The system according to claim 5, wherein the promoter is selected from: hsp70, a P minimal promoter, a CMV minimal promoter, an Act5C-based minimal promoter, a BmA3 promoter fragment, an Adh core promoter, and an Act5C minimal promoter, and combinations thereof.

7. The system according to claim 1, wherein the promoter is obtained from, or is a fragment of, CMV or Hsp70.

8. The system according to claim 1, further comprising another gene under the control of another promoter, wherein the transcriptional control factor positively controls transcription from said another promoter, wherein the positive control is repressible.

9. The system according to claim 1, wherein the expression of the transcriptional control factor is selective for sex, species, developmental stage or tissue.

10. The system according to claim 1, wherein the system comprises at least two cistrons.

11. The system according to claim 1, wherein the system is bounded by insulator elements.

12. The system according to claim 11, wherein the elements are non-identical insulators.

13. A vector comprising the system of claim 1.

14. The vector according to claim 13, further comprising a sequence encoding an expression marker.

15. The vector according to claim 14, wherein the expression marker is a fluorescent protein or resistance marker.

16. The system of claim 1, wherein the lethal gene has a fatal effect on insect embryos or larvae, but not adult insects, when de-repressed.

17. An insect comprising the repressible insect gene expression system of claim 1, wherein the insect is selected from the group consisting of mosquito, bollworm and medfly.

* * * * *